United States Patent
Li et al.

(10) Patent No.: US 12,291,537 B2
(45) Date of Patent: May 6, 2025

(54) COMPOUNDS, COMPOSITIONS AND METHODS

(71) Applicant: LaNova Medicines Limited, Shanghai (CN)

(72) Inventors: Runsheng Li, Shanghai (CN); Wentao Huang, Shanghai (CN); Zhifang Liu, Shanghai (CN); Ying Qin Zang, Shanghai (CN)

(73) Assignee: LaNova Medicines Limited, Shanghai (CN)

( * ) Notice: Subject to any disclaimer, the term of this patent is extended or adjusted under 35 U.S.C. 154(b) by 0 days.

(21) Appl. No.: 18/433,717

(22) Filed: Feb. 6, 2024

(65) Prior Publication Data

US 2024/0262841 A1 Aug. 8, 2024

Related U.S. Application Data

(63) Continuation of application No. PCT/CN2023/123581, filed on Oct. 9, 2023.

(30) Foreign Application Priority Data

Oct. 9, 2022 (WO) ................ PCT/CN2022/124073

(51) Int. Cl.
*C07D 491/22* (2006.01)
*A61K 31/4375* (2006.01)
*A61P 35/00* (2006.01)

(52) U.S. Cl.
CPC ........ *C07D 491/22* (2013.01); *A61K 31/4375* (2013.01); *A61P 35/00* (2018.01)

(58) Field of Classification Search
CPC .................................................. C07D 491/22
USPC .......................................................... 546/41
See application file for complete search history.

(56) References Cited

U.S. PATENT DOCUMENTS

| | | |
|---|---|---|
| 6,100,273 A | 8/2000 | Besterman et al. |
| 6,177,439 B1 | 1/2001 | Duvvuri et al. |
| 6,350,756 B1 | 2/2002 | Yang et al. |
| 6,403,604 B1 | 6/2002 | Yang et al. |
| 6,407,115 B1 | 6/2002 | Terasawa et al. |
| 2003/0032624 A1 | 2/2003 | Yang |
| 2004/0266803 A1 | 12/2004 | Wani et al. |
| 2008/0039485 A1 | 2/2008 | Ho et al. |
| 2013/0184454 A1 | 7/2013 | Knoller et al. |
| 2017/0035906 A1 | 2/2017 | Naito et al. |
| 2020/0282073 A1 | 9/2020 | Masuda et al. |
| 2021/0353764 A1 | 11/2021 | Xu et al. |
| 2023/0293712 A1 | 9/2023 | Lannutti et al. |

FOREIGN PATENT DOCUMENTS

| | | | |
|---|---|---|---|
| AU | 2020288275 A1 | 2/2022 | |
| CN | 111065621 A | 4/2020 | |
| CN | 113943310 A | 1/2022 | |
| CN | 114845740 A | 8/2022 | |
| JP | 06-087746 A | * 3/1994 | ........... C07D 491/22 |
| JP | H0687746 A | 3/1994 | |
| WO | WO 9964054 | 12/1999 | |
| WO | WO 2001049691 | 7/2001 | |
| WO | WO 2002040040 | 5/2002 | |
| WO | WO 2012004008 | 1/2012 | |
| WO | WO 2013067449 | 5/2013 | |
| WO | WO 2014061277 A1 | 4/2014 | |
| WO | WO 2015000240 | 1/2015 | |
| WO | WO 2015113176 | 8/2015 | |
| WO | WO 2015148415 | 10/2015 | |
| WO | WO 2016205738 | 12/2016 | |
| WO | WO 2018112253 | 6/2018 | |
| WO | WO 2018175994 | 9/2018 | |
| WO | WO 2019189419 | 10/2019 | |
| WO | WO 2019236954 | 12/2019 | |
| WO | WO 2019238046 | 12/2019 | |
| WO | WO 2020061106 | 3/2020 | |
| WO | WO 2020219287 | 10/2020 | |
| WO | WO 2020257998 | 12/2020 | |
| WO | WO 2021067776 | 4/2021 | |
| WO | WO 2021067820 | 4/2021 | |
| WO | WO 2021067861 | 4/2021 | |
| WO | WO 2021173773 | 9/2021 | |
| WO | WO 2021212638 | 10/2021 | |
| WO | WO 2022053650 | 3/2022 | |
| WO | WO 2022068878 | 4/2022 | |
| WO | WO 2022078279 | 4/2022 | |
| WO | WO 2022112356 A1 | 6/2022 | |
| WO | WO 2022166762 | 8/2022 | |
| WO | WO 2022170971 | 8/2022 | |
| WO | WO 2022198231 | 9/2022 | |
| WO | WO 2022198232 | 9/2022 | |
| WO | WO 2022236136 A1 | 11/2022 | |
| WO | WO 2023004266 | 1/2023 | |
| WO | WO 2023131219 A1 | 7/2023 | |
| WO | WO 2023143365 A1 | 8/2023 | |
| WO | WO 2023186015 A1 | 10/2023 | |

OTHER PUBLICATIONS

International Search Report for PCT/CN2023/123581 mailed Nov. 27, 2023, 6 pages.
Written Opinion of the International Searching Authority for PCT/CN2023/123581 mailed Nov. 27, 2023, 5 pages.

* cited by examiner

*Primary Examiner* — Charanjit Aulakh
(74) *Attorney, Agent, or Firm* — Sheppard, Mullin, Richter & Hampton LLP

(57) ABSTRACT

The present disclosure relates to anticancer compounds, including, but not limited to, antibody-drug conjugates using the same, which compounds and ACDs thereof are suitable for the treatment of cancer.

19 Claims, 7 Drawing Sheets

COMPOUNDS, COMPOSITIONS AND METHODS

CROSS REFERENCE TO RELATED APPLICATIONS

The application is a continuation of International Patent Application Number PCT/CN2023/123581, filed Oct. 9, 2023, which claims the benefit of International Patent Application Number PCT/CN2022/124073, filed on Oct. 9, 2022, each of which is incorporated herein by reference in its entirety.

BACKGROUND

Antibody-drug conjugates (ADCs) are complex molecules comprising an antibody linked to a biologically active cytotoxic payload designed to be a targeted therapy for treating cancer. Unlike traditional chemotherapy, ADCs are intended to target and kill tumor cells while sparing healthy cells.

The concept of targeted delivery of an active pharmaceutical drug to a specific cellular location of choice is a powerful approach for the treatment of a wide range of diseases, with many beneficial aspects versus systemic delivery of the same drug. Whereas there have been ADC therapeutics approved by the FDA, there remains a need for potent, targeted therapies for treating cancers.

SUMMARY

The present disclosure relates to anticancer compounds, including, but not limited to, antibody-drug conjugates using the same, which compounds and ACDs thereof are suitable for the treatment of cancer.

The present disclosure, in one embodiment, provides compounds of Formula I:

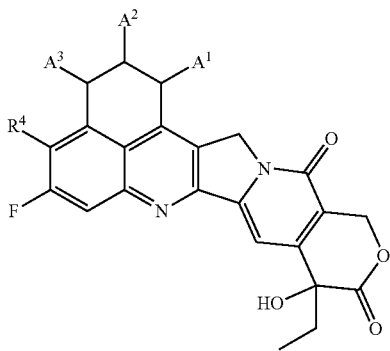

I or stereoisomer or pharmaceutically acceptable salt thereof, wherein:
$A^1$ is —$NHR^1$, where $R^1$ is hydrogen, —$C_6$ aryl-$C_{1-6}$ alkyl-$NH_2$, —$C(O)R^5$, or —$C_6$ aryl-$C_{1-6}$ alkyl-NHC(O) $R^5$; and $A^2$ and $A^3$ are both hydrogen; or
$A^2$ is —$NHR^2$, where $R^2$ is hydrogen, —$C_6$ aryl-$C_{1-6}$ alkyl-$NH_2$, —$C(O)R^5$, or —$C_6$ aryl-$C_{1-6}$ alkyl-NHC(O) $R^5$; and $A^1$ and $A^3$ are both hydrogen; or $A^3$ is —$NHR^3$, where $R^3$ is hydrogen, —$C_6$ aryl-$C_{1-6}$ alkyl-$NH_2$, —$C(O)R^5$, or —$C_6$ aryl-$C_{1-6}$ alkyl-NHC(O)$R^5$; and $A^1$ and $A^2$ are both hydrogen;
$R^4$ is —$C_{1-6}$ alkyl; provided that when $A^1$ is —$NHR^1$, then $R^4$ is other than methyl;
$R^5$ is -L-$R^6$;
L is a linker moiety; and
$R^6$ is hydrogen or heterocyclyl, wherein said heterocyclyl is optionally covalently linked to an antibody or antigen-binding fragment.

Also provided herein are pharmaceutical compositions comprising a compound of Formula I, or a pharmaceutically acceptable salt or solvate thereof, and a pharmaceutically acceptable excipient.

Also provided herein are methods for treating cancer in a patient in need thereof, comprising administering to said patient a therapeutically acceptable amount of a compound as described herein, or a stereoisomer or pharmaceutically acceptable salt thereof, or a pharmaceutical composition comprising the same. Exemplary cancers include, but are not limited to, lung cancer, kidney cancer, urethral cancer, colorectal cancer, prostate cancer, glioblastoma multiforme, ovarian cancer, pancreatic cancer, breast cancer, melanoma, liver cancer, bladder cancer, stomach cancer, and esophageal cancer.

Also provided herein are methods for treating, preventing, or inhibiting tumor growth in a patient in need thereof, comprising administering to said patient a therapeutically acceptable amount of a compound as described herein, or a stereoisomer or pharmaceutically acceptable salt thereof, or a pharmaceutical composition comprising the same.

BRIEF DESCRIPTION OF THE FIGURES

FIG. TA shows binding of HER2 antibody drug conjugates to NCI-N87 cells.

DETAILED DESCRIPTION

Definitions

Figure 1:
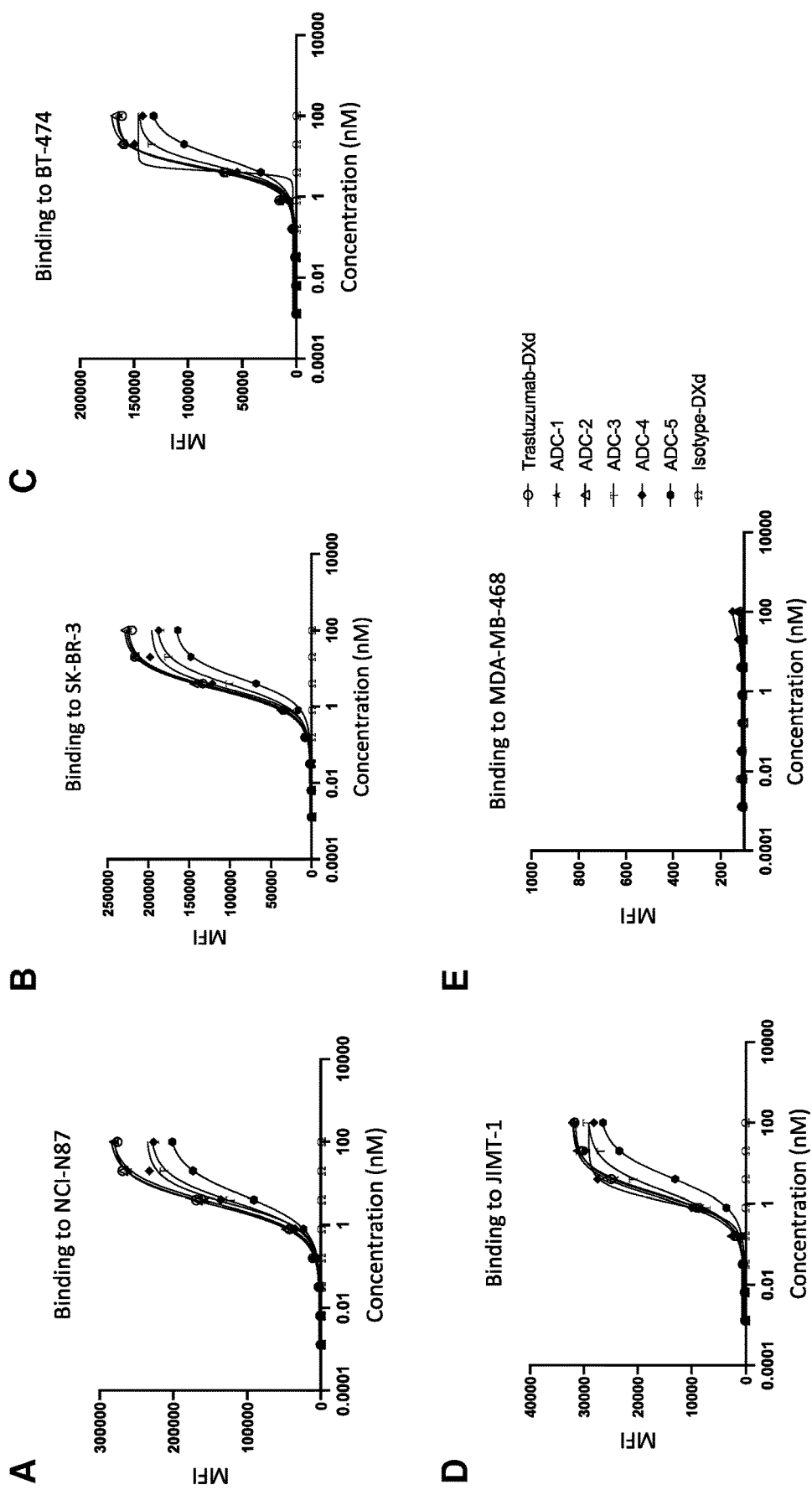
FIG. 1B shows binding of HER2 antibody drug conjugates to SK-BR-3 cells.
FIG. 1C shows binding of HER2 antibody drug conjugates to BT-474 cells.
FIG. 1D shows binding of HER2 antibody drug conjugates to JIMT-1 cells.
FIG. 1E shows binding of HER2 antibody drug conjugates to MDA-MB-468 cells.
Figure 2:
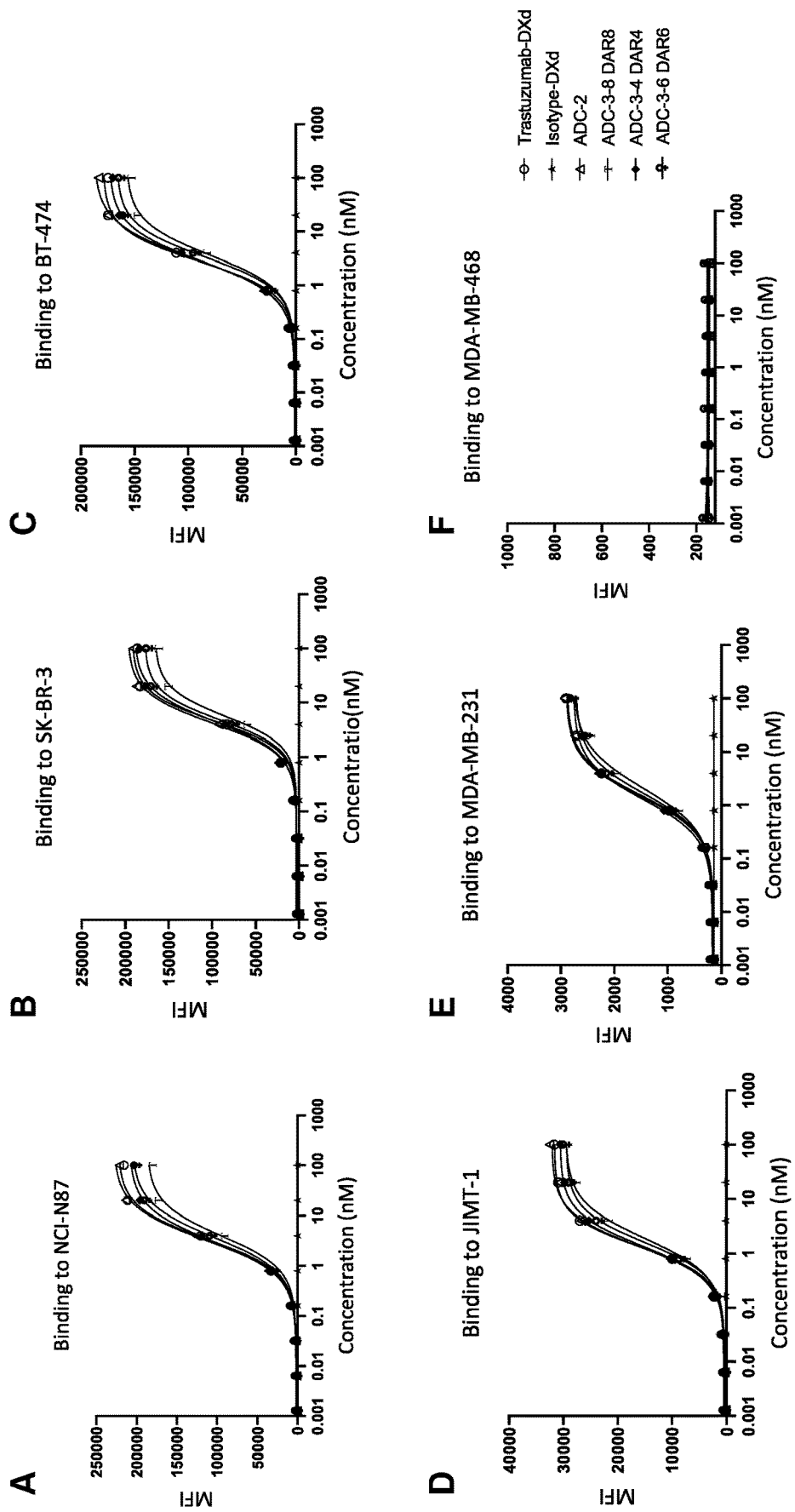
FIG. 2A shows binding of HER2 antibody drug conjugates with a drug to antibody ratio of 4 (ADC-3-4), 6 (ADC-3-6), and 8 (ADC-3-8) to NCI-N87 cells.
FIG. 2B shows binding of HER2 antibody drug conjugates with a drug to antibody ratio of 4 (ADC-3-4), 6 (ADC-3-6), and 8 (ADC-3-8) to SK-BR-3 cells.
FIG. 2C shows binding of HER2 antibody drug conjugates with a drug to antibody ratio of 4 (ADC-3-4), 6 (ADC-3-6), and 8 (ADC-3-8) to BT-474 cells.
FIG. 2D shows binding of HER2 antibody drug conjugates with a drug to antibody ratio of 4 (ADC-3-4), 6 (ADC-3-6), and 8 (ADC-3-8) to JIMT-1 cells.
FIG. 2E shows binding of HER2 antibody drug conjugates with a drug to antibody ratio of 4 (ADC-3-4), 6 (ADC-3-6), and 8 (ADC-3-8) to MDA-MB-231 cells.
FIG. 2F shows binding of HER2 antibody drug conjugates with a drug to antibody ratio of 4 (ADC-3-4), 6 (ADC-3-6), and 8 (ADC-3-8) to MDA-MB-468 cells.
Figure 3:
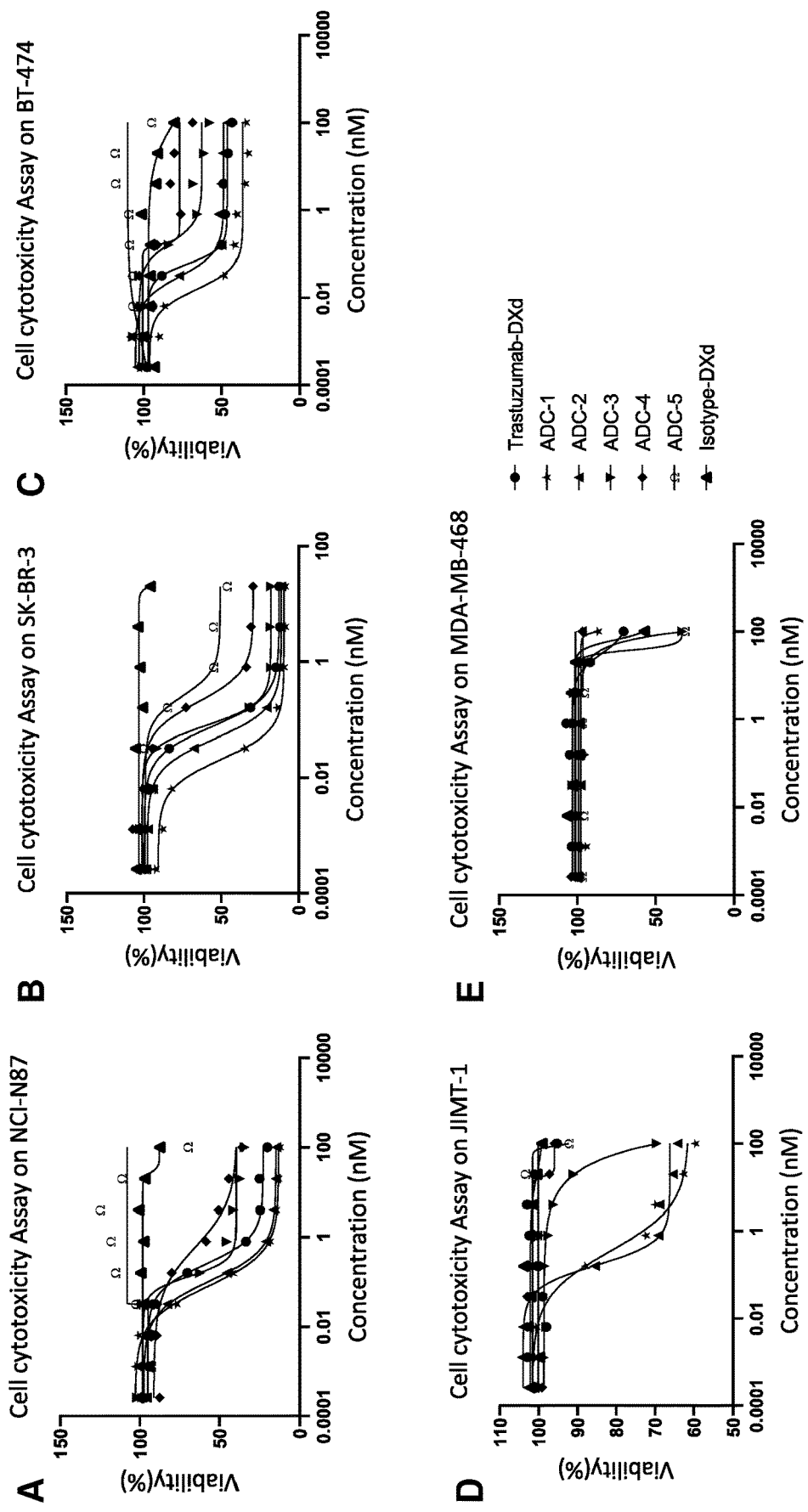
FIG. 3A shows cytotoxicity of HER2 antibody drug conjugates in NCI-N87 cells.
FIG. 3B shows cytotoxicity of HER2 antibody drug conjugates in SK-BR-3 cells.
FIG. 3C shows cytotoxicity of HER2 antibody drug conjugates in BT-474 cells.
FIG. 3D shows cytotoxicity of HER2 antibody drug conjugates in JIMT-1 cells.
FIG. 3E shows cytotoxicity of HER2 antibody drug conjugates in MDA-MB-468 cells.
Figure 4:
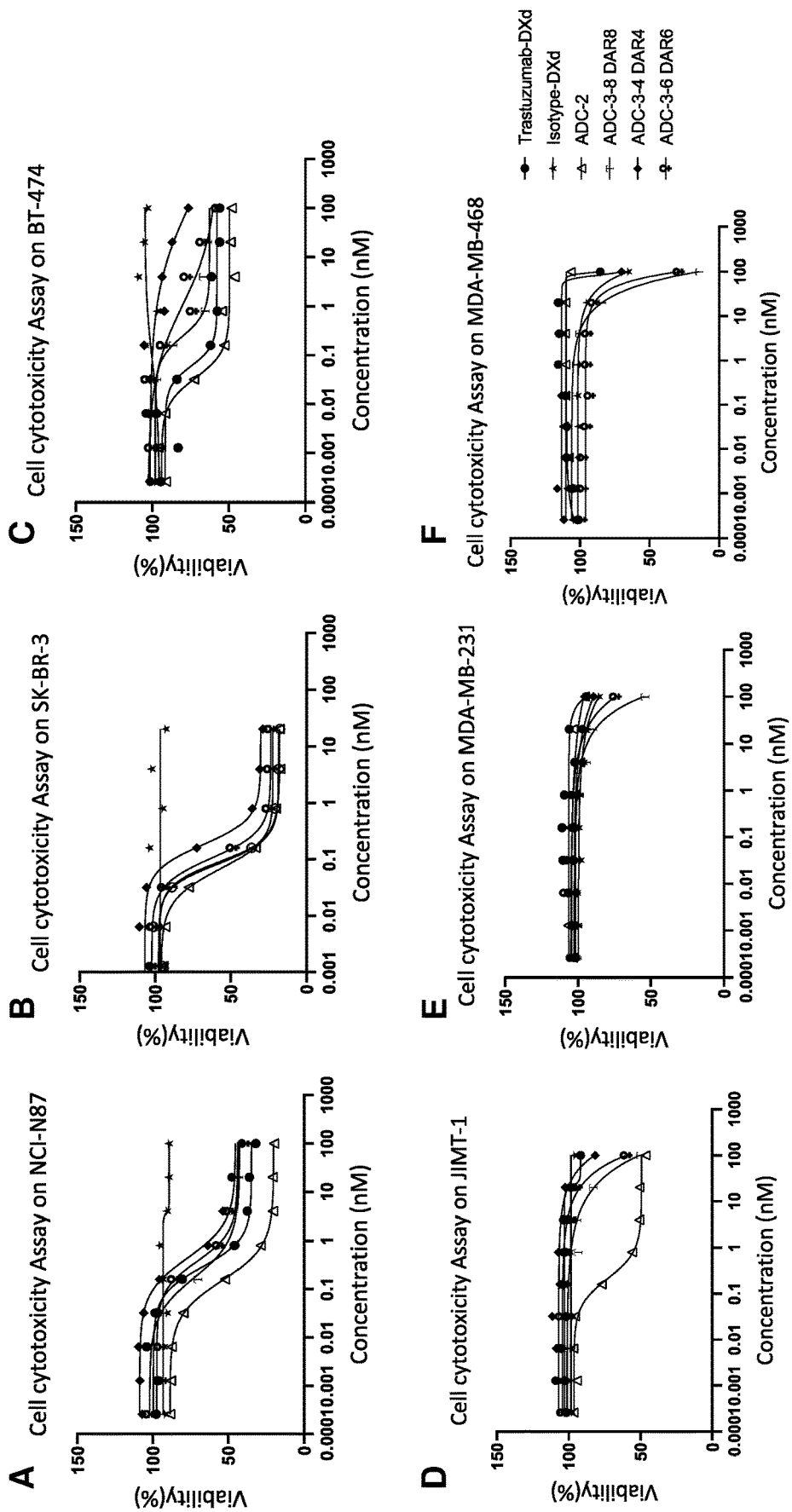
FIG. 4A shows cytotoxicity of HER2 antibody drug conjugates with a drug to antibody ratio of 4 (ADC-3-4), 6 (ADC-3-6), and 8 (ADC-3-8) in NCI-N87 cells.
FIG. 4B shows cytotoxicity of HER2 antibody drug conjugates with a drug to antibody ratio of 4 (ADC-3-4), 6 (ADC-3-6), and 8 (ADC-3-8) in SK-BR-3 cells.
FIG. 4C shows cytotoxicity of HER2 antibody drug conjugates with a drug to antibody ratio of 4 (ADC-3-4), 6 (ADC-3-6), and 8 (ADC-3-8) in BT-474 cells.
FIG. 4D shows cytotoxicity of HER2 antibody drug conjugates with a drug to antibody ratio of 4 (ADC-3-4), 6 (ADC-3-6), and 8 (ADC-3-8) in JIMT-1 cells.
FIG. 4E shows cytotoxicity of HER2 antibody drug conjugates with a drug to antibody ratio of 4 (ADC-3-4), 6 (ADC-3-6), and 8 (ADC-3-8) in MDA-MB-231 cells.
FIG. 4F shows cytotoxicity of HER2 antibody drug conjugates with a drug to antibody ratio of 4 (ADC-3-4), 6 (ADC-3-6), and 8 (ADC-3-8) in MDA-MB-468 cells.

The following description sets forth exemplary embodiments of the present technology. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named.

The prefix "$C_{u-v}$" indicates that the following group has from u to v carbon atoms. For example, "$C_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_{1-20}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e. —(CH$_2$)$_3$CH$_3$), sec-butyl (i.e. —CH(CH$_3$)CH$_2$CH$_3$), isobutyl (i.e. —CH$_2$CH(CH$_3$)$_2$) and tert-butyl (i.e. —C(CH$_3$)$_3$); and "propyl" includes n-propyl (i.e. —(CH$_2$)$_2$CH$_3$) and isopropyl (i.e. —CH(CH$_3$)$_2$).

"Alkenyl" refers to an alkyl group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$ alkenyl). Examples of alkenyl groups include ethenyl, propenyl, butadienyl (including 1,2-butadienyl and 1,3-butadienyl).

"Alkynyl" refers to an alkyl group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term "alkynyl" also includes those groups having one triple bond and one double bond.

"Alkoxy" refers to the group "alkyl-O—". Examples of alkoxy groups include methoxy, ethoxy, n-propoxy, iso-propoxy, n-butoxy, tert-butoxy, sec-butoxy, n-pentoxy, n-hexoxy, and 1,2-dimethylbutoxy.

"Haloalkyl" refers to an unbranched or branched alkyl group as defined above, wherein one or more hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include difluoromethyl (—CHF$_2$) and trifluoromethyl (—CF$_3$).

"Haloalkoxy" refers to an alkoxy group as defined above, wherein one or more hydrogen atoms are replaced by a halogen.

"Alkylthio" refers to the group "alkyl-S—".

"Acyl" refers to a group —C(O)R, wherein R is hydrogen, alkyl, cycloalkyl, heterocyclyl, aryl, heteroalkyl, or heteroaryl; each of which may be optionally substituted, as defined herein. Examples of acyl include formyl, acetyl, cylcohexylcarbonyl, cyclohexylmethyl-carbonyl, and benzoyl.

"Amido" refers to both a "C-amido" group which refers to the group —C(O)NR$^y$R$^z$ and an "N-amido" group which refers to the group —NR$^y$C(O)R$^z$, wherein R$^y$ and R$^z$ are independently selected from the group consisting of hydrogen, alkyl, aryl, haloalkyl, or heteroaryl; each of which may be optionally substituted.

"Amino" refers to the group —NR$^y$R$^z$ wherein R$^y$ and R$^z$ are independently selected from the group consisting of hydrogen, alkyl, haloalkyl, aryl, or heteroaryl; each of which may be optionally substituted.

"Aryl" refers to an aromatic carbocyclic group having a single ring (e.g. monocyclic) or multiple rings (e.g. bicyclic or tricyclic) including fused systems. As used herein, aryl has 6 to 20 ring carbon atoms (i.e., $C_{6-20}$ aryl), 6 to 12 carbon ring atoms (i.e., $C_{6-12}$ aryl), or 6 to 10 carbon ring atoms (i.e., $C_{6-10}$ aryl). Examples of aryl groups include phenyl, naphthyl, fluorenyl, and anthryl. Aryl, however, does not encompass or overlap in any way with heteroaryl defined below. If one or more aryl groups are fused with a heteroaryl, the resulting ring system is heteroaryl. If one or more aryl groups are fused with a heterocyclyl, the resulting ring system is heterocyclyl.

"Carbamoyl" refers to both an "O-carbamoyl" group which refers to the group —O—C(O)NR$^y$R$^z$ and an "N-carbamoyl" group which refers to the group —NR$^y$C(O)OR$^z$, wherein R$^y$ and R$^z$ are independently selected from the group consisting of hydrogen, alkyl, aryl, haloalkyl, or heteroaryl; each of which may be optionally substituted.

"Carboxyl ester" refers to both —OC(O)R and —C(O)OR, wherein R is hydrogen, alkyl, cycloalkyl, heterocyclyl, aryl, heteroalkyl, or heteroaryl; each of which may be optionally substituted, as defined herein.

"Cycloalkyl" refers to a saturated or partially unsaturated cyclic alkyl group having a single ring or multiple rings including fused, bridged, and spiro ring systems. The term "cycloalkyl" includes cycloalkenyl groups (i.e. the cyclic group having at least one double bond). As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Examples of cycloalkyl groups include cyclopropyl, cyclobutyl, cyclopentyl, and cyclohexyl.

"Imino" refers to a group —C(NR)R, wherein each R is independently alkyl, cycloalkyl, heterocyclyl, aryl, heteroalkyl, or heteroaryl; each of which may be optionally substituted, as defined herein.

"Halogen" or "halo" includes fluoro, chloro, bromo, and iodo.

"Heteroalkyl" refers to an alkyl group in which one or more of the carbon atoms (and any associated hydrogen atoms) are each independently replaced with the same or different heteroatomic group (e.g., a $C_2$ heteroalkyl group has one carbon atom and one heteroatom). The term "heteroalkyl" includes unbranched or branched saturated chain having carbon and heteroatoms. By way of example, 1, 2 or 3 carbon atoms may be independently replaced with the same or different heteroatomic group.

Heteroatomic groups include, but are not limited to, —NR—, —O—, —S—, —S(O)—, —S(O)$_2$—, and the like, where R is hydrogen, alkyl, aryl, cycloalkyl, heteroalkyl, heteroaryl or heterocyclyl, each of which may be optionally substituted. Examples of heteroalkyl groups include —OCH$_3$, —CH$_2$OCH$_3$, —SCH$_3$, —CH$_2$SCH$_3$, —NRCH$_3$, and —CH$_2$NRCH$_3$, where R is hydrogen, alkyl, aryl, arylalkyl, heteroalkyl, or heteroaryl, each of which may be optionally substituted. As used herein, heteroalkyl include 1 to 10 carbon atoms, 1 to 8 carbon atoms, or 1 to 4 carbon atoms; and 1 to 3 heteroatoms, 1 to 2 heteroatoms, or 1 heteroatom.

"Heteroalkylene" refers to a divalent heteroalkyl group. "Heteroalkylene" groups must have at least one carbon and at least one heteroatomic group within the chain. The term "heteroalkylene" includes unbranched or branched saturated chain having carbon and heteroatoms. By way of example, 1, 2 or 3 carbon atoms may be independently replaced with the same or different heteroatomic group. Heteroatomic groups include, but are not limited to, —NR—, —O—, —S—, —S(O)—, —S(O)$_2$—, and the like, wherein R is hydrogen, alkyl, alkenyl, alkynyl, cycloalkyl, heterocyclyl, aryl, heteroalkyl or heteroaryl; each of which may be optionally substituted, as defined herein. Examples of heteroalkylene groups include, e.g., —CH$_2$OCH$_2$—, —CH(CH$_3$)OCH$_2$—, —CH$_2$CH$_2$OCH$_2$—, —OCH$_2$—, —CH(CH$_3$)O—, —CH$_2$CH$_2$O—, —CH$_2$CH$_2$OCH$_2$CH$_2$OCH$_2$—, —CH$_2$CH$_2$OCH$_2$CH$_2$O—, —CH$_2$SCH$_2$—, —CH(CH$_3$)SCH$_2$—, —CH$_2$CH$_2$SCH$_2$—, —CH$_2$CH$_2$SCH$_2$CH$_2$SCH$_2$—, —SCH$_2$—, —CH(CH$_3$)S—, —CH$_2$CH$_2$S—, —CH$_2$CH$_2$SCH$_2$CH$_2$S—, —CH$_2$S(O)$_2$CH$_2$—, —CH(CH$_3$)S(O)$_2$CH$_2$—, —CH$_2$CH$_2$S(O)$_2$CH$_2$—, —CH$_2$CH$_2$S(O)$_2$CH$_2$CH$_2$OCH$_2$—, —CH$_2$NRCH$_2$—, —CH(CH$_3$)NRCH$_2$—, —CH$_2$CH$_2$NRCH$_2$—, —CH$_2$CH$_2$NRCH$_2$CH$_2$NRCH$_2$—, etc., where each R is independently hydrogen, alkyl, alkenyl, alkynyl, cycloalkyl, heterocyclyl, aryl, heteroalkyl, or heteroaryl; each of which may be optionally substituted, as defined herein). As used herein, heteroalkylene includes 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to an aromatic group having a single ring, multiple rings, or multiple fused rings, with one or more ring heteroatoms independently selected from nitrogen, oxygen, and sulfur. As used herein, heteroaryl includes 1 to 20 ring carbon atoms (i.e., $C_{1-20}$ heteroaryl), 3 to 12 ring carbon atoms (i.e., $C_{3-12}$ heteroaryl), or 3 to 8 carbon ring atoms (i.e., $C_{3-8}$ heteroaryl); and 1 to 5 heteroatoms, 1 to 4 heteroatoms, 1 to 3 ring heteroatoms, 1 to 2 ring heteroatoms, or 1 ring heteroatom independently selected from nitrogen, oxygen, and sulfur. Examples of heteroaryl groups include pyrimidinyl, purinyl, pyridyl, pyridazinyl, benzothiazolyl, and pyrazolyl. Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl, and imidazo[1,5-a]pyridinyl, where the heteroaryl can be bound via either ring of the fused system. Any aromatic ring, having a single or multiple fused rings, containing at least one heteroatom, is considered a heteroaryl regardless of the attachment to the remainder of the molecule (i.e., through any one of the fused rings). Heteroaryl does not encompass or overlap with aryl as defined above.

"Heterocyclyl" refers to a saturated or unsaturated cyclic alkyl group, with one or more ring heteroatoms independently selected from nitrogen, oxygen and sulfur. The term "heterocyclyl" includes heterocycloalkenyl groups (i.e. the heterocyclyl group having at least one double bond), bridged-heterocyclyl groups, fused-heterocyclyl groups, and spiro-heterocyclyl groups. A heterocyclyl may be a single ring or multiple rings wherein the multiple rings may be fused, bridged, or spiro. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. As used herein, heterocyclyl has 2 to 20 ring carbon atoms (i.e., $C_{2-20}$ heterocyclyl), 2 to 12 ring carbon atoms (i.e., $C_{2-12}$ heterocyclyl), 2 to 10 ring carbon atoms (i.e., $C_{2-10}$ heterocyclyl), 2 to 8 ring carbon atoms (i.e., $C_{2-8}$ heterocyclyl), 3 to 12 ring carbon atoms (i.e., $C_{3-12}$ heterocyclyl), 3 to 8 ring carbon atoms (i.e., $C_{3-8}$ heterocyclyl), or 3 to 6 ring carbon atoms (i.e., $C_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. Examples of heterocyclyl groups include pyrrolidinyl, piperidinyl, piperazinyl, oxetanyl, dioxolanyl, azetidinyl, and morpholinyl. As used herein, the term "bridged-heterocyclyl" refers to a four- to ten-membered cyclic moiety connected at two non-adjacent atoms of the heterocyclyl with one or more (e.g., 1 or 2) four- to ten-membered cyclic moiety having at least one heteroatom where each heteroatom is independently selected from nitrogen, oxygen, and sulfur.

As used herein, bridged-heterocyclyl includes bicyclic and tricyclic ring systems. Also used herein, the term "spiro-heterocyclyl" refers to a ring system in which a three- to ten-membered heterocyclyl has one or more additional ring, wherein the one or more additional ring is three- to ten-membered cycloalkyl or three- to ten-membered heterocyclyl, where a single atom of the one or more additional ring is also an atom of the three- to ten-membered heterocyclyl. Examples of the spiro-heterocyclyl rings include bicyclic and tricyclic ring systems, such as 2-oxa-7-azaspiro [3.5]nonanyl, 2-oxa-6-azaspiro[3.4]octanyl, and 6-oxa-1-azaspiro[3.3]heptanyl. Examples of the fused-heterocyclyl rings include, but are not limited to, 1,2,3,4-tetrahydroisoquinolinyl, 4,5,6,7-tetrahydrothieno[2,3-c]pyridinyl, indolinyl, and isoindolinyl, where the heterocyclyl can be bound via either ring of the fused system.

"Sulfonyl" refers to the group —S(O)$_2$R, where R is alkyl, haloalkyl, heterocyclyl, cycloalkyl, heteroaryl, or aryl. Examples of sulfonyl are methylsulfonyl, ethylsulfonyl, phenylsulfonyl, and toluenesulfonyl.

"Alkylsulfonyl" refers to the group —S(O)$_2$, where R is alkyl.

"Alkylsulfinyl" refers to the group —S(O)R, where R is alkyl.

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g. arylalkyl, the last mentioned group contains the atom by which the moiety is attached to the rest of the molecule.

The terms "optional" or "optionally" means that the subsequently described event or circumstance may or may not occur, and that the description includes instances where said event or circumstance occurs and instances in which it does not. Also, the term "optionally substituted" refers to any one or more hydrogen atoms on the designated atom or group may or may not be replaced by a moiety other than hydrogen.

As used herein, the term "compound," is meant to include all stereoisomers, geometric isomers, tautomers, and isotopes of the structures depicted. Compounds herein identified by name or structure as one particular tautomeric form are intended to include other tautomeric forms unless otherwise specified.

Some of the compounds exist as tautomers. Tautomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

Any formula or structure given herein, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure, for example those into which radioactive isotopes such as $^3$H, $^{13}$C and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes "deuterated analogs" of compounds of Formula I in which from 1 to n hydrogens attached to a carbon atom is/are replaced by deuterium, in which n is the number of hydrogens in the molecule. Such compounds exhibit increased resistance to metabolism and are thus useful for increasing the half-life of any compound of Formula I when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino and/or carboxyl groups or groups similar thereto.

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include, e.g., hydrochloric acid, hydrobromic acid, sulfuric acid, nitric acid, phosphoric acid and the like.

Salts derived from organic acids include, e.g., acetic acid, propionic acid, gluconic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Likewise, pharmaceutically acceptable base addition salts can be prepared from inorganic and organic bases. Salts derived from inorganic bases include, by way of example only, sodium, potassium, lithium, aluminum, ammonium, calcium, and magnesium salts.

Salts derived from organic bases include, but are not limited to, salts of $NH_3$, or primary, secondary, tertiary amines, such as salts derived from a N-containing heterocycle, a N-containing heteroaryl, or derived from an amine of formula $N(R^N)_3$ (e.g., $HN^+(R^N)_3$ or $(alkyl)N^+(R^N)_3$) where each $R^N$ is independently hydrogen, alkyl, alkenyl, alkynyl, haloalkyl, cycloalkyl, heterocyclyl, aryl, or heteroaryl, wherein each is optionally substituted, such as by one or more (e.g., 1-5 or 1-3) substituents (e.g., halo, cyano, hydroxy, amino, alkyl, alkenyl, alkynyl, haloalkyl, alkoxy, or haloalkoxy). Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, haloalkoxy, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl)substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. Unless specified otherwise, where a group is described as optionally substituted, any substituents of the group are themselves unsubstituted. For example, in some embodiments, the term "substituted alkyl" refers to an alkyl group having one or more substituents including hydroxyl, halo, alkoxy, cycloalkyl, heterocyclyl, aryl, and heteroaryl. In other embodiments, the one or more substituents may be further substituted with halo, alkyl, haloalkyl, hydroxyl, alkoxy, cycloalkyl, heterocyclyl, aryl, or heteroaryl, each of which is substituted. In other embodiments, the substituents may be further substituted with halo, alkyl, haloalkyl, alkoxy, hydroxyl, cycloalkyl, heterocyclyl, aryl, or heteroaryl, each of which is unsubstituted.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The term "pharmaceutically acceptable" as used herein indicates that the compound, or salt or composition thereof is compatible chemically and/or toxicologically with the other ingredients comprising a formulation and/or the subject being treated therewith.

The term "administration" or "administering" refers to a method of giving a dosage of a compound or pharmaceutical composition to a vertebrate or invertebrate, including a mammal, a bird, a fish, or an amphibian. The method of administration can vary depending on various factors, e.g., the components of the pharmaceutical composition, the site of the disease, and the severity of the disease.

The terms "effective amount" or "effective dosage" or "pharmaceutically effective amount" or "therapeutically effective amount," as used herein, refer to a sufficient amount of a chemical entity (e.g., a compound of Formula I, or a pharmaceutically acceptable salt or solvate thereof) being administered which will relieve to some extent one or more of the symptoms of the disease or condition being treated, and can include curing the disease. "Curing" means that the symptoms of active disease are eliminated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is determined using any suitable technique, such as a dose escalation study. In some embodiments, a "therapeutically effective amount" of a compound as provided herein refers to an amount of the compound that is effective as a monotherapy or combination therapy.

The term "excipient" or "pharmaceutically acceptable excipient" means a pharmaceutically-acceptable material, composition, or vehicle, such as a liquid or solid filler, diluent, carrier, solvent, or encapsulating material. In some embodiments, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., Remington: The Science and Practice of Pharmacy, 21st ed.; Lippincott Williams & Wilkins: Philadelphia, P A, 2005; Handbook of Pharmaceutical Excipients, 6th ed.; Rowe et al., Eds.; The Pharmaceutical Press and the American Pharmaceutical Association: 2009; Handbook of Pharmaceutical Additives, 3rd ed.; Ash and Ash Eds.; Gower Publishing Company: 2007; Pharmaceutical Preformulation and Formulation, 2nd ed.; Gibson Ed.; CRC Press LLC: Boca Raton, F L, 2009.

The term "pharmaceutical composition" refers to a mixture of a compound of Formula I, or a pharmaceutically acceptable salt or solvate thereof as provided herein with other chemical components (referred to collectively herein as "excipients"), such as carriers, stabilizers, diluents, dispersing agents, suspending agents, and/or thickening agents. The pharmaceutical composition facilitates administration of the compound to an organism. Multiple techniques of administering a compound exist in the art including, but not limited to, rectal, oral, intravenous, aerosol, parenteral, ophthalmic, pulmonary, and topical administration.

Compounds

In one aspect, provided herein is a compound of Formula I:

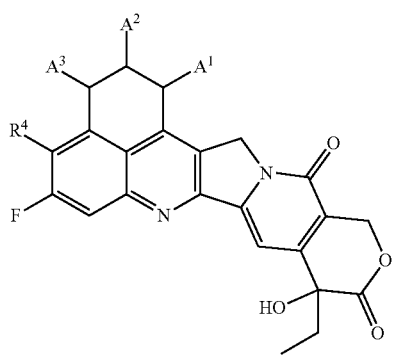

or stereoisomer or pharmaceutically acceptable salt thereof, wherein:

$A^1$ is —$NHR^1$, where $R^1$ is hydrogen, —$C(O)R^5$, —$C_6$ aryl-$C_{1-6}$ alkyl-$NH_2$, or —$C_6$ aryl-$C_{1-6}$ alkyl-NHC(O)$R^5$; and $A^2$ and $A^3$ are both hydrogen; or $A^2$ is —$NHR^2$, where $R^2$ is hydrogen, —$C(O)R^5$, —$C_6$ aryl-$C_{1-6}$ alkyl-$NH_2$, or —$C_6$ aryl-$C_{1-6}$ alkyl-NHC(O)$R^5$; and $A^1$ and $A^3$ are both hydrogen; or $A^3$ is —$NHR^3$, where $R^3$ is hydrogen, —$C(O)R^5$, —$C_6$ aryl-$C_{1-6}$ alkyl-$NH_2$, or —$C_6$ aryl-$C_{1-6}$ alkyl-NHC(O)$R^5$; and $A^1$ and $A^2$ are both hydrogen;

$R^4$ is —$C_{1-6}$ alkyl; provided that when $A^1$ is —$NHR^1$, then $R^4$ is other than methyl;

$R^5$ is -L-$R^6$;

L is a linker moiety; and $R^6$ is hydrogen or heterocyclyl, wherein said heterocyclyl is optionally covalently linked to an antibody or antigen-binding fragment.

In some embodiments, $A^1$ is —$NHR^1$, where $R^1$ is hydrogen, —$C(O)R^5$, —$C_6$ aryl-$C_{1-6}$ alkyl-$NH_2$, or —$C_6$ aryl-$C_{1-6}$ alkyl-NHC(O)$R^5$; and $A^2$ and $A^3$ are both hydrogen. Accordingly, in some embodiments, provided is a compound of Formula II:

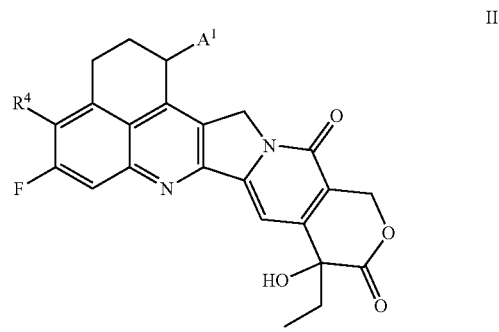

or stereoisomer or pharmaceutically acceptable salt thereof, wherein $R^4$ is —$C_{2-6}$ alkyl, and $A^1$ is independently as defined herein.

In some embodiments, $A^1$ is —$NH_2$; and $A^2$ and $A^3$ are both hydrogen.

In some embodiments, $A^1$ is —NH—$C(O)R^5$; and $A^2$ and $A^3$ are both hydrogen.

In some embodiments, $A^1$ is —NH—$C_6$ aryl-$C_{1-6}$ alkyl-$NH_2$; and $A^2$ and $A^3$ are both hydrogen. In some embodiments, $A^1$ is —NH—$C_6$ aryl-$CH_2$—$NH_2$; and $A^2$ and $A^3$ are both hydrogen.

In some embodiments, $A^1$ is —NH—$C_6$ aryl-$C_{1-6}$ alkyl-NHC(O)$R^5$; and $A^2$ and $A^3$ are both hydrogen. In some embodiments, $A^1$ is —NH—$C_6$ aryl-$CH_2$—NHC(O)$R^5$; and $A^2$ and $A^3$ are both hydrogen.

In some embodiments, $A^2$ is —$NHR^2$, where $R^2$ is hydrogen, —$C(O)R^5$, —$C_6$ aryl-$C_{1-6}$ alkyl-$NH_2$, or —$C_6$ aryl-$C_{1-6}$ alkyl-NHC(O)$R^5$; and $A^1$ and $A^3$ are both hydrogen. Accordingly, in some embodiments, provided is a compound of Formula III:

III

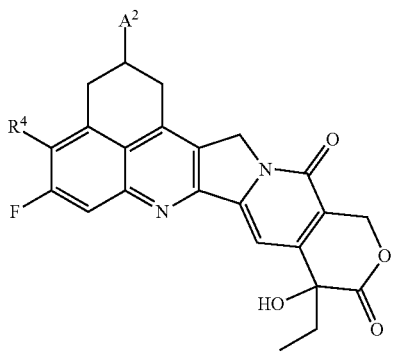

or stereoisomer or pharmaceutically acceptable salt thereof, wherein $A^2$ and $R^4$ are each independently as defined herein.

In some embodiments, $A^2$ is —$NH_2$; and $A^1$ and $A^3$ are both hydrogen.

In some embodiments, $A^2$ is —NH—C(O)$R^5$; and $A^1$ and $A^3$ are both hydrogen.

In some embodiments, $A^2$ is —NH—$C_6$ aryl-$C_{1-6}$ alkyl-$NH_2$; and $A^1$ and $A^3$ are both hydrogen. In some embodiments, $A^2$ is —NH—$C_6$ aryl-$CH_2$—$NH_2$; and $A^1$ and $A^3$ are both hydrogen.

In some embodiments, $A^2$ is —NH—$C_6$ aryl-$C_{1-6}$ alkyl-NHC(O)$R^5$; and $A^1$ and $A^3$ are both hydrogen. In some embodiments, $A^2$ is —NH—$C_6$ aryl-$CH_2$—NHC(O)$R^5$; and $A^1$ and $A^3$ are both hydrogen.

In some embodiments, $A^3$ is —$NHR^3$, where $R^3$ is hydrogen, —C(O)$R^5$, —$C_6$ aryl-$C_{1-6}$ alkyl-$NH_2$, or —$C_6$ aryl-$C_{1-6}$ alkyl-NHC(O)$R^5$; and $A^1$ and $A^2$ are both hydrogen. Accordingly, in some embodiments, provided is a compound of Formula IV:

IV

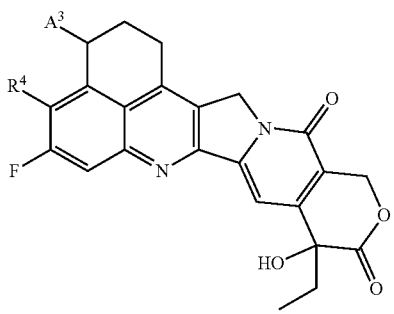

or stereoisomer or pharmaceutically acceptable salt thereof, wherein $A^3$ and $R^4$ are each independently as defined herein.

In some embodiments, $A^3$ is —$NH_2$; and $A^1$ and $A^2$ are both hydrogen.

In some embodiments, $A^3$ is —NH—C(O)$R^5$; and $A^1$ and $A^2$ are both hydrogen.

In some embodiments, $A^3$ is —NH—$C_6$ aryl-$C_{1-6}$ alkyl-$NH_2$; and $A^1$ and $A^2$ are both hydrogen. In some embodiments, $A^3$ is —NH—$C_6$ aryl-$CH_2$—$NH_2$; and $A^1$ and $A^2$ are both hydrogen.

In some embodiments, $A^3$ is —NH—$C_6$ aryl-$C_{1-6}$ alkyl-NHC(O)$R^5$; and $A^1$ and $A^2$ are both hydrogen. In some embodiments, $A^3$ is —NH—$C_6$ aryl-$CH_2$—NHC(O)$R^5$; and $A^1$ and $A^2$ are both hydrogen.

In some embodiments, $R^4$ is methyl, ethyl or isopropyl. In some embodiments, $R^4$ is ethyl or isopropyl. In some embodiments, $R^4$ is methyl. In some embodiments, $R^4$ is ethyl. In some embodiments, $R^4$ is isopropyl.

In some embodiments, provided is a compound of Formula IIA:

IIA

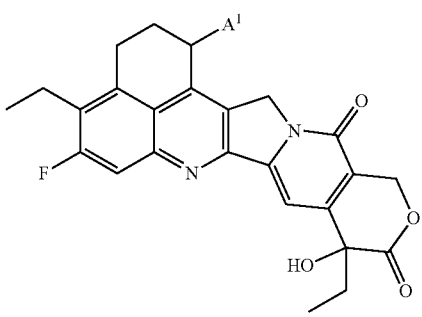

or stereoisomer or pharmaceutically acceptable salt thereof, wherein $A^1$ is independently as defined herein.

In some embodiments, provided is a compound of Formula IIB:

IIB

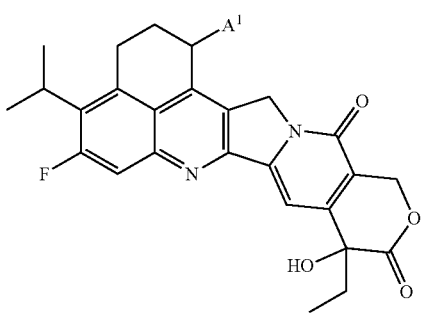

or stereoisomer or pharmaceutically acceptable salt thereof, wherein $A^1$ is independently as defined herein.

In some embodiments, provided is a compound of Formula IIIA:

IIIA

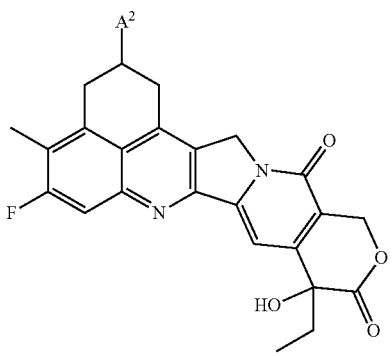

or stereoisomer or pharmaceutically acceptable salt thereof, wherein $A^2$ is independently as defined herein.

In some embodiments, provided is a compound of Formula IVA:

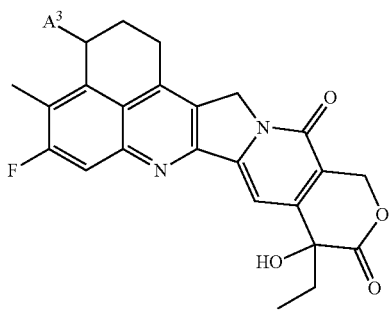

IVA or stereoisomer or pharmaceutically acceptable salt thereof, wherein $A^3$ is independently as defined herein.

In some embodiments, provided is a compound of Formula IIC:

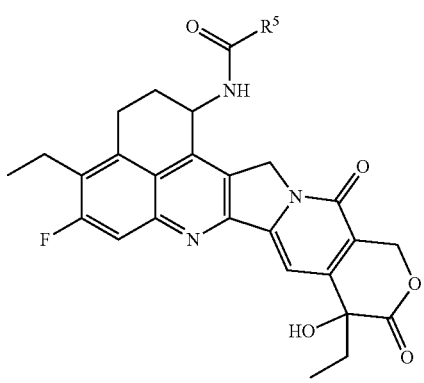

IIC or stereoisomer or pharmaceutically acceptable salt thereof, wherein $R^5$ is independently as defined herein.

In some embodiments, provided is a compound of Formula IID:

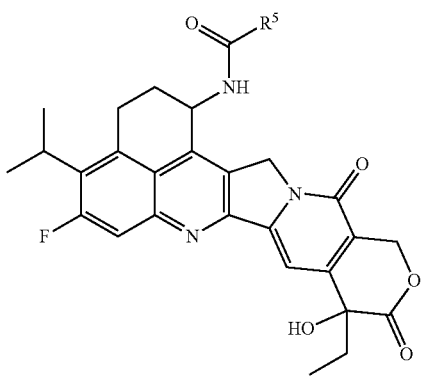

IID or stereoisomer or pharmaceutically acceptable salt thereof, wherein $R^5$ is independently as defined herein.

In some embodiments, provided is a compound of Formula IIIB:

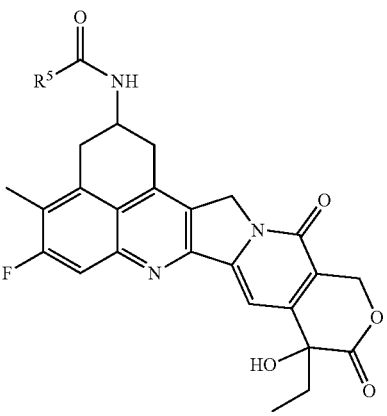

IIIB or stereoisomer or pharmaceutically acceptable salt thereof, wherein $R^5$ is independently as defined herein.

In some embodiments, provided is a compound of Formula IVB:

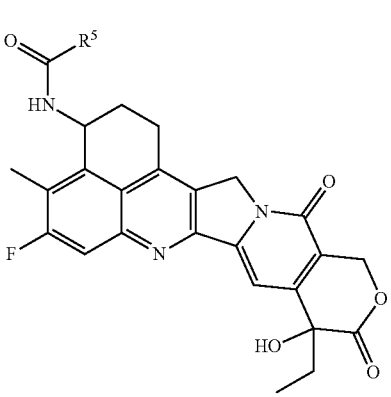

IVB or stereoisomer or pharmaceutically acceptable salt thereof, wherein $R^5$ is independently as defined herein.

In some embodiments, when $R^1$, $R^2$, or $R^3$ is other than hydrogen, the compound comprises a linking moiety, L, which covalently links $R^6$ to the remainder of the compound.

In some embodiments, L is a non-cleavable linker.

In some embodiments, L is a cleavable linker.

In some embodiments, L comprises 1 to 100 linking atoms, from 1 to 50 linking atoms, or from 5 to 50 linking atoms, or from 10 to 50 linking atoms, or from 1 to 40 linking atoms, or from 1 to 30 linking atoms, or from 1 to 20 linking atoms, or from 5 to 30 linking atoms, or from 10 to 30 linking atoms, or from 5 to 40 linking atoms, or from 5 to 50 linking atoms, or from 10 to 50 linking atoms, or from 20 to 50 linking atoms, or from 20 to 40 linking atoms, or from 20 to 30 linking atoms.

In some embodiments, L comprises one or more chain heteroatoms and one or more alkylene, alkenylene, alkynylene, arylene, heteroarylene, cycloalkylene, or heterocycloalkylene moieties; wherein each alkylene, alkenylene, alkynylene, arylene, heteroarylene, cycloalkylene, or heterocycloalkylene moiety, may be independently optionally substituted with one to five substituents independently selected from oxo, halo, $C_{1-4}$ alkyl, $C_{1-4}$ alkoxy, $C_{1-4}$ haloalkyl, and benzyl.

In some embodiments, L is an alkylene linker optionally comprising one or more —O—, —S—, amine, ester, amide, carbamate, carbonate, thio-succinimide, or ketone functional groups.

In some embodiments, L comprises one or more amino acids. In some embodiments, L comprises one or more linear or branched, natural or unnatural amino acids. In some embodiments, L comprises a polypeptide.

In some embodiments, L comprises one or more polyethylene glycol unit (e.g., PEG having an average molecular weight of from 300 g/mol to 10,000 g/mol).

In some embodiments, L is -$L^1$-$(AA)_n$-$L^2$-$R^6$, where each $L^1$, AA, n, $L^2$, and $R^6$ are independently as defined herein.

In some embodiments, $L^1$ is $C_{1-20}$ alkylene or $C_{2-20}$ heteroalkylene;
  n is 0, 1, 2, 3, 4, 5, or 6;
  each AA is independently an amino acid; and
  $L^2$ is $C_{1-40}$ alkylene or $C_{2-40}$ heteroalkylene, wherein the $C_{1-40}$ alkylene or $C_{2-40}$ heteroalkylene optionally comprises a phenylene within the $C_{1-40}$ alkylene or $C_{2-40}$ heteroalkylene chain, and the $C_{1-40}$ alkylene or $C_{2-40}$ heteroalkylene is optionally substituted with one or more (e.g., one or two) oxo.

In some embodiments, $L^1$ is $C_{1-20}$ alkylene or $C_{2-20}$ heteroalkylene;
  n is 0, 1, 2, 3, 4, 5, or 6;
  each AA is independently an amino acid; and
  $L^2$ is $C_{1-40}$ alkylene or $C_{2-40}$ heteroalkylene, wherein the $C_{1-40}$ alkylene or $C_{2-40}$ heteroalkylene is optionally substituted with one or more (e.g., one or two) oxo.

In some embodiments, n is 0. In some embodiments, n is 1, 2, 3, 4, 5, 6, or 7. In some embodiments, n is 2, 3, 4, 5, 6, or 7. In some embodiments, n is 1. In some embodiments, n is 2. In some embodiments, n is 3. In some embodiments, n is 4. In some embodiments, n is 5. In some embodiments, n is 6. In some embodiments, n is 7.

In some embodiments, $L^1$ is $C_{1-20}$ alkylene. In some embodiments, $L^1$ is $C_{1-10}$ alkylene. In some embodiments, $L^1$ is $C_{2-6}$ alkylene.

In some embodiments, $L^1$ is $C_{2-20}$ heteroalkylene. In some embodiments, $L^1$ is $C_{2-10}$ heteroalkylene. In some embodiments, $L^1$ is $C_{2-6}$ heteroalkylene.

In some embodiments, $L^1$ is —$(CH_2)_p$—$X^1$—$(CH_2)_q$—$X^2$—* or —$X^1$—$(CH_2)_p$-phenylene-$(CH_2)_q$—$X^2$—*; wherein the * bond is attached to the -$(AA)_n$-$L^2$-$R^6$; and
  $X^1$ is a bond, —O—, —S—, or —NH—;
  $X^2$ is a bond, —O—, —S—, or —NH—;
  p is 1, 2, 3, or 4; and
  q is 1, 2, 3, or 4.

In some embodiments, $L^1$ is —$X^1$—$(CH_2)_p$-phenylene-$(CH_2)_q$—$X^2$—*; wherein the * bond is attached to the -$(AA)_n$-$L^2$-$R^6$; and
  $X^1$ is a bond, —O—, —S—, or —NH—;
  $X^2$ is a bond, —O—, —S—, or —NH—;
  p is 1, 2, 3, or 4; and
  q is 1, 2, 3, or 4.

In some embodiments, $L^1$ is —$(CH_2)_p$—$X^1$—$(CH_2)_q$—$X^2$—*; wherein the * bond is attached to the -$(AA)_n$-$L^2$-$R^6$; and
  $X^1$ is a bond, —O—, —S—, or —NH—;
  $X^2$ is a bond, —O—, —S—, or —NH—;
  p is 1, 2, 3, or 4; and
  q is 1, 2, 3, or 4.

In some embodiments, $L^1$ is —$CH_2$—$X^1$—$CH_2$—$X^2$—*. In some embodiments, $L^1$ is —$(CH_2)_2$—$X^1$—$CH_2$—$X^2$—*. In some embodiments, $L^1$ is —$(CH_2)_3$—$X^1$—$CH_2$—$X^2$—*. In some embodiments, $L^1$ is —$(CH_2)_4$—$X^1$—$CH_2$—$X^2$—*.

In some embodiments, $L^1$ is —$CH_2$—$X^1$—$(CH_2)_2$—$X^2$—*. In some embodiments, $L^1$ is —$(CH_2)_2$—$X^1$—$(CH_2)_2$—$X^2$—*. In some embodiments, $L^1$ is —$(CH_2)_3$—$X^1$—$(CH_2)_2$—$X^2$—*. In some embodiments, $L^1$ is —$(CH_2)_4$—$X^1$—$(CH_2)_2$—$X^2$—*.

In some embodiments, $L^1$ is —$CH_2$—$X^1$—$(CH_2)_3$—$X^2$—*. In some embodiments, $L^1$ is —$(CH_2)_2$—$X^1$—$(CH_2)_3$—$X^2$—*. In some embodiments, $L^1$ is —$(CH_2)_3$—$X^1$—$(CH_2)_3$—$X^2$—*. In some embodiments, $L^1$ is —$(CH_2)_4$—$X^1$—$(CH_2)_3$—$X^2$—*.

In some embodiments, $L^1$ is —$CH_2$—$X^1$—$(CH_2)_4$—$X^2$—*. In some embodiments, $L^1$ is —$(CH_2)_2$—$X^1$—$(CH_2)_4$—$X^2$—*. In some embodiments, $L^1$ is —$(CH_2)_3$—$X^1$—$(CH_2)_4$—$X^2$—*. In some embodiments, $L^1$ is —$(CH_2)_4$—$X^1$—$(CH_2)_4$—$X^2$—*.

In some embodiments, $X^1$ is a bond. In some embodiments, $X^1$ is —O—. In some embodiments, $X^1$ is —S—. In some embodiments, $X^1$ is —NH—.

In some embodiments, $X^2$ is a bond. In some embodiments, $X^2$ is —O—. In some embodiments, $X^2$ is —S—. In some embodiments, $X^2$ is —NH—.

In some embodiments, $L^1$ is —$CH_2$—$X^1$—$CH_2$—NH—*. In some embodiments, $L^1$ is —$(CH_2)_2$—$X^1$—$CH_2$—NH—*. In some embodiments, $L^1$ is —$(CH_2)_3$—$X^1$—$CH_2$—NH—*. In some embodiments, $L^1$ is —$(CH_2)_4$—$X^1$—$CH_2$—NH—*.

In some embodiments, $L^1$ is —$CH_2$—$X^1$—$(CH_2)_2$—NH—*. In some embodiments, $L^1$ is —$(CH_2)_2$—$X^1$—$(CH_2)_2$—NH—*. In some embodiments, $L^1$ is —$(CH_2)_3$—$X^1$—$(CH_2)_2$—NH—*. In some embodiments, $L^1$ is —$(CH_2)_4$—$X^1$—$(CH_2)_2$—NH—*.

In some embodiments, $L^1$ is —$CH_2$—$X^1$—$(CH_2)_3$—NH—*. In some embodiments, $L^1$ is —$(CH_2)_2$—$X^1$—$(CH_2)_3$—NH—*. In some embodiments, $L^1$ is —$(CH_2)_3$—$X^1$—$(CH_2)_3$—NH—*. In some embodiments, $L^1$ is —$(CH_2)_4$—$X^1$—$(CH_2)_3$—NH—*.

In some embodiments, $L^1$ is —$CH_2$—$X^1$—$(CH_2)_4$—NH—*. In some embodiments, $L^1$ is —$(CH_2)_2$—$X^1$—$(CH_2)_4$—NH—*. In some embodiments, $L^1$ is —$(CH_2)_3$—$X^1$—$(CH_2)_4$—NH—*. In some embodiments, $L^1$ is —$(CH_2)_4$—$X^1$—$(CH_2)_4$—NH—*.

In some embodiments, $L^1$ is —$CH_2$—O—$CH_2$—$X^2$—*. In some embodiments, $L^1$ is —$(CH_2)_2$O—$CH_2$—$X^2$—*. In some embodiments, $L^1$ is —$(CH_2)_3$—O—$CH_2$—$X^2$—*. In some embodiments, $L^1$ is —$(CH_2)_4$O—$CH_2$—$X^2$—*.

In some embodiments, $L^1$ is —$CH_2$—O—$(CH_2)_2$—$X^2$—*. In some embodiments, $L^1$ is —$(CH_2)_2$—O—$(CH_2)_2$—$X^2$—*. In some embodiments, $L^1$ is —$(CH_2)_3$—O—$(CH_2)_2$—$X^2$—*. In some embodiments, $L^1$ is —$(CH_2)_4$—O—$(CH_2)_2$—$X^2$—*.

In some embodiments, $L^1$ is —$CH_2$—O—$(CH_2)_3$—$X^2$—*. In some embodiments, $L^1$ is —$(CH_2)_2$—O—$(CH_2)_3$—$X^2$—*. In some embodiments, $L^1$ is —$(CH_2)_3$—O—$(CH_2)_3$—$X^2$—*. In some embodiments, $L^1$ is —$(CH_2)_4$—O—$(CH_2)_3$—$X^2$—*.

In some embodiments, $L^1$ is —$CH_2$—O—$(CH_2)_4$—$X^2$—*. In some embodiments, $L^1$ is —$(CH_2)_2$—O—$(CH_2)_4$—$X^2$—*. In some embodiments, $L^1$ is —$(CH_2)_3$—O—$(CH_2)_4$—$X^2$—*. In some embodiments, $L^1$ is —$(CH_2)_4$—O—$(CH_2)_4$—$X^2$—*.

In some embodiments, $L^1$ is

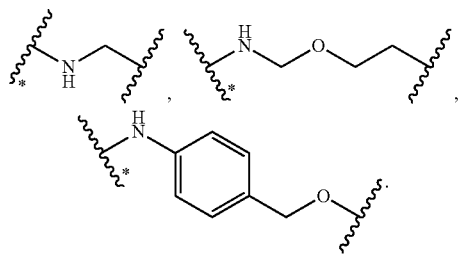

wherein the * bond is attached to the $-(AA)_n-L^2-R^6$.

In some embodiments, $L^1$ is $-(CH_2)_p-O-(CH_2)_q-NH-*$.

In some embodiments, $L^1$ is $-CH_2-O-CH_2-NH-*$. In some embodiments, $L^1$ is $-(CH_2)_2O-CH_2-NH-*$. In some embodiments, $L^1$ is $-(CH_2)_3-O-CH_2-NH-*$. In some embodiments, $L^1$ is $-(CH_2)_4O-CH_2-NH-*$.

In some embodiments, $L^1$ is $-CH_2-O-(CH_2)_2-NH-*$. In some embodiments, $L^1$ is $-(CH_2)_2-O-(CH_2)_2-NH-*$. In some embodiments, $L^1$ is $-(CH_2)_3-O-(CH_2)_2-NH-*$. In some embodiments, $L^1$ is $-(CH_2)_4-O-(CH_2)_2-NH-*$.

In some embodiments, $L^1$ is $-CH_2-O-(CH_2)_3-NH-*$. In some embodiments, $L^1$ is $-(CH_2)_2-O-(CH_2)_3-NH-*$. In some embodiments, $L^1$ is $-(CH_2)_3-O-(CH_2)_3-NH-*$. In some embodiments, $L^1$ is $-(CH_2)_4-O-(CH_2)_3-NH-*$.

In some embodiments, $L^1$ is $-CH_2-O-(CH_2)_4-NH-*$. In some embodiments, $L^1$ is $-(CH_2)_2-O-(CH_2)_4-NH-*$. In some embodiments, $L^1$ is $-(CH_2)_3-O-(CH_2)_4-NH-*$. In some embodiments, $L^1$ is $-(CH_2)_4-O-(CH_2)_4-NH-*$.

In certain embodiments, L comprises more than one sequential amino acid to form a peptide unit of formula $-(AA)_n-$. In certain embodiments, the peptide unit of formula $-(AA)_n-$ consists of 2 to 7 amino acids, where the amino acids are linked by a peptide (i.e., amide) bonding. In certain embodiments, the peptide unit of formula $-(AA)_n-$, the linker $L^1$ is bonded to the AA at its C-terminus, and to the $-L^2-R^6$ moiety at its N-terminus.

The amino acid sequence of the peptide unit $-(AA)_n-$ is not particularly limited, but examples thereof include an L- or a D-amino acid, and can comprise an amino acid having a structure such as β-alanine, ε-aminocaproic acid, γ-aminobutyric acid, an α-amino acid, or a non-natural type amino acid, such as N-methylated amino acid. Specific examples include phenylalanine (Phe; F), tyrosine (Tyr; Y), leucine (Leu; L), glycine (Gly; G), alanine (Ala; A), valine (Val; V), lysine (Lys; K), citrulline (Cit), serine (Ser; S), glutamic acid (Glu; E), and aspartic acid (Asp; D). In certain embodiments, the peptide unit $-(AA)_n-$ comprises one or more (e.g., 2 to 7, or 2 to 5, or 3 to 5, or 4) amino acid residues independently selected from phenylalanine, glycine, valine, lysine, citrulline, serine, glutamic acid, and aspartic acid.

In certain embodiments, $-(AA)_n-$ is selected from -FGG-, -FGGD-, -FGG-(D-)D-, -FGGE-, -GFGG-, -FGGS-, -FGGK-, -GFGGD-, -GGFGG-, -GFGGDD-, -GFGGDK-, -FGGGFGG-, wherein (D-)D refers to D-aspartic acid.

In some embodiments, n is 2, 3, 4, 5, 6, or 7, and each AA is independently selected from Gly and Phe.

In some embodiments, $-(AA)_n-$ is -Gly-Phe-Gly-Gly- (-GFGG-).

In some embodiments, $-(AA)_n-$ is

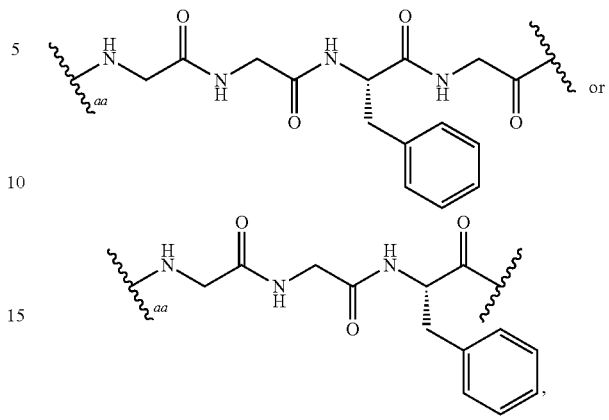

wherein bond aa is attached to $L^2$.

In some embodiments, $-(AA)_n-$ is

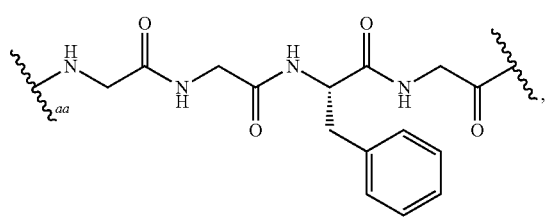 [SMILES: *NCC(=O)NCC(=O)N[C@@H](Cc1ccccc1)C(=O)NCC(*)=O]

wherein bond aa is attached to $L^2$.

In some embodiments, $-(AA)_R-$ is

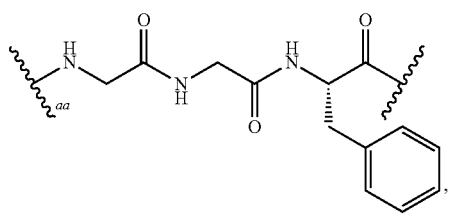 [SMILES: *NCC(=O)NCC(=O)N[C@@H](Cc1ccccc1)C(*)=O]

wherein bond aa is attached to $L^2$.

In some embodiments, $L^2$ is $C_{1-40}$ alkylene optionally substituted with one or more oxo. In some embodiments, $L^2$ is $C_{1-30}$ alkylene optionally substituted with one or more oxo. In some embodiments, $L^2$ is $C_{1-20}$ alkylene optionally substituted with one or more oxo. In some embodiments, $L^2$ is $C_{1-10}$ alkylene optionally substituted with one or more oxo. In some embodiments, $L^2$ is $C_{5-40}$ alkylene optionally substituted with one or more oxo. In some embodiments, $L^2$ is $C_{5-30}$ alkylene optionally substituted with one or more oxo. In some embodiments, $L^2$ is $C_{5-20}$ alkylene optionally substituted with one or more oxo.

In some embodiments, $L^2$ is $C_{5-10}$ alkylene optionally substituted with one or more oxo.

In some embodiments, $L^2$ is $-C(O)-C_{0-39}$ alkylene. In some embodiments, $L^2$ is $-C(O)-C_{1-15}$ alkylene. In some embodiments, $L^2$ is $-C(O)-C_{1-10}$ alkylene. In some embodiments, $L^2$ is $-C(O)-C_{5-10}$ alkylene.

In some embodiments, $L^2$ is $C_{2-40}$ heteroalkylene optionally substituted with one or more oxo.

In some embodiments, $L^2$ is $-C(O)-C_{1-39}$ heteroalkylene.

In some embodiments, $L^2$ is —C(O)—(CH$_2$CH$_2$O)$_{1-10}$—CH$_2$CH$_2$—. In some embodiments, $L^2$ is —C(O)—(CH$_2$CH$_2$O)$_{1-8}$—CH$_2$CH$_2$—. In some embodiments, $L^2$ is —C(O)—(CH$_2$CH$_2$O)$_{1-5}$—CH$_2$CH$_2$—. In some embodiments, $L^2$ is —C(O)—(CH$_2$CH$_2$O)$_{2-10}$—CH$_2$CH$_2$—. In some embodiments, $L^2$ is —C(O)—(CH$_2$CH$_2$O)$_{2-8}$—CH$_2$CH$_2$—. In some embodiments, $L^2$ is —C(O)—(CH$_2$CH$_2$O)$_{2-5}$—CH$_2$CH$_2$—.

In some embodiments, $L^2$ is —C(O)—CH$_2$CH$_2$O—CH$_2$CH$_2$—. In some embodiments, $L^2$ is —C(O)—(CH$_2$CH$_2$O)$_2$—CH$_2$CH$_2$—. In some embodiments, $L^2$ is —C(O)—(CH$_2$CH$_2$O)$_3$—CH$_2$CH$_2$—. In some embodiments, $L^2$ is —C(O)—(CH$_2$CH$_2$O)$_4$—CH$_2$CH$_2$—. In some embodiments, $L^2$ is —C(O)—(CH$_2$CH$_2$O)$_5$—CH$_2$CH$_2$—. In some embodiments, $L^2$ is —C(O)—(CH$_2$CH$_2$O)$_6$—CH$_2$CH$_2$—. In some embodiments, $L^2$ is —C(O)—(CH$_2$CH$_2$O)$_7$—CH$_2$CH$_2$—. In some embodiments, $L^2$ is —C(O)—(CH$_2$CH$_2$O)$_8$—CH$_2$CH$_2$—. In some embodiments, $L^2$ is —C(O)—(CH$_2$CH$_2$O)$_9$—CH$_2$CH$_2$—. In some embodiments, $L^2$ is —C(O)—(CH$_2$CH$_2$O)$_{10}$—CH$_2$CH$_2$—.

In some embodiments, $L^2$ is

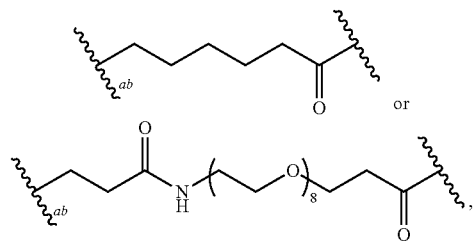

wherein bond ab is attached to $R^6$.

In some embodiments, $R^5$ is —(CH$_2$)$_p$—O—(CH$_2$)$_q$—NH-(AA)$_n$- C(O)—C$_{1-10}$ alkylene-R$^6$. In some embodiments, $R^5$ is —(CH$_2$)$_p$—O—(CH$_2$)$_q$—NH-(AA)$_n$- C(O)—(CH$_2$)$_{1-10}$—CH$_2$CH$_2$-R$^6$.

In some embodiments, $R^5$ is —(CH$_2$)$_p$—O—(CH$_2$)$_q$—NH-GFGG-C(O)—C$_{1-10}$ alkylene-R$^6$. In some embodiments, $R^5$ is —(CH$_2$)$_p$—O—(CH$_2$)$_q$—NH-GFGG-C(O)—(CH$_2$)$_{1-10}$—CH$_2$CH$_2$-R$^6$.

In some embodiments, $R^5$ is —(CH$_2$)$_p$—O—(CH$_2$)$_q$—NH-(AA)$_n$- C(O)—C$_{1-30}$ heteroalkylene-R$^6$. In some embodiments, $R^5$ is —(CH$_2$)$_p$—O—(CH$_2$)$_q$—NH-(AA)$_n$- C(O)—(CH$_2$CH$_2$O)$_{1-10}$—CH$_2$CH$_2$-R$^6$.

In some embodiments, $R^5$ is —(CH$_2$)$_p$—O—(CH$_2$)$_q$—NH-GFGG-C(O)—C$_{1-35}$ heteroalkylene-R$^6$. In some embodiments, $R^5$ is —(CH$_2$)$_p$—O—(CH$_2$)$_q$—NH-GFGG-C(O)—C$_{1-30}$ heteroalkylene-R$^6$. In some embodiments, $R^5$ is —(CH$_2$)$_p$—O—(CH$_2$)$_q$—NH-GFGG-C(O)—(CH$_2$CH$_2$O)$_{1-10}$—CH$_2$CH$_2$-R$^6$.

In some embodiments, $R^5$ is —(CH$_2$)$_p$—O—(CH$_2$)$_q$—NH-GFGG-C(O)—C$_{1-35}$ heteroalkylene-R$^6$. In some embodiments, $R^5$ is —(CH$_2$)$_p$—O—(CH$_2$)$_q$—NH-GFGG-C(O)—C$_{1-30}$ heteroalkylene-R$^6$. In some embodiments, $R^5$ is —(CH$_2$)$_p$—O—(CH$_2$)$_q$—NH-GFGG-C(O)—(CH$_2$CH$_2$O)$_{1-10}$—CH$_2$CH$_2$-R$^6$.

In some embodiments, $R^5$ is:

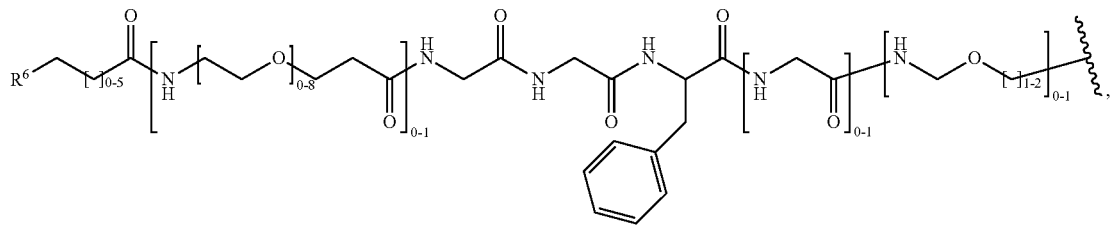

where $R^6$ is heterocyclyl, wherein said heterocyclyl is optionally covalently linked to an antibody or antigen-binding fragment.

In some embodiments, $R^5$ is:

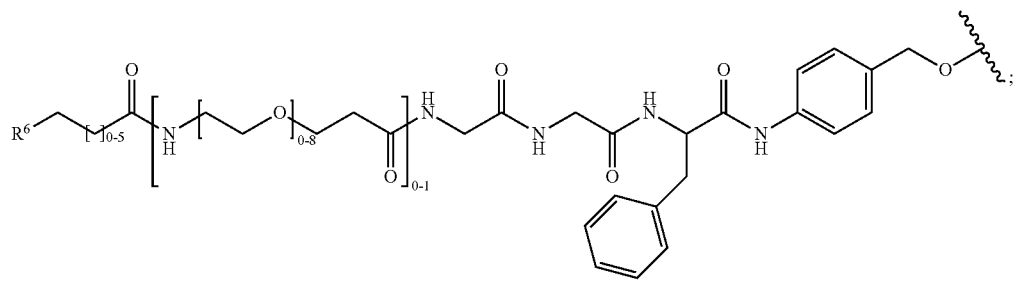

where $R^6$ is heterocyclyl, wherein said heterocyclyl is optionally covalently linked to an antibody or antigen-binding fragment.

In some embodiments, $R^5$ is:

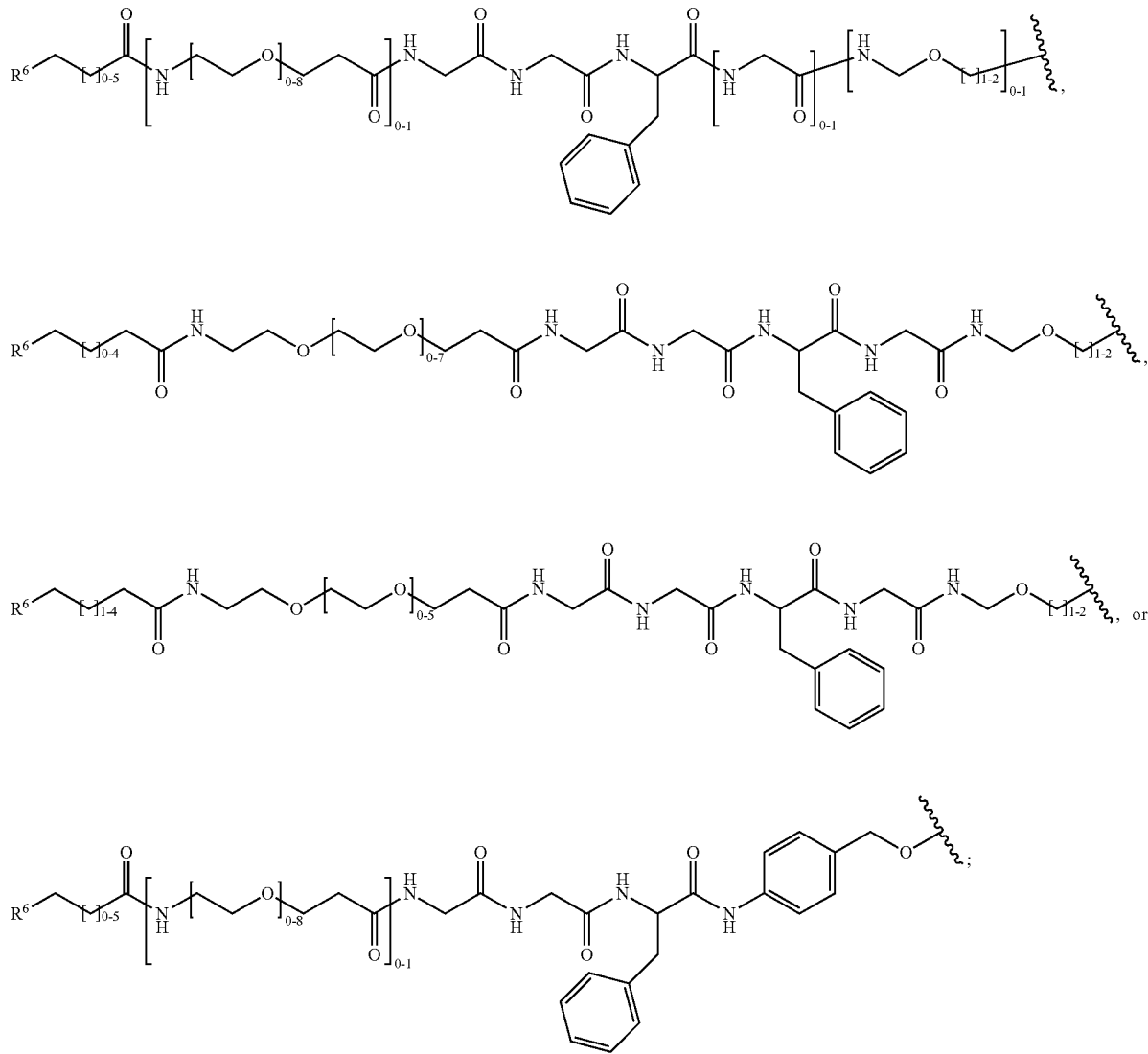

where $R^6$ is heterocyclyl, wherein said heterocyclyl is optionally covalently linked to an antibody or antigen-binding fragment.

In some embodiments, p is 1. In some embodiments, p is 2. In some embodiments, p is 3. In some embodiments, p is 4.

In some embodiments, q is 1. In some embodiments, q is 2. In some embodiments, q is 3. In some embodiments, q is 4.

In some embodiments, p is 1 and q is 1. In some embodiments, p is 2 and q is 1. In some embodiments, p is 3 and q is 1. In some embodiments, p is 4 and q is 1. In some embodiments, p is 1 and q is 2. In some embodiments, p is 2 and q is 2. In some embodiments, p is 3 and q is 2. In some embodiments, p is 4 and q is 2. In some embodiments, p is 1 and q is 3. In some embodiments, p is 2 and q is 3. In some embodiments, p is 3 and q is 3. In some embodiments, p is 4 and q is 3. In some embodiments, p is 1 and q is 4. In some embodiments, p is 2 and q is 4. In some embodiments, p is 3 and q is 4. In some embodiments, p is 4 and q is 4.

In some embodiments, $R^6$ is hydrogen. In some embodiments, $R^6$ is heterocyclyl, wherein said heterocyclyl is optionally covalently linked to an antibody or antigen-binding fragment. In some embodiments, $R^6$ is heterocyclyl.

In some embodiments, $A^3$ is —NH—C(O)$R^5$; and $A^1$ and $A^2$ are both hydrogen.

In some embodiments, $A^3$ is —NH—C(O)-$L^1$-(AA)-$L^2$-$R^6$; and $A^1$ and $A^2$ are both hydrogen.

In some embodiments, $A^3$ is —NH—C(O)-$L^1$-(AA)-$L^2$-$R^6$; and $A^1$ and $A^2$ are both hydrogen;

$L^1$ is —(CH$_2$)$_p$—X$^1$—(CH$_2$)$_q$—X$^2$—* or —X$^1$—(CH$_2$)$_p$-phenylene-(CH$_2$)$_q$—X$^2$—*; wherein the * bond is attached to the -(AA)$_n$-$L^2$-$R^6$;

n is 0, 1, 2, 3, 4, 5, or 6;

each AA is independently an amino acid; and $L^2$ is $C_{1-40}$ alkylene or $C_{2-40}$ heteroalkylene, wherein the $C_{1-40}$ alkylene or $C_{2-40}$ heteroalkylene optionally comprises a phenylene within the $C_{1-40}$ alkylene or $C_{2-40}$ heteroalkylene chain, and the $C_{1-40}$ alkylene or $C_{2-40}$ heteroalkylene is optionally substituted with one or more (e.g., one or two) oxo.

In some embodiments, $R^1$, $R^2$, or $R^3$ is:
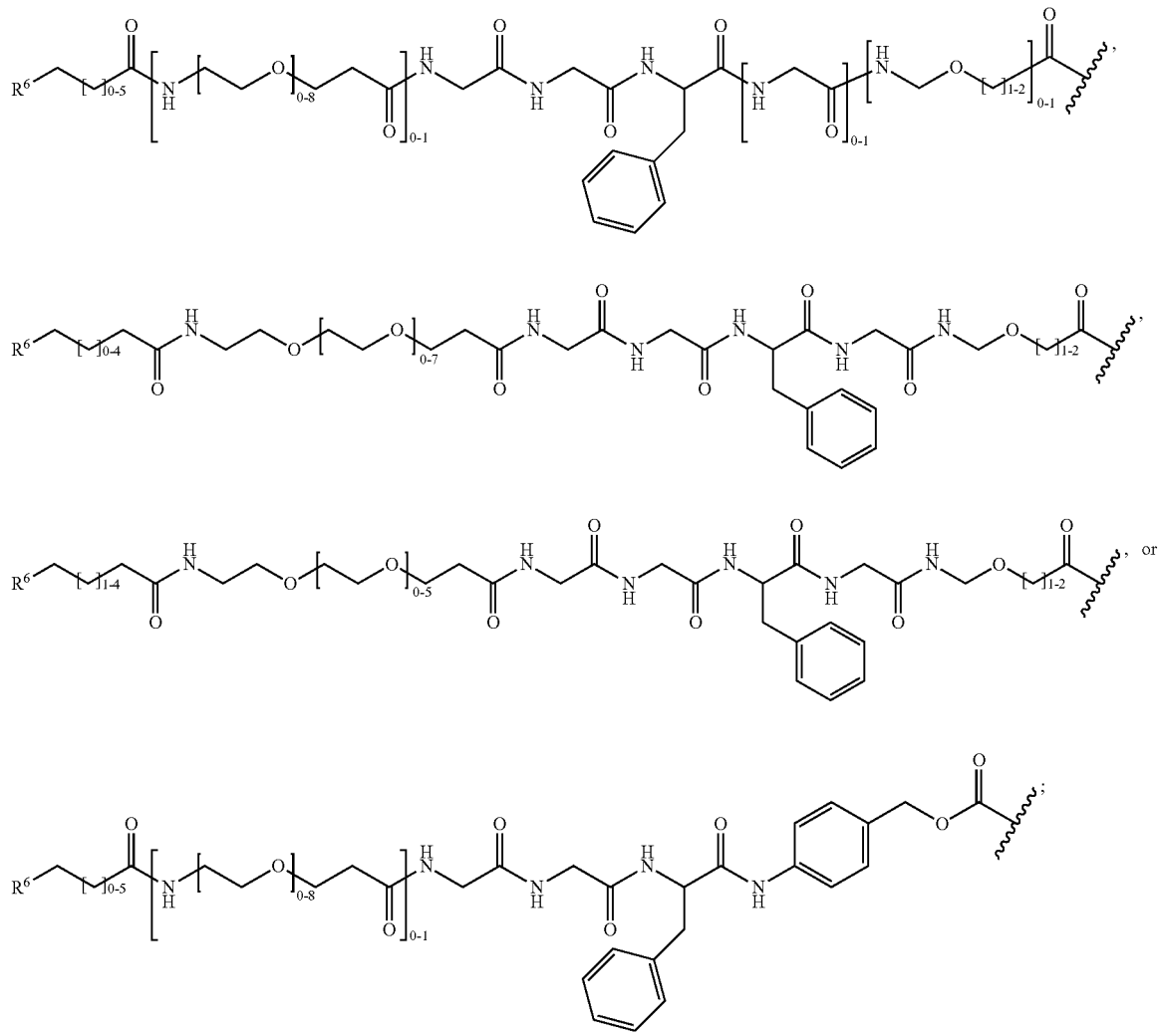
where $R^6$ is heterocyclyl, wherein said heterocyclyl is optionally covalently linked to an antibody or antigen-binding fragment.
In some embodiments, $R^1$, $R^2$, or $R^3$ is:
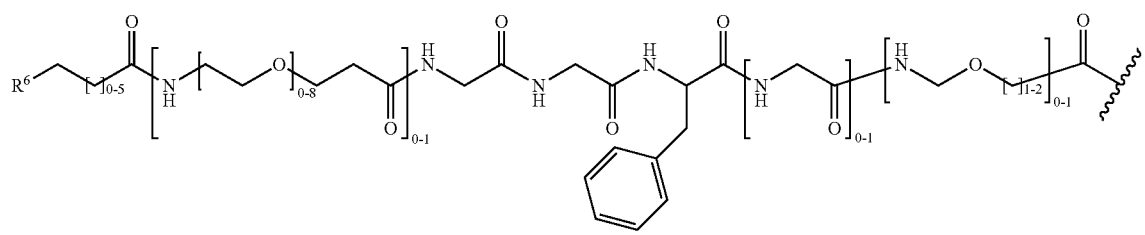
where $R^6$ is heterocyclyl, wherein said heterocyclyl is optionally covalently linked to an antibody or antigen-binding fragment.

In some embodiments, $R^1$, $R^2$, or $R^3$ is:

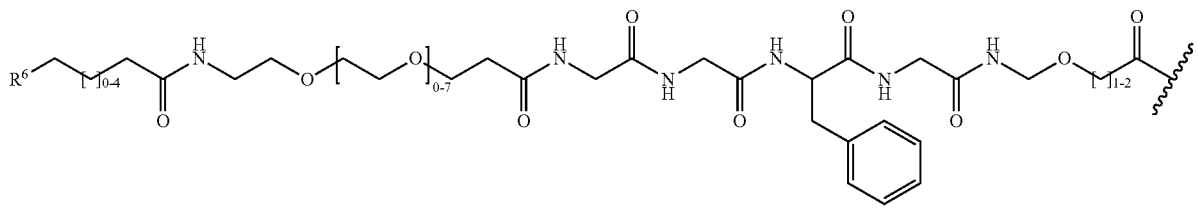

where $R^6$ is heterocyclyl, wherein said heterocyclyl is optionally covalently linked to an antibody or antigen-binding fragment.

In some embodiments, $R^1$, $R^2$, or $R^3$ is:

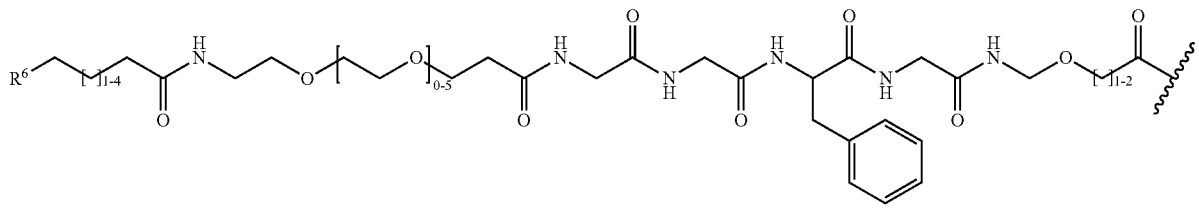

where $R^6$ is heterocyclyl, wherein said heterocyclyl is optionally covalently linked to an antibody or antigen-binding fragment.

In some embodiments, $R^1$, $R^2$, or $R^3$ is:

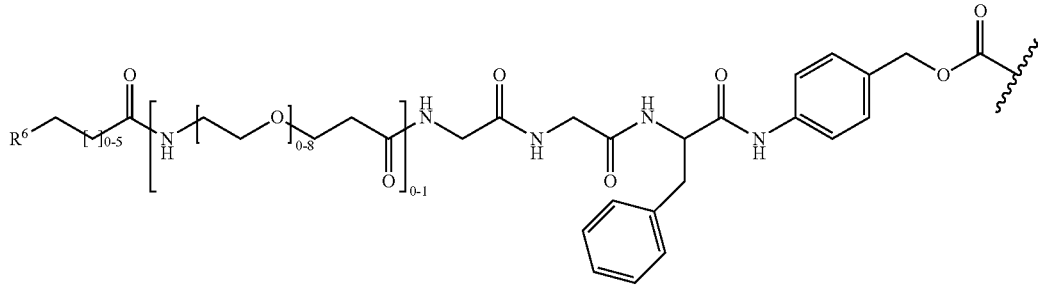

where $R^6$ is heterocyclyl, wherein said heterocyclyl is optionally covalently linked to an antibody or antigen-binding fragment.

In some embodiments, $R^6$ is heterocyclyl, which heterocyclyl is covalently linked to an antibody or antigen-binding fragment.

In some embodiments, $R^6$ is heterocyclyl, wherein said heterocyclyl is optionally covalently linked to an antibody or antigen-binding fragment via a cystine or lysine residue on the antibody or antigen-binding fragment.

In some embodiments, $R^6$ is

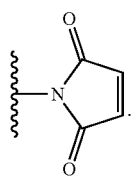

In some embodiments, $R^6$ is

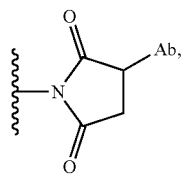

wherein Ab is an antibody or an antigen-binding fragment.

In some embodiments, $R^1$, $R^2$, or $R^3$ is:
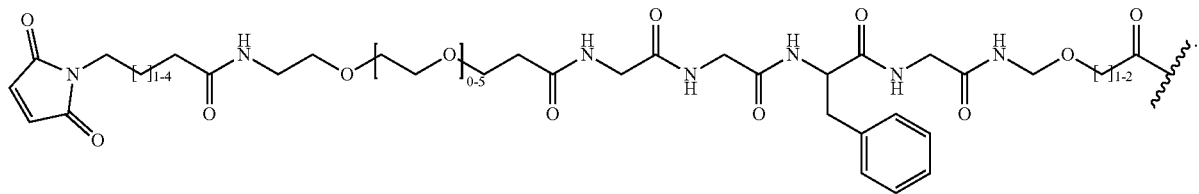
In some embodiments, $R^1$, $R^2$, or $R^3$ is:
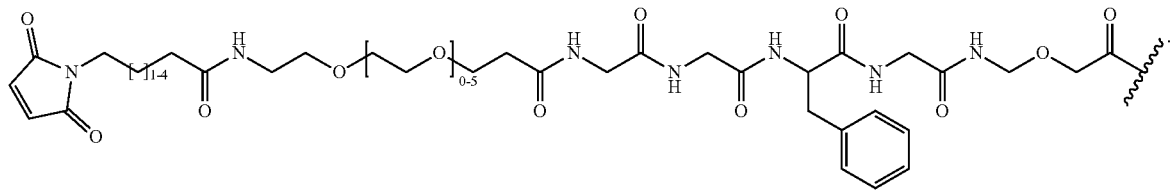
In some embodiments, $R^1$, $R^2$, or $R^3$ is:
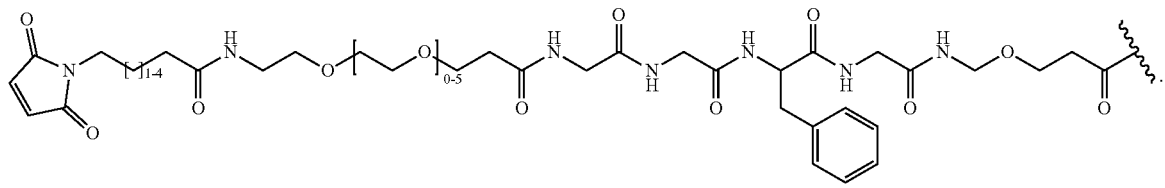
In some embodiments, $R^1$, $R^2$, or $R^3$ is:
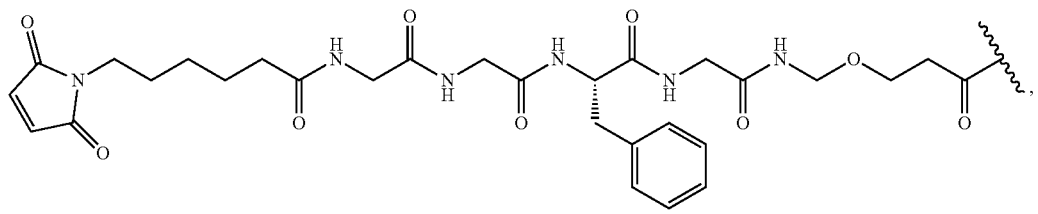
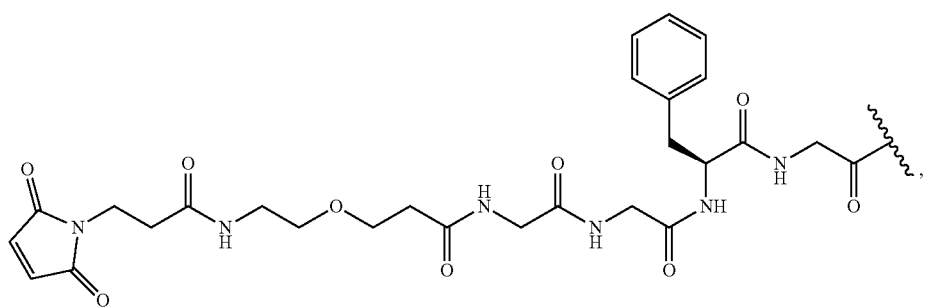

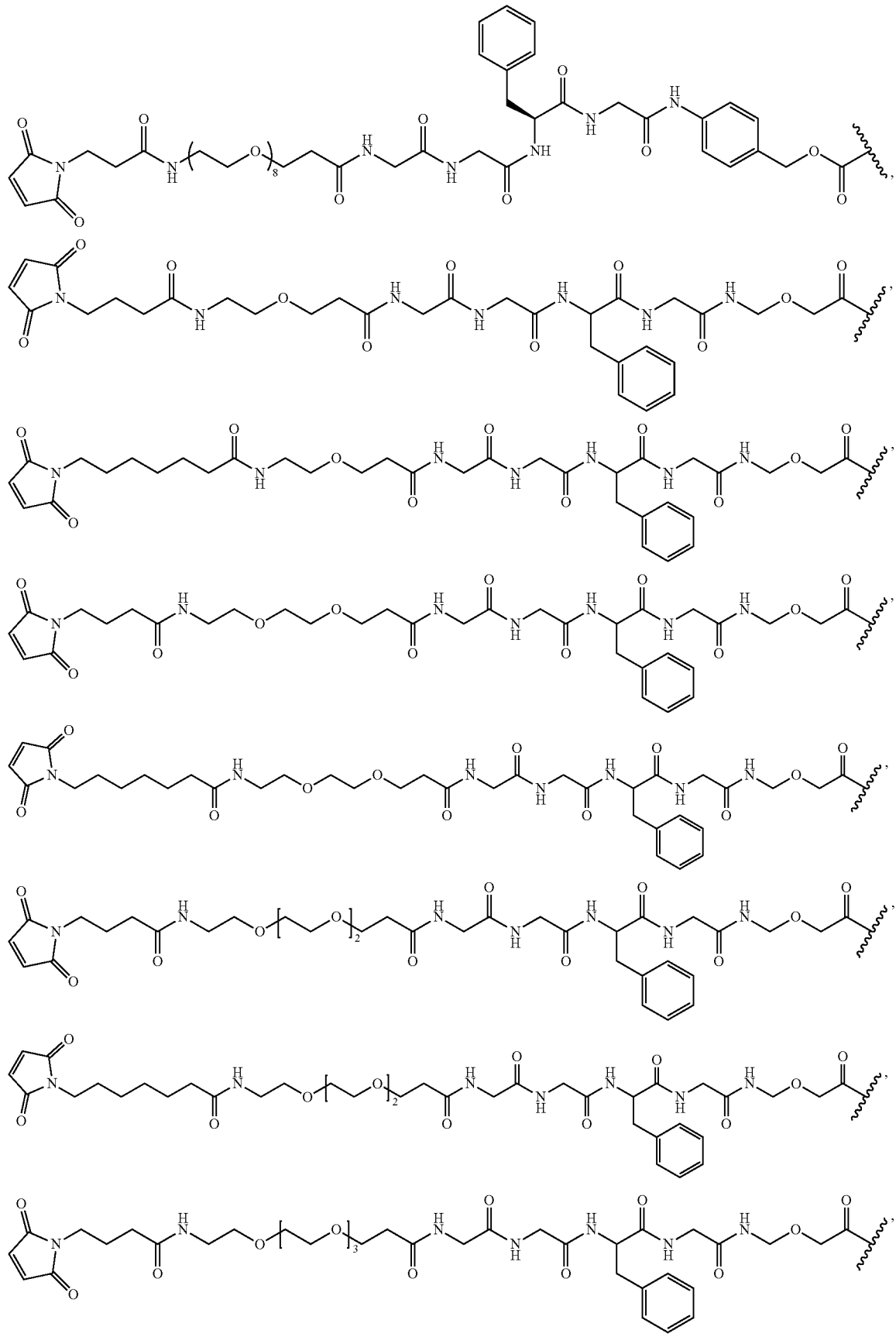

-continued
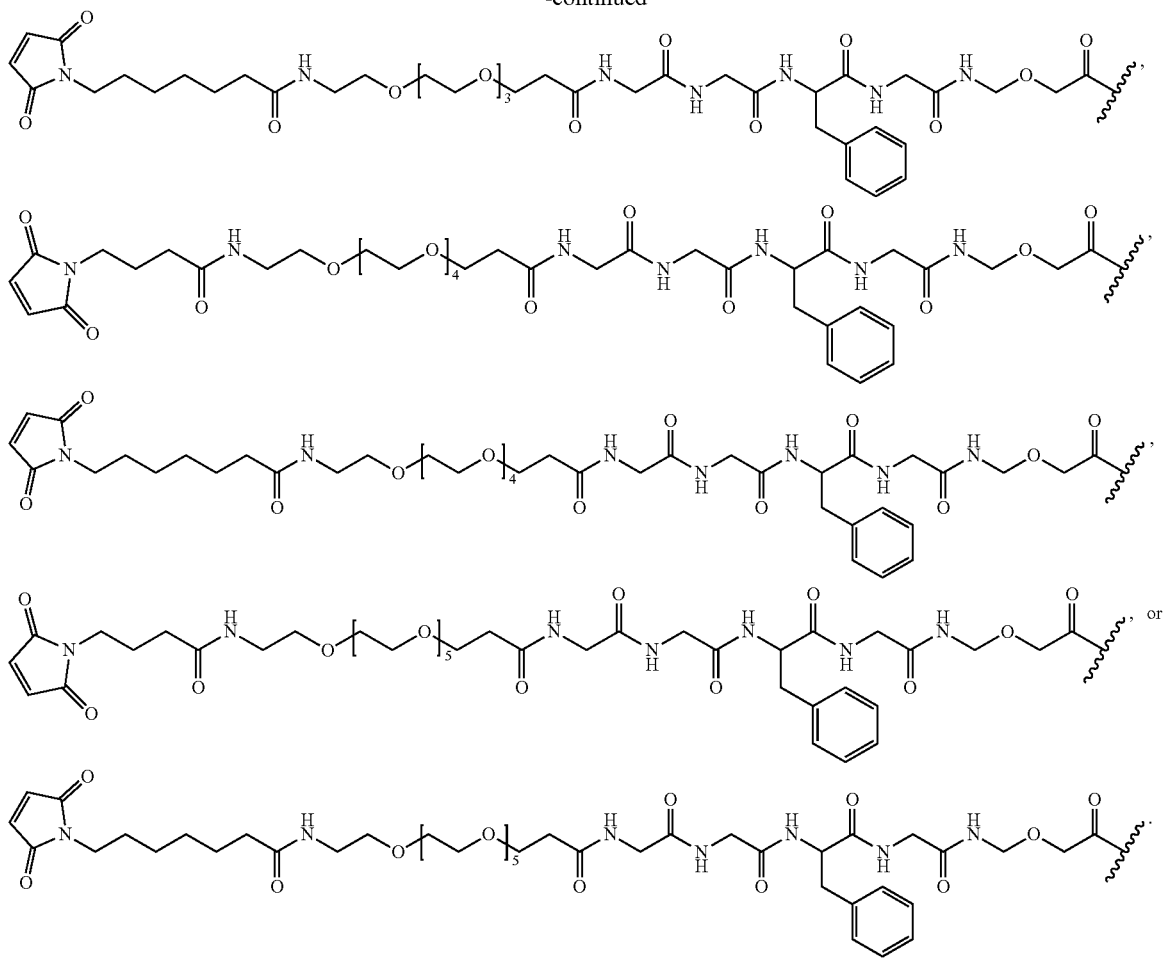
In some embodiments, $R^1$, $R^2$, or $R^3$ is:
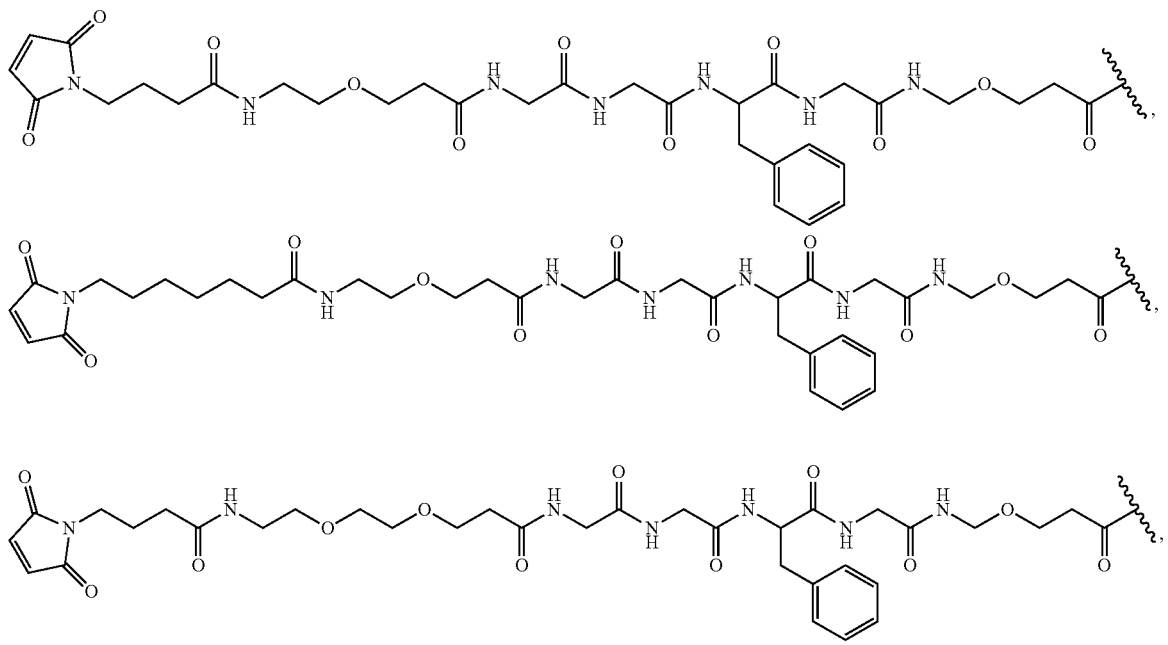

-continued
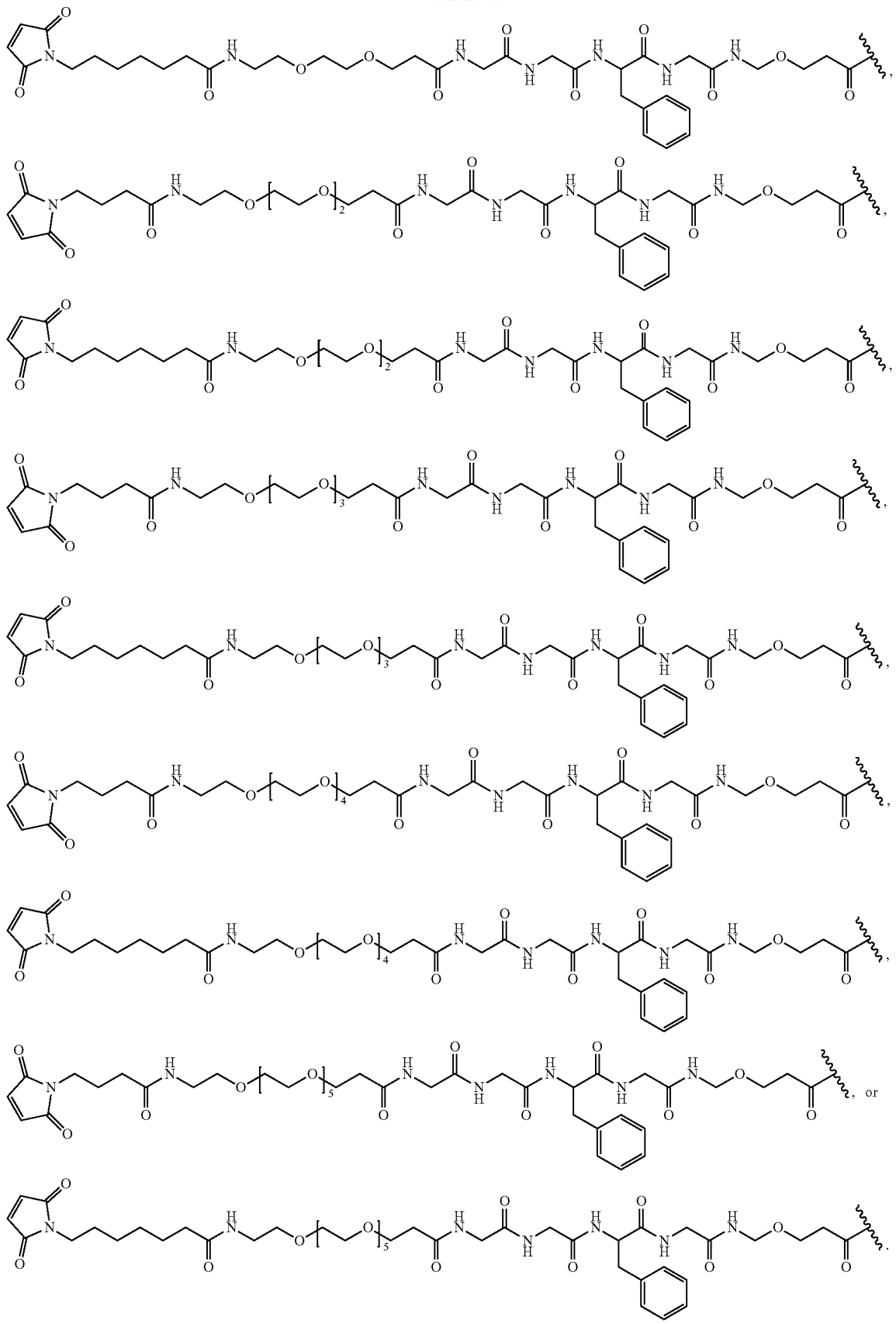

In some embodiments, provided is a compound selected from:

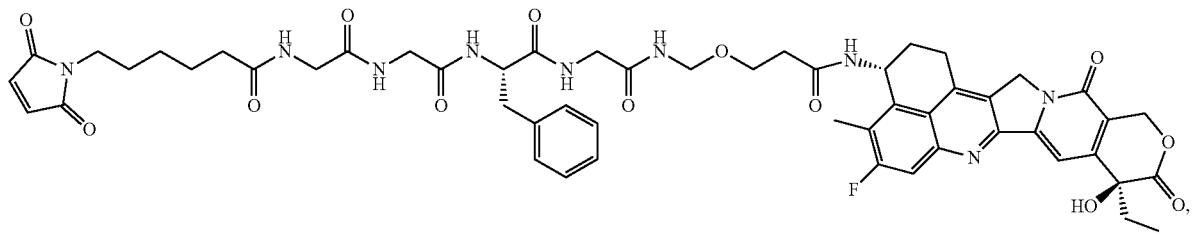

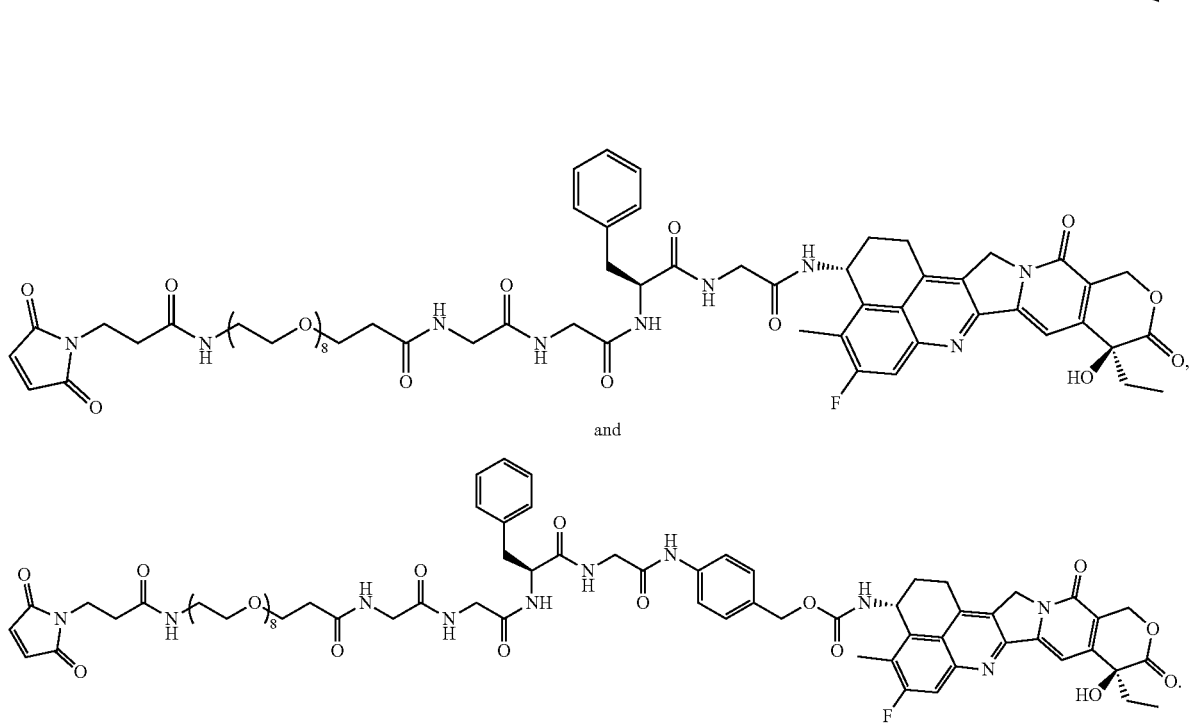

In some embodiments, $R^6$ is

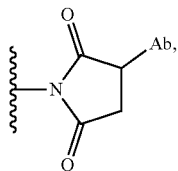

wherein Ab is an antibody or an antigen-binding fragment.

In some embodiments, the antibody or antigen-binding fragment can comprise more than one payload portion (e.g., compound of Formula I). Accordingly, also provided is a compound of Formula V:

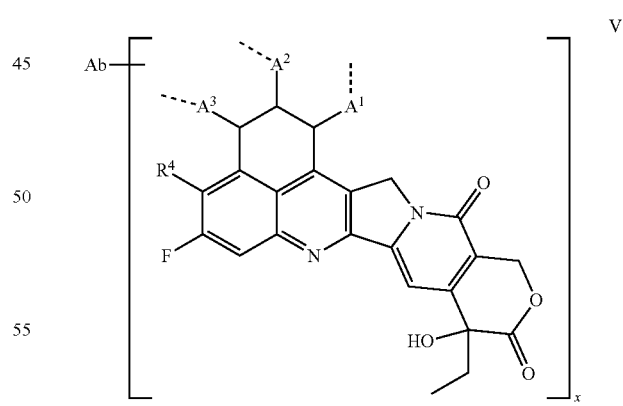

wherein each of $A^1$, $A^2$, $A^3$ and $R^4$ are independently as defined herein; one dashed line represents a bond to Ab and the other two dashed lines are absent, and x is from 1-20, or 1-15, or 1-10, or 1-5, or 2-8, or 3-8, or 4-8. In some embodiments, x is 4. In some embodiments, x is 5. In some embodiments, x is 6. In some embodiments, x is 7. In some embodiments, x is 8. In some embodiments, x is 4, 6, or 8. In some embodiments, x is 4-8.

In some embodiments, provided is a compound selected from:

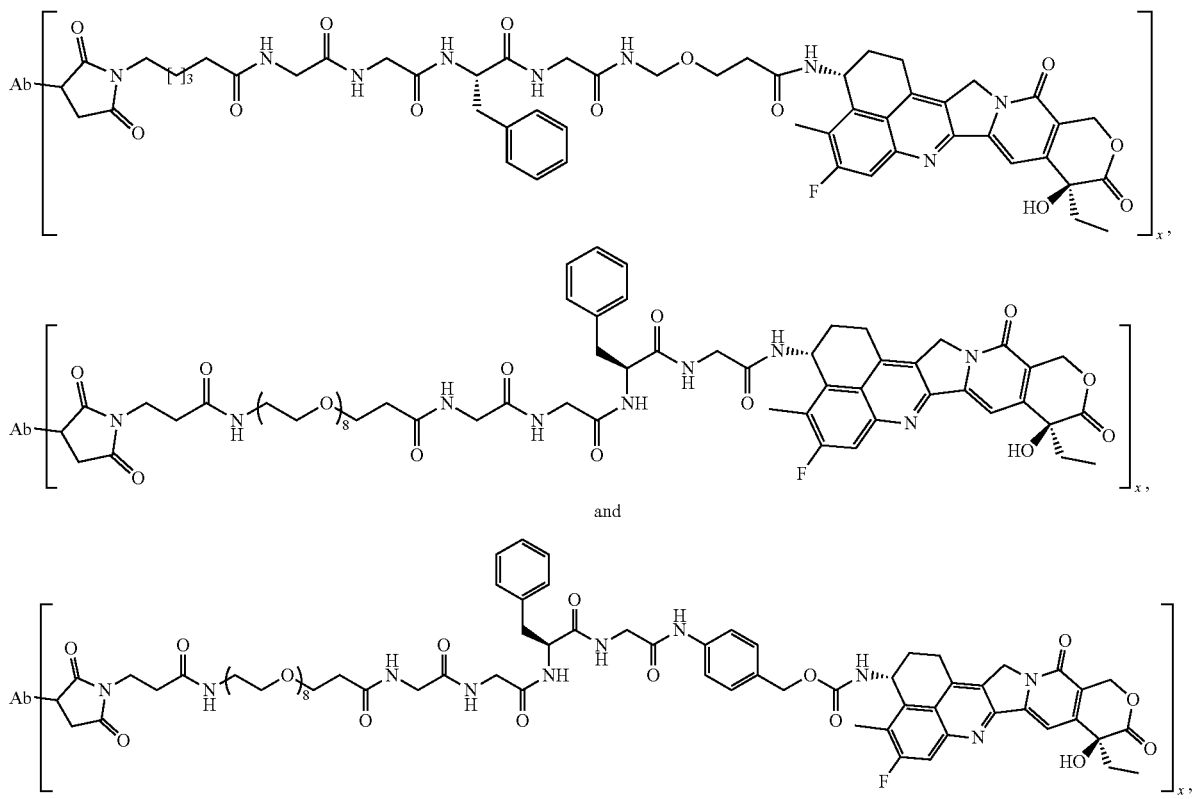

wherein Ab is an antibody or an antigen-binding fragment.

Examples of antibodies include, but are not limited to, 3F8 (anti-GD2), Abagovomab (anti CA-125), Abciximab (anti CD41 (integrin alpha-IIb), Adalimumab (anti-TNF-α), Adecatumumab (anti-EpCAM, CD326), Afelimomab (anti-TNF-α), Afutuzumab (anti-CD20), Alacizumab pegol (anti-VEGFR2), ALD518 (anti-IL-6), Alemtuzumab (Campath, MabCampath, anti-CD52), Altumomab (anti-CEA), Anatumomab (anti-TAG-72), Anrukinzumab (IMA-638, anti-IL-13), Apolizumab (anti-HLA-DR), Arcitumomab (anti-CEA), Aselizumab (anti-L-selectin (CD62L), Atlizumab (tocilizumab, Actemra, RoActemra, anti-IL-6 receptor), Atorolimumab (anti-Rhesus factor), Bapineuzumab (anti-beta amyloid), Basiliximab (Simulect, antiCD25 (a chain of IL-2 receptor), Bavituximab (anti-phosphatidylserine), Bectumomab (LymphoScan, anti-CD22), Belimumab (Benlysta, LymphoStat-B, anti-BAFF), Benralizumab (anti-CD125), Bertilimumab (anti-CCL11 (eotaxin-1)), Besilesomab (Scintimun, anti-CEA-related antigen), Bevacizumab (Avastin, anti-VEGF-A), Biciromab (FibriScint, anti-fibrin II beta chain), Bivatuzumab (anti-CD44 v6), Blinatumomab (BiTE, anti-CD19), Brentuximab (cAC10, anti-CD30 TNFRSF8), Briakinumab (anti-IL-12, IL-23) Canakinumab (Ilaris, anti-IL-1), Cantuzumab (C242, anti-CanAg), Capromab, Catumaxomab (Removab, anti-EpCAM, anti-CD3), CC49 (anti-TAG-72), Cedelizumab (anti-CD4), Certolizumab pegol (Cimzia anti-TNF-α), Cetuximab (Erbitux, IMC-C225, anti-EGFR), Citatuzumab bogatox (anti-EpCAM), Cixutumumab (anti-IGF-1), Clenoliximab (anti-CD4), Clivatuzumab (anti-MUC1), Conatumumab (anti-TRAIL-R2), CR6261 (anti-Influenza A hemagglutinin), Dacetuzumab (anti-CD40), Daclizumab (Zenapax, anti-CD25 (a chain of IL-2 receptor)), Daratumumab (anti-CD38 (cyclic ADP ribose hydrolase), Denosumab (Prolia, anti-RANKL), Detumomab (anti-B-lymphoma cell), Dorlimomab, Dorlixizumab, Ecromeximab (anti-GD3 ganglioside), Eculizumab (Soliris, anti-C5), Edobacomab (anti-endotoxin), Edrecolomab (Panorex, MAb17-1A, anti-EpCAM), Efalizumab (Raptiva, anti-LFA-1 (CD11a), Efungumab (Mycograb, anti-Hsp90), Elotuzumab (anti-SLAMF7), Elsilimomab (anti-IL-6), Enlimomab pegol (anti-ICAM-1 (CD54)), Epitumomab (anti-episialin), Epratuzumab (anti-CD22), Erlizumab (anti-ITGB2 (CD18)), Ertumaxomab (Rexomun, anti-HER2/neu, CD3), Etaracizumab (Abegrin, anti-integrin α vβ 3), Exbivirumab (anti-hepatitis B surface antigen), Fanolesomab (NeutroSpec, anti-CD15), Faralimomab (anti-interferon receptor), Farletuzumab (anti-folate receptor 1), Felvizumab (anti-respiratory syncytial virus), Fezakinumab (anti-IL-22), Figitumumab (anti-IGF-1 receptor), Fontolizumab (anti-IFN-γ), Foravirumab (anti-rabies virus glycoprotein), Fresolimumab (anti-TGF-β), Galiximab (anti-CD80), Gantenerumab (anti-beta amyloid), Gavilimomab (anti-CD147 (basigin)), Gemtuzumab (anti-CD33), Girentuximab (anti-carbonic anhydrase 9), Glembatumumab (CR011, anti-GPNMB), Golimumab (Simponi, anti-TNF-α), Gomiliximab (anti-CD23 (IgE receptor)), anti-HLA-DR antibody, Ibalizumab (anti-CD4), Ibritumomab (anti-CD20), Igovomab (Indimacis-125, anti-CA-125), Imciromab (Myoscint, anti-cardiac myosin), Infliximab (Remicade, anti-TNF-α), Intetumumab (anti-CD51), Inolimomab (anti-CD25 (a chain of IL-2 receptor)), Inotuzumab (anti-CD22), Ipilimumab (anti-CD152), Iratumumab (anti- CD30 (TNFRSF8)), Keliximab (anti-CD4), Labetuzumab (CEA-Cide, anti-CEA), Lebrikizumab (anti-IL-13), Lemalesomab (anti-NCA-90 (granulocyte antigen)), Lerdelimumab (anti-TGF beta 2), Lexatumumab (anti-TRAIL-R2), Libivirumab (anti-hepatitis B surface antigen), Lintuzumab (anti-CD33), Lucatumumab (anti-CD40), Lumiliximab (anti-CD23 (IgE receptor), Mapatumumab (anti-TRAIL-R1), Maslimomab (anti-T-cell receptor), Matuzumab (anti-EGFR), Mepolizumab (Bosatria, anti-IL-5), Metelimumab (anti-TGF beta 1), Milatuzumab (anti-CD74), Minretumomab (anti-TAG-72), Mitumomab (BEC-2, anti-GD3 ganglioside), Morolimumab (anti-Rhesus factor), Motavizumab (Numax, anti-respiratory syncytial virus), Muromonab-CD3 (Orthoclone OKT3, anti-CD3), Nacolomab (anti-C242), Naptumomab (anti-5T4), Natalizumab (Tysabri, anti-integrin α 4), Nebacumab (anti-endotoxin), Necitumumab (anti-EGFR), Nerelimomab (anti-TNF-α), Nimotuzumab (Theracim, Theraloc, anti-EGFR), Nofetumomab, Ocrelizumab (anti-CD20), Odulimomab (Afolimomab, anti-LFA-1 (CD11a)), Ofatumumab (Arzerra, anti-CD20), Olaratumab (anti-PDGF-R a), Omalizumab (Xolair, anti-IgE Fc region), Oportuzumab (anti-EpCAM), Oregovomab (OvaRex, anti-CA-125), Otelixizumab (anti-CD3), Pagibaximab (anti-lipoteichoic acid), Palivizumab (Synagis, Abbosynagis, anti-respiratory syncytial virus), Panitumumab (Vectibix, ABX-EGF, anti-EGFR), Panobacumab (anti-*Pseudomonas aeruginosa*), Pascolizumab (anti-IL-4), Pemtumomab (Theragyn, anti-MUC1), Pertuzumab (Omnitarg, 2C4, anti-HER2/neu), Pexelizumab (anti-C5), Pintumomab (anti-adenocarcinoma antigen), Priliximab (anti-CD4), Pritumumab (anti-vimentin), PRO 140 (anti-CCR5), Racotumomab (1E10, anti-(N-glycolylneuraminic acid (NeuGc, NGNA)-gangliosides GM3)), Rafivirumab (anti-rabies virus glycoprotein), Ramucirumab (anti-VEGFR2), Ranibizumab (Lucentis, anti-VEGF-A), Raxibacumab (anti-anthrax toxin, protective antigen), Regavirumab (anti-cytomegalovirus glycoprotein B), Reslizumab (anti-IL-5), Rilotumumab (anti-HGF), Rituximab (MabThera, Rituxanmab, anti-CD20), Robatumumab (anti-IGF-1 receptor), Rontalizumab (anti-IFN-α), Rovelizumab (LeukArrest, anti-CD11, CD18), Ruplizumab (Antova, anti-CD154 (CD40L)), Satumomab (anti-TAG-72), Sevirumab (anti-cytomegalovirus), Sibrotuzumab (anti-FAP), Sifalimumab (anti-IFN-α), Siltuximab (anti-IL-6), Siplizumab (anti-CD2), (Smart) M195 (anti-CD33), Solanezumab (anti-beta amyloid), Sonepcizumab (anti-sphingosine-1-phosphate), Sontuzumab (anti-episialin), Stamulumab (anti-myostatin), Sulesomab (LeukoScan, (anti-NCA-90 (granulocyte antigen), Tacatuzumab (anti-alpha-fetoprotein), Tadocizumab (anti-integrin α IIbβ 3), Talizumab (anti-IgE), Tanezumab (anti-NGF), Taplitumomab (anti-CD19), Tefibazumab (Aurexis, (anti-clumping factor A), Telimomab, Tenatumomab (anti-tenascin C), Teneliximab (anti-CD40), Teplizumab (anti-CD3), TGN1412 (anti-CD28), Ticilimumab (Tremelimumab, (anti-CTLA-4), Tigatuzumab (anti-TRAIL-R2), TNX-650 (anti-IL-13), Tocilizumab (Atlizumab, Actemra, RoActemra, (anti-IL-6 receptor), Toralizumab (anti-CD154 (CD40L)), Tositumomab (anti-CD20), Trastuzumab (Herceptin, (anti-HER2/neu), Tremelimumab (anti-CTLA-4), Tucotuzumab celmoleukin (anti-EpCAM), Tuvirumab (anti-hepatitis B virus), Urtoxazumab (anti-*Escherichia coli*), Ustekinumab (Stelara, anti-IL-12, IL-23), Vapaliximab (anti-AOC3 (VAP-1)), Vedolizumab, (anti-integrin α 4β 7), Veltuzumab (anti-CD20), Vepalimomab (anti-AOC3 (VAP-1), Visilizumab (Nuvion, anti-CD3), Vitaxin (anti-vascular integrin avb3), Volociximab (anti-integrin α 5β 1), Votumumab (HumaSPECT, anti-tumor antigen CTAA16.88), Zalutumumab (HuMax-EGFr, (anti-EGFR), Zanolimumab (HuMax-CD4, anti-CD4), Ziralimumab (anti-CD147 (basigin)), Zolimomab (anti-CD5), Etanercept, Alefacept, Abatacept, Rilonacept (Arcalyst), 14F7 (anti-IRP-2 (Iron Regulatory Protein 2)), 14G2a (anti-GD2 ganglioside, from Nat. Cancer Inst. for melanoma and solid tumors), J591 (anti-PSMA, Weill Cornell Medical School for prostate cancers), 225.28S (anti-HMW-MAA (High molecular weight-melanoma-associated antigen), Sorin Radiofarmaci S.R.L. (Milan, Italy) for melanoma), COL-1 (anti-CEACAM3, CGM1, from Nat. Cancer Inst. USA for colorectal and gastric cancers), CYT-356 (for prostate cancers), HNK20 (OraVax Inc. for respiratory syncytial virus), ImmuRAIT (from Immunomedics for NHL), Lym-1 (anti-HLA-DR10, Peregrine Pharm. for Cancers), MAK-195F (anti-TNF (tumor necrosis factor; TNFA, TNF-alpha; TNFSF2), from Abbott/Knoll for Sepsis toxic shock), MEDI-500, T10B9, anti-CD3, TRax (T cell receptor alpha/beta), complex, from MedImmune Inc for Graft-versus-host disease), RING SCAN (anti-TAG 72 (tumor associated glycoprotein 72), from Neoprobe Corp. for Breast, Colon and Rectal cancers), Avicidin (anti-EPCAM (epithelial cell adhesion molecule), anti-TACSTDT (Tumor-associated calcium signal transducer 1), anti-GA733-2 (gastrointestinal tumor-associated protein 2), anti-EGP-2 (epithelial glycoprotein 2), anti-KSA; KS1/4 antigen; M4S; tumor antigen 17-1A; CD326, from NeoRx Corp. for Colon, Ovarian, Prostate cancers and NHL), anti-Trop-2-humanized antibody hRS7, LymphoCide (Immunomedics, NJ), Smart ID10 (Protein Design Labs), Oncolym (Techniclone Inc, CA), Allomune (BioTransplant, CA), anti-VEGF (Genentech, CA), CEAcide (Immunomedics, NJ), IMC-1C11 (ImClone Systems), and Cetuximab (ImClone).

In some embodiments, the antibody or antigen-binding fragment, targets one or more of the following antigens: Aminopeptidase N (CD13), Annexin A1, B7-H3 (CD276, various cancers), CA125 (ovarian), CA15-3 (carcinomas), CA19-9 (carcinomas), L6 (carcinomas), Lewis Y (carcinomas), Lewis X (carcinomas), alpha fetoprotein (carcinomas), CA242 (colorectal), placental alkaline phosphatase (carcinomas), prostate specific antigen (prostate), prostatic acid phosphatase (prostate), epidermal growth factor (carcinomas), CD2 (Hodgkin's disease, NHL lymphoma, multiple myeloma), CD3 epsilon (T cell lymphoma, lung, breast, gastric, ovarian cancers, autoimmune diseases, malignant ascites), CD19 (B cell malignancies), CD20 (non-Hodgkin's lymphoma), CD22 (leukemia, lymphoma, multiple myeloma, SLE), CD30 (Hodgkin's lymphoma), CD33 (leukemia, autoimmune diseases), CD38 (multiple myeloma), CD40 (lymphoma, multiple myeloma, leukemia (CLL)), CD51 (Metastatic melanoma, sarcoma), CD52 (leukemia), CD56 (small cell lung cancers, ovarian cancer, Merkel cell carcinoma, and the liquid tumor, multiple myeloma), CD66e (cancers), CD70 (metastatic renal cell carcinoma and non-Hodgkin lymphoma), CD74 (multiple myeloma), CD80 (lymphoma), CD98 (cancers), mucin (carcinomas), CD221 (solid tumors), CD227 (breast, ovarian cancers), CD262 (NSCLC and other cancers), CD309 (ovarian cancers), CD326 (solid tumors), CEACAM3 (colorectal, gastric cancers), CEACAM5 (carcinoembryonic antigen; CEA, CD66e) (breast, colorectal and lung cancers), DLL4 (Δ-like-4), EGFR (Epidermal Growth Factor Receptor, various cancers), CTLA4 (melanoma), CXCR4 (CD184, Hemeoncology, solid tumors), Endoglin (CD105, solid tumors), EPCAM (epithelial cell adhesion molecule, bladder, head, neck, colon, NHL prostate, and ovarian cancers), ERBB2 (Epidermal Growth Factor Receptor 2; lung, breast, prostate cancers), FCGR1 (autoimmune diseases), FOLR (folate receptor, ovarian cancers), GD2 ganglioside (cancers), G-28 (a cell surface antigen glycolipid, melanoma), GD3 idiotype (cancers), Heat shock proteins (cancers), HER1 (lung, stomach cancers), HER2 (breast, lung and ovarian cancers), HLA-DR10 (NHL), HLA-DRB (NHL, B cell leukemia), human chorionic gonadotropin (carcinoma), IGF1R (insulin-like growth factor 1 receptor, solid tumors, blood cancers), IL-2 receptor (interleukin 2 receptor, T-cell leukemia and lymphomas), IL-6R (interleukin 6 receptor, multiple myeloma, RA, Castleman's disease, IL6 dependent tumors), Integrins (αvβ, α5β1, α6β4, α11β3, α5β5, αvβ5, for various cancers), MAGE-1 (carcinomas), MAGE-2 (carcinomas), MAGE-3 (carcinomas), MAGE 4 (carcinomas), anti-transferrin receptor (carcinomas), p97 (melanoma), MS4A1 (membrane-spanning 4-domains subfamily A member 1, Non-Hodgkin's B cell lymphoma, leukemia), MUC1 or MUC1-KLH (breast, ovarian, cervix, bronchus and gastrointestinal cancer), MUC16 (CA125) (Ovarian cancers), CEA (colorectal), gp100 (melanoma), MART1 (melanoma), MPG (melanoma), MS4A1 (membrane-spanning 4-domains subfamily A, small cell lung cancers, NHL), Nucleolin, Neuoncogene product (carcinomas), P21 (carcinomas), Paratope of anti-(N-glycolylneuraminic acid, Breast, Melanoma cancers), PLAP-like testicular alkaline phosphatase (ovarian, testicular cancers), PSMA (prostate tumors), PSA (prostate), ROBO4, TAG 72 (tumor associated glycoprotein 72, AML, gastric, colorectal, ovarian cancers), T cell transmembrane protein (cancers), Tie (CD202b), TNFRSF10B (tumor necrosis factor receptor superfamily member 10B, cancers), TNFRSF13B (tumor necrosis factor receptor superfamily member 13B, multiple myeloma, NHL, other cancers, RA and SLE), TPBG (trophoblast glycoprotein, Renal cell carcinoma), TRAIL-R1 (Tumor necrosis apoptosis Inducing ligand Receptor 1, lymphoma, NHL, colorectal, lung cancers), VCAM-1 (CD106, Melanoma), VEGF, VEGF-A, or VEGF-2 (CD309) (various cancers).

In some embodiments, the antibody or antigen-binding fragment, targets one or more of the following antigens: various cluster of differentiations (CD4, CD5, CD6, CD7, CD8, CD9, CD10, CD11a, CD11b, CD11c, CD12w, CD14, CD15, CD16, CDw17, CD18, CD21, CD23, CD24, CD25, CD26, CD27, CD28, CD29, CD31, CD32, CD34, CD35, CD36, CD37, CD41, CD42, CD43, CD44, CD45, CD46, CD47, CD48, CD49b, CD49c, CD53, CD54, CD55, CD58, CD59, CD61, CD62E, CD62L, CD62P, CD63, CD68, CD69, CD71, CD72, CD79, CD81, CD82, CD83, CD86, CD87, CD88, CD89, CD90, CD91, CD95, CD96, CD100, CD103, CD105, CD106, CD109, CD117, CD120, CD127, CD133, CD134, CD135, CD138, CD141, CD142, CD143, CD144, CD147, CD151, CD152, CD154, CD156, CD158, CD163, CD166, CD168, CD184, CDw186, CD195, CD202 (a, b), CD209, CD235a, CD271, CD303, CD304), Annexin A1, Nucleolin, Endoglin (CD105), ROBO4, Amino-peptidase N, Δ-like-4 (DLL4), VEGFR-2 (CD309), CXCR4 9CD184), Tie2, B7-H3, WT1, MUC1, LMP2, HPV E6 E7, EGFRvIII, HER-2/neu, Idiotype, MAGE A3, p53 non-mutant, NY-ESO—1, GD2, CEA, MelanA/MART1, Ras mutant, gp100, p53 mutant, Proteinase3 (PR1), bcr-abl, Tyrosinase, Survivin, hTERT, Sarcoma translocation breakpoints, EphA2, PAP, ML-IAP, AFP, EpCAM, ERG (TMPRSS2 ETS fusion gene), NA17, PAX3, ALK, Androgen receptor, Cyclin B1, Polysialic acid, MYCN, RhoC, TRP-2, GD3, Fucosyl GM1, Mesothelin, PSCA, MAGE A1, sLe (a), CYP1B1, PLAC1, GM3, BORIS, Tn, GloboH, ETV6-AML, NY-BR-1, RGS5, SART3, STn, Carbonic anhydrase IX, PAX5, OY-TES1, Sperm protein 17, LCK, HMWMAA, AKAP-4, SSX2, XAGE 1, B7H3, Legumain, Tie 2, Page 4, VEGFR2, MAD-CT-1, FAP, PDGFR-β, MAD-CT-2, Fos-related antigen 1.

In some embodiments, Ab targets HER2, HER3, B7H3, TROP2, Claudin 18.2, CD30, CD33, CD70 or EGFR.

In some embodiments, provided is a compound selected from:

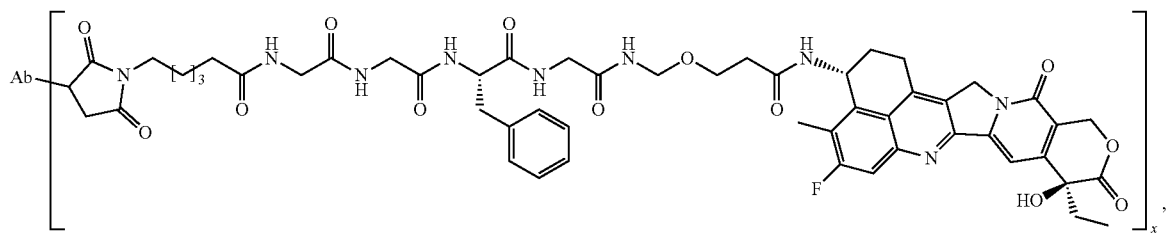

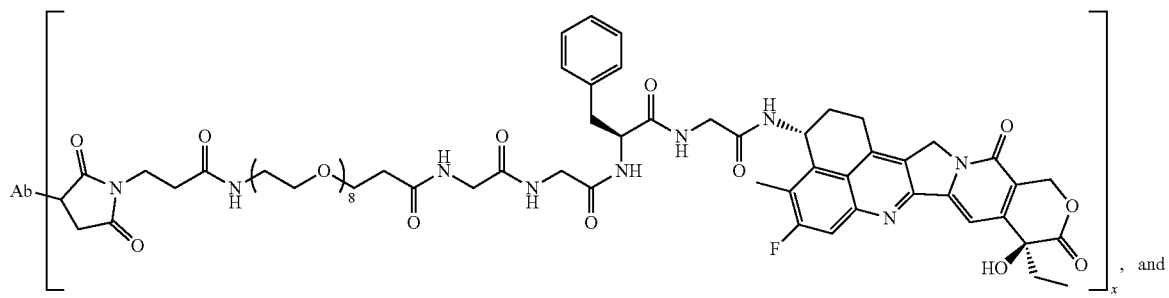

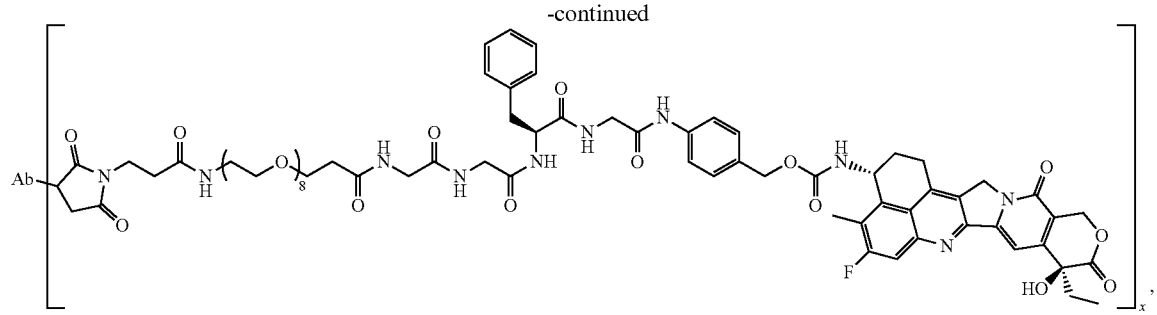
wherein Ab is an antibody or an antigen-binding fragment which targets HER2; and x is 4-8.
In some embodiments, provided is a compound selected from:
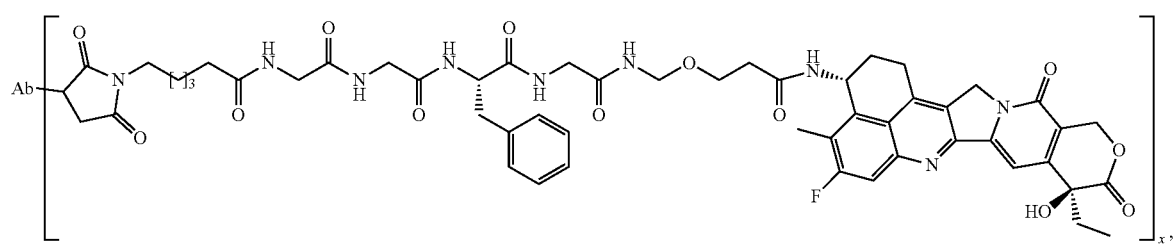
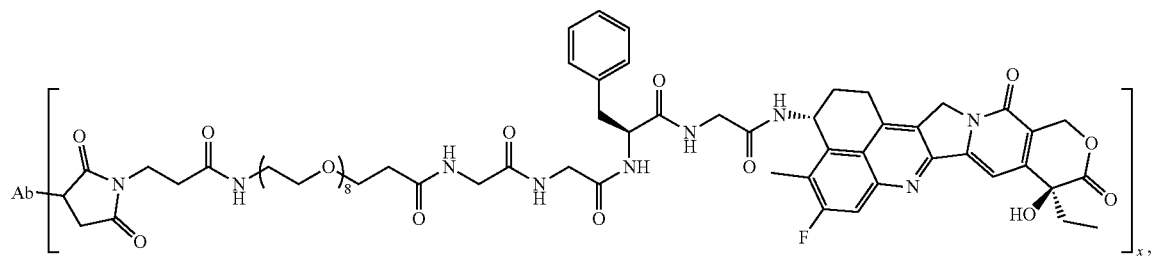
and
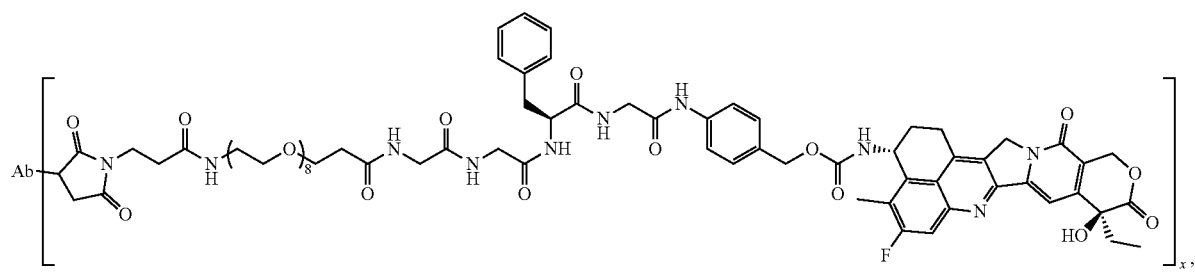
wherein Ab is Trastuzumab; and x is 4-8.

In some embodiments, provided is compound selected from Table 1A, or a stereoisomer or pharmaceutically acceptable salt thereof:

TABLE 1A

| No. | Structure |
|---|---|
| A-1 | 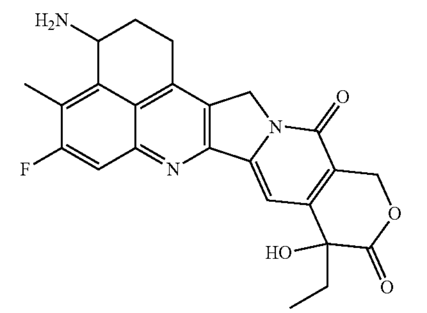 [SMILES: CCC1(O)C(=O)OCc2c1cc1n(c2=O)Cc2c-1nc1cc(F)c(C)c3c1c2CCC3N] |
| A-2 | 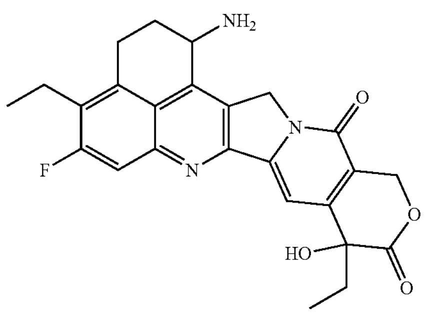 [SMILES: CCc1c(F)cc2nc3c(c4c2c1CCC4N)Cn1c-3cc2c(c1=O)COC(=O)C2(O)CC] |
| A-3 | 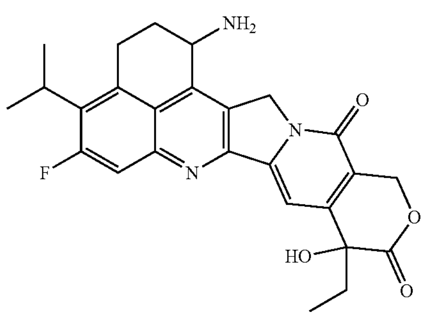 [SMILES: CCC1(O)C(=O)OCc2c1cc1n(c2=O)Cc2c-1nc1cc(F)c(C(C)C)c3c1c2C(N)CC3] |
| A-4 | 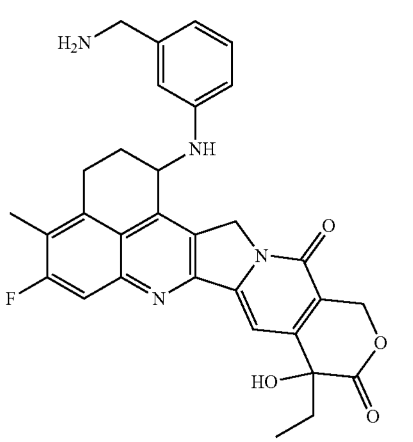 [SMILES: CCC1(O)C(=O)OCc2c1cc1n(c2=O)Cc2c-1nc1cc(F)c(C)c3c1c2C(Nc1cccc(CN)c1)CC3] |

TABLE 1A-continued

| No. | Structure |
|---|---|
| A-5 | 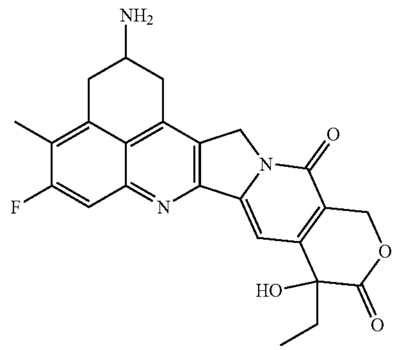 [SMILES: CCC1(O)C(=O)OCc2c1cc1n(c2=O)Cc2c-1nc1cc(F)c(C)c3c1c2CC(N)C3] |

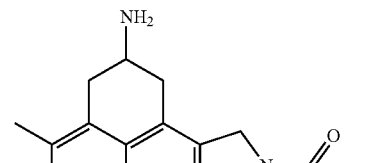

The compounds of Formula I provided herein encompass stereochemical forms of the compounds, for example, optical isomers, such as enantiomers, diastereomers, as well as mixtures thereof, e.g., mixtures of enantiomers and/or diastereomers, including racemic mixtures, as well as equal or non-equal mixtures of individual enantiomers and/or diastereomers. All stereochemical forms are contemplated in this disclosure. Unless otherwise indicated, when a disclosed compound is named or depicted by a structure without specifying the stereochemistry and has one or more chiral centers, it is understood to represent all possible stereoisomers of the compound. Representative stereochemical forms are provided throughout the specification, including but not limited to those delineated in Table 1B, 1C, and 1D.

In some embodiments, provided is compound selected from Table 1B, or a pharmaceutically acceptable salt or solvate thereof:

TABLE 1B

| No. | Structure |
|---|---|
| B-1 | 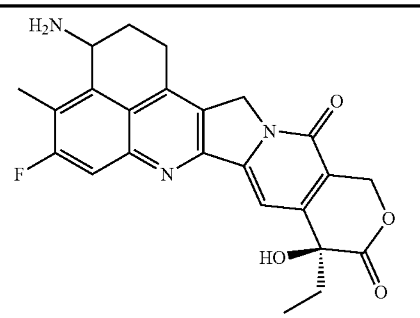 |
| B-2 | 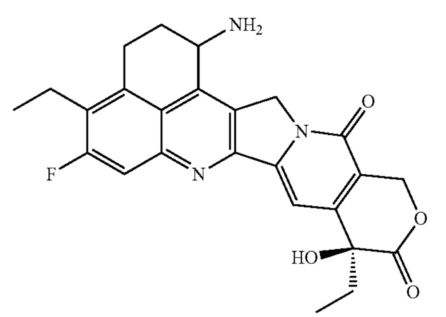 [SMILES: CCc1c(F)cc2nc3c(c4c2c1CCC4N)Cn1c-3cc2c(c1=O)COC(=O)[C@]2(O)CC] |

TABLE 1B-continued
| No. | Structure |
| --- | --- |
| B-3 | 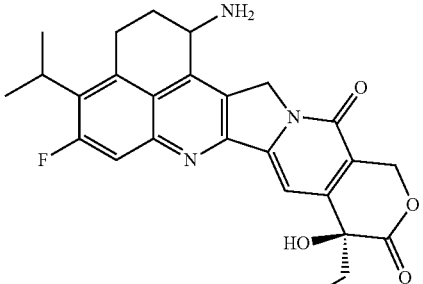 |
| B-4 | 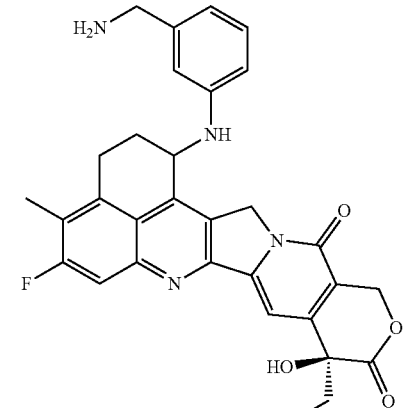 |
| B-5 | 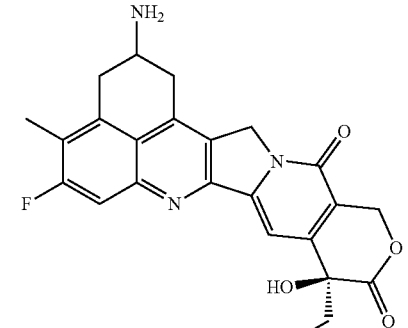 |
In some embodiments, provided is compound selected from Table 1C, or a pharmaceutically acceptable salt or solvate thereof:
TABLE 1C
| No. | Structure |
| --- | --- |
| C-1a | 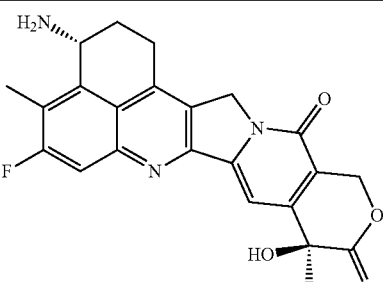 |
TABLE 1C-continued
| No. | Structure |
| --- | --- |
| C-1b | 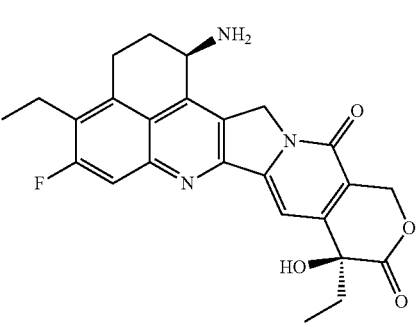 [SMILES: CCc1c(F)cc2nc3c(c4c2c1CC[C@H]4N)Cn1c-3cc2c(c1=O)COC(=O)[C@]2(O)CC] |
| C-2a | 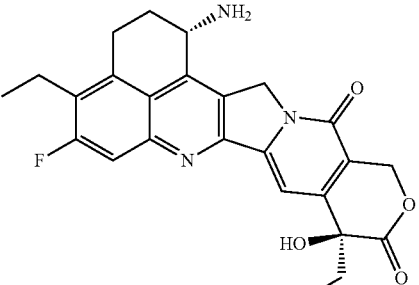 |
| C-2b | 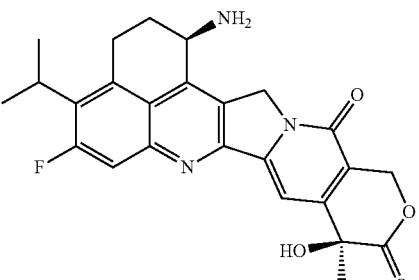 |
| C-3a | 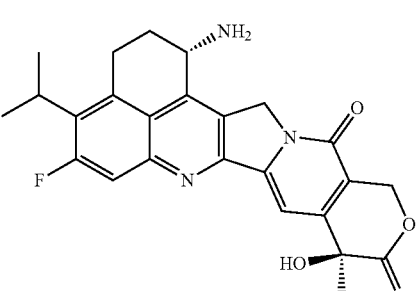 |
| C-3b | 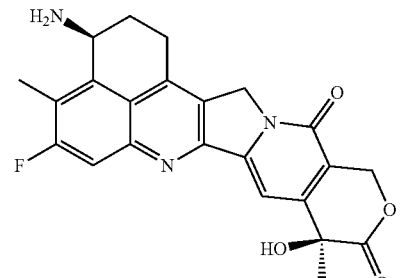 |

TABLE 1C-continued
| No. | Structure |
|---|---|
| C-4a | 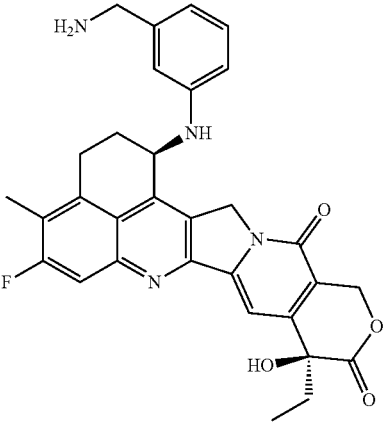 [SMILES: CC[C@@]1(O)C(=O)OCc2c1cc1n(c2=O)Cc2c-1nc1cc(F)c(C)c3c1c2[C@H](Nc1cccc(CN)c1)CC3] |
| C-4b | 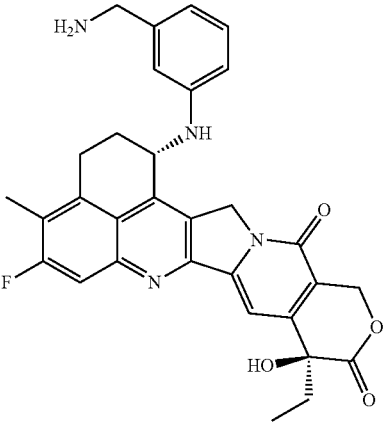 [SMILES: CC[C@@]1(O)C(=O)OCc2c1cc1n(c2=O)Cc2c-1nc1cc(F)c(C)c3c1c2[C@@H](Nc1cccc(CN)c1)CC3] |
| C-5a | 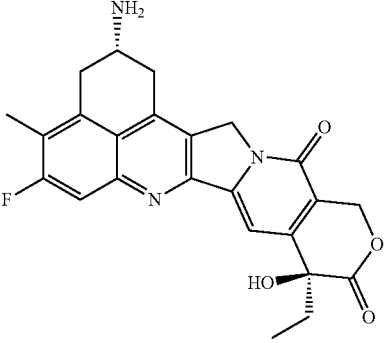 [SMILES: CC[C@@]1(O)C(=O)OCc2c1cc1n(c2=O)Cc2c-1nc1cc(F)c(C)c3c1c2C[C@@H](N)C3] |
| C-5b | 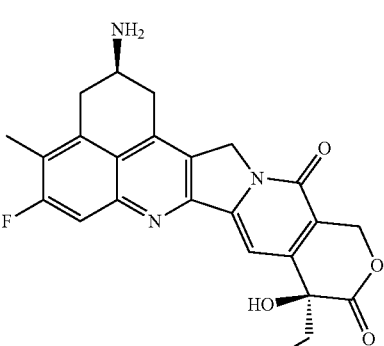 |
In some embodiments, provided is compound selected from Table 1D, or a pharmaceutically acceptable salt or solvate thereof:
TABLE 1D
| No. | Structure |
|---|---|
| D-1 | 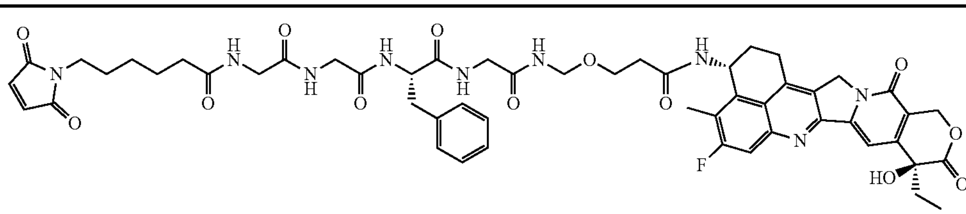 |
| D-2 | 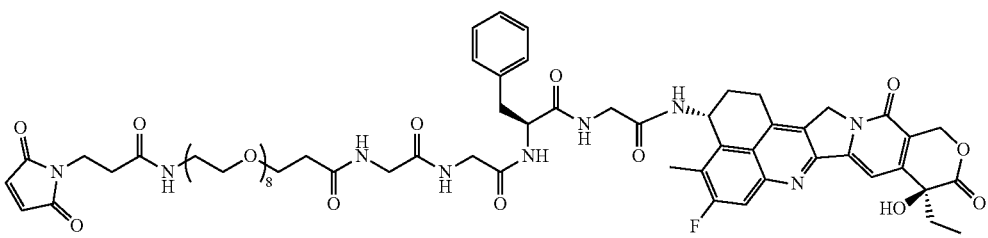 |

TABLE 1D-continued

| No. | Structure |
|---|---|
| D-3 | 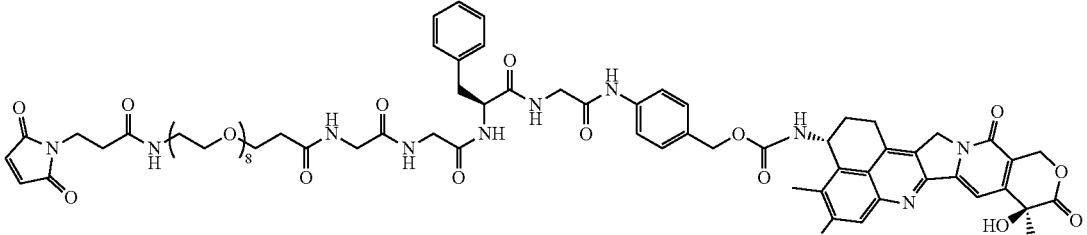 |

The compounds of Formula I include pharmaceutically acceptable salts thereof. In addition, the compounds of Formula I also include other salts of such compounds which are not necessarily pharmaceutically acceptable salts, and which may be useful as intermediates for preparing and/or purifying compounds of Formula I and/or for separating enantiomers of compounds of Formula I.

Pharmaceutical Compositions, Modes of Administration, and Method of Use

Compounds provided herein are usually administered in the form of pharmaceutical compositions. In addition to the active compound, the pharmaceutical composition described in this application may contain one or more excipients, and the excipients may be selected from the following group of ingredients: fillers (diluents), binders, wetting agents, disintegrating agents Solvents and excipients, etc. Depending on the method of administration, the composition may contain from 0.1 to 99% by weight of active compound.

The pharmaceutical compositions may be in the form of sterile injectable aqueous solutions. Among the acceptable vehicles or solvents that may be employed are water, Ringer's solution and isotonic sodium chloride solution. The sterile injectable preparation may be a sterile injectable oil-in-water microemulsion in which the active ingredient is dissolved in an oily phase. For example, the active ingredient is dissolved in a mixture of soybean oil and lecithin. The oil solution can then be treated to form a microemulsion by adding it to a mixture of water and glycerol. Injections or microemulsions can be injected into a patient's bloodstream by local bolus injection. Alternatively, solutions and microemulsions can be administered in a manner that maintains a constant circulating concentration of the compounds of the application. To maintain this constant concentration, a continuous intravenous drug delivery device can be used. For example, the device may be a Deltec CADD-PLUS™ 5400 IV pump.

The pharmaceutical compositions may be in the form of sterile injectable aqueous or oily suspensions for intramuscular and subcutaneous administration. This suspension may be formulated according to the known art using those suitable dispersing or wetting agents and suspending agents which have been mentioned herein above. The sterile injectable preparation may also be a sterile injectable solution or suspension in a non-toxic parenterally acceptable diluent or solvent. Alternatively, sterile fixed oils are conveniently employed as a solvent or suspending medium.

The compounds described herein may have in vivo tumor suppressive effects. Tumor cells with high expression of the specific target may include, but are not limited to, solid tumor cells. For example, tumor cells with high expression of the specific target include but are not limited to gastric cancer cells, or breast cancer cells, such as those with high expression of the specific target.

The compounds described herein may have in vivo tumor targeting capabilities. The in vivo targeting ability may refer to administering the compound labeled with a signal substance to an animal, and the distribution of the labeled compound in the tumor tissue of the animal may be increased by more than 1% compared to other tissues and organs, or 2% or more, 4% or more, 5% or more, 8% or more, 10% or more, 15% or more, 18% or more, 20% or more, 25% or more, 40% or more, 50% or more, 60% or more, 70% or more, 80% or more, 90% or more, or 95% or more, or may be a distribution increase of more than 1.1 times, more than 1.3 times, more than 1.5 times, more than twice, more than three times, more than five times, more than ten times, two times more, more than ten times, more than twenty-two times, more than thirty times, more than fifty times, more than one hundred times, more than five hundred times, more than one thousand times, or more than one thousand five hundred times. The signal substance may be a radioactive substance, for example, the signal substance includes but is not limited to 125I. The animals may include, but are not limited to, mammals, for example, the animals may include, but are not limited to, cats, dogs, horses, pigs, cows, sheep, rabbits, mice, rats, monkeys, or humans. The administration may include, but is not limited to, oral, intravenous, intravenous drip, intraperitoneal, or topical administration. The tissue or organ may include, but is not limited to, heart, liver, spleen, lung, kidney, brain, or bone marrow.

The compounds disclosed herein, including the antibody-drug conjugates, are designed to exhibit cytotoxic activity against cancer cells, and thus, can be used to treat cancer. Accordingly, provided herein are methods for treating cancer in a patient in need thereof, comprising administering to said patient a therapeutically acceptable amount of a compound as described herein, or a stereoisomer or pharmaceutically acceptable salt thereof, or a pharmaceutical composition comprising the same.

The terms "treat," "treating," and "treatment," in the context of treating a disease, disorder, or condition, are meant to include alleviating or abrogating a disorder, disease, or condition, or one or more of the symptoms associated with the disorder, disease, or condition; or to slowing the progression, spread or worsening of a disease, disorder or condition or of one or more symptoms thereof. The term "preventing," as used herein, is the prevention of the onset, recurrence or spread, in whole or in part, of the disease or condition as described herein, or a symptom thereof.

The terms "subject," "patient," or "individual," as used herein, are used interchangeably and refers to any animal, including mammals such as mice, rats, other rodents, rabbits, dogs, cats, swine, cattle, sheep, horses, primates, and humans. In some embodiments, the term refers to a subject, particularly a mammalian subject, for whom diagnosis, prognosis, or therapy is desired or needed. In some embodiments, the subject is a human. In some embodiments, the subject has experienced and/or exhibited at least one symptom of the disease, disorder, or condition to be treated and/or prevented.

Exemplary cancers include, but are not limited to, lung cancer, kidney cancer, urethral cancer, colorectal cancer, prostate cancer, glioblastoma multiforme, ovarian cancer, pancreatic cancer, breast cancer, melanoma, liver cancer, bladder cancer, stomach cancer, and esophageal cancer.

Also provided herein are methods for treating, preventing, or inhibiting tumor growth in a patient in need thereof, comprising administering to said patient a therapeutically acceptable amount of a compound as described herein, or a stereoisomer or pharmaceutically acceptable salt thereof, or a pharmaceutical composition comprising the same.

The compounds as described herein, or a stereoisomer or pharmaceutically acceptable salt thereof, can be administered as a pharmaceutical composition containing at least one pharmaceutically suitable ingredient.

For example, the pharmaceutical composition above may contain at least one pharmaceutical carrier (for example, sterilized liquid), for example, water and oil (petroleum oil and oil of animal origin, plant origin, or synthetic origin (the oil may be, for example, peanut oil, soybean oil, mineral oil, sesame oil or the like)). Water is a more typical carrier when the pharmaceutical composition above is intravenously administered. Saline solution, an aqueous dextrose solution, and an aqueous glycerol solution can be also used as a liquid carrier, e.g., for an injection solution. A suitable pharmaceutical vehicle is known in the art. If desired, the composition may also contain a trace amount of a moisturizing agent, an emulsifying agent, or a pH buffering agent. Examples of suitable pharmaceutical carrier are disclosed in "Remington's Pharmaceutical Sciences" by E. W. Martin. The formulations correspond to an administration mode.

Various delivery systems are known and they can be used for administering the compounds as described herein, or a stereoisomer or pharmaceutically acceptable salt thereof. Examples of the administration route include intradermal, intramuscular, intraperitoneal, intravenous, and subcutaneous routes, but not limited thereto. The administration can be made by injection or bolus injection, for example. In certain embodiments, the administration is performed by injection, e.g., parenteral administration.

In some embodiments, the pharmaceutical composition is prescribed, as a pharmaceutical composition suitable for intravenous administration to human, according to the conventional procedures. The composition for intravenous administration is typically a solution in a sterile and isotonic aqueous buffer solution. If necessary, the pharmaceutical composition may contain a solubilizing agent and local anesthetics to alleviate pain at injection site (for example, lignocaine). Generally, the ingredient above is provided individually as any one of lyophilized powder or an anhydrous concentrate contained in a container which is obtained by sealing in an ampoule or a sachet having an amount of the active agent or as a mixture in a unit dosage form. When the pharmaceutical composition is to be administered by injection, it may be administered from an injection bottle containing water or saline of sterile pharmaceutical grade. When the pharmaceutical composition is administered by injection, an ampoule of sterile water or saline for injection may be provided such that the aforementioned ingredients are admixed with each other before administration.

In some embodiments, the pharmaceutical composition may be a pharmaceutical composition containing only a compound as described herein, or a stereoisomer or pharmaceutically acceptable salt thereof, or a pharmaceutical composition containing a combination of a compound as described herein, or a stereoisomer or pharmaceutically acceptable salt thereof, and at least one cancer treating agent other than the conjugate.

Accordingly, in some embodiments, the compounds as described herein, or a stereoisomer or pharmaceutically acceptable salt thereof, can be administered with other cancer treating agent. The anti-cancer effect may be enhanced accordingly. Another anti-cancer agent used for such purpose may be administered to an individual simultaneously with, separately from, or subsequently to the compound, and it may be administered while varying the administration interval for each. Examples of the cancer treating agent include abraxane, carboplatin, cisplatin, gemcitabine, irinotecan (CPT-11), paclitaxel, pemetrexed, sorafenib, vinorelbine, LH-RH analogues (leuprorelin, goserelin, or the like), estramustine phosphate, estrogen antagonist (tamoxifen, raloxifene, or the like), and an aromatase inhibitor (anastrozole, letrozole, exemestane, or the like), but it is not limited as long as it is a drug having an antitumor activity.

The pharmaceutical composition can be formulated into a lyophilization formulation or a liquid formulation as a formulation having desired composition and required purity. When formulated as a lyophilization formulation, it may be a formulation containing suitable formulation additives that are used in the art. Also for a liquid formulation, it can be formulated as a liquid formulation containing various formulation additives that are used in the art.

Composition and concentration of the pharmaceutical composition may vary depending on administration method. However, the compound contained in the pharmaceutical composition can exhibit the pharmaceutical effect even at a small dosage when the compound has higher affinity for an antigen, that is, higher affinity (=lower Kd value) in terms of the dissociation constant (that is, Kd value) for the antigen. Thus, for determining dosage of the compound, the dosage can be determined in view of a situation relating to the affinity between the compound and antigen. When the compound is administered to a human, for example, about 0.001 to 100 mg/kg can be administered once or administered several times with an interval of one time for 1 to 180 days. In another aspect, the application provides a compound described herein or a tautomer, meso, racemate, enantiomer, diastereomer, or a mixture thereof, or a mixture thereof, Use of a compound or pharmaceutically acceptable salt thereof, or a pharmaceutical composition thereof in the preparation of a medicament for treating and/or preventing tumors. The tumor may be selected from tumors associated with expression of HER2, HER3, B7H3, TROP2, Claudin 18.2, CD30, CD33, CD70 or EGFR. The tumor may be selected from the group consisting of lung cancer, kidney cancer, urethral cancer, colorectal cancer, prostate cancer, glioblastoma multiforme, ovarian cancer, pancreatic cancer, breast cancer, melanoma, liver cancer, bladder cancer, gastric, and esophageal cancer.

The tumor may be selected from tumors associated with the expression of HER2, HER3, B7H3, TROP2, Claudin 18.2, CD30, CD33, CD70, or EGFR. The tumor may be selected from the group consisting of lung cancer, kidney cancer, urethral cancer, colorectal cancer, prostate cancer, glioblastoma multiforme, ovarian cancer, pancreatic cancer, breast cancer, melanoma, liver cancer, bladder cancer, gastric, and esophageal cancer.

In certain embodiments, provided is a compound as described herein, or a stereoisomer or pharmaceutically acceptable salt thereof, for use in the treatment and/or prevention of tumors. In some embodiments, the tumor may be selected from a tumor associated with expression of HER2, HER3, B7H3, TROP2, Claudin 18.2, CD30, CD33, CD70 or EGFR. The tumor may be selected from the group consisting of lung cancer, kidney cancer, urethral cancer, colorectal cancer, prostate cancer, glioblastoma multiforme, ovarian cancer, pancreatic cancer, breast cancer, melanoma, liver cancer, bladder cancer, gastric, and esophageal cancer.

In some embodiments, the compound comprises an antibody or antigen-binding fragment which targets a tumor cell.

In some embodiments, the compound comprises an antibody or antigen-binding fragment which is an anti-A33 antibody or antigen-binding fragment, an anti-B7-H3 antibody or antigen-binding fragment, an anti-CanAg antibody or antigen-binding fragment, an anti-CD20 antibody or antigen-binding fragment, an anti-CD22 antibody or antigen-binding fragment, an anti-CD30 antibody or antigen-binding fragment, an anti-CD33 antibody or antigen-binding fragment, an anti-CD56 antibody or antigen-binding fragment, an anti-CD70 antibody or antigen-binding fragment, an anti-CEA antibody or antigen-binding fragment, an anti-Cripto antibody or antigen-binding fragment, an anti-EphA2 antibody or antigen-binding fragment, an anti-G250 antibody or antigen-binding fragment, an anti-MUC1 antibody or antigen-binding fragment, an anti-GPNMB antibody or antigen-binding fragment, an anti-integrin antibody or antigen-binding fragment, an anti-PSMA antibody or antigen-binding fragment, an anti-tenascin-C antibody or antigen-binding fragment, an anti-SLC44A4 antibody or antigen-binding fragment, or an anti-mesothelin antibody or antigen-binding fragment.

In some embodiments, the compound comprises an antibody or antigen-binding fragment which is an anti-B7-H3 antibody or antigen-binding fragment, an anti-CD30 antibody or antigen-binding fragment, an anti-CD33 antibody or antigen-binding fragment, or an anti-CD70 antibody or antigen-binding fragment.

In some embodiments, the compound comprises an antibody or antigen-binding fragment which is an anti-B7-H3 antibody or antigen-binding fragment.

The terms "antibody" or "antigen-binding fragment" as used herein refer to an immunoglobulin and is a molecule containing an antigen-binding site immunospecifically binding to an antigen. The class of the antibody or antigen-binding fragment may be any of IgG, IgE, IgM, IgD, IgA, and IgY and is preferably IgG. The subclass of the antibody or antigen-binding fragment may be any of IgG1, IgG2, IgG3, IgG4, IgA1, and IgA2 and is preferably IgG1 or IgG2. The antibody or antigen-binding fragment may be derived from any species, including humans, rats, mice, or rabbits. In cases where the antibody or antigen-binding fragment is derived from a species other than human, it may be chimerized or humanized using well known techniques. The antibody or antigen-binding fragment may be a polyclonal antibody or a monoclonal antibody. In some embodiments, the antibody or antigen-binding fragment is a monoclonal antibody.

The antibody or antigen-binding fragment may be capable of targeting tumor cells. Since the antibody or antigen-binding fragment is conjugated with a drug or payload having antitumor activity via a linker, the antibody can possess one or more of a property of recognizing a tumor cell, a property of binding to a tumor cell, a property of internalizing in a tumor cell, or a property of damaging a tumor cell.

The binding activity of the antibody or antigen-binding fragment against tumor cells can be confirmed using flow cytometry. The internalization of the antibody or antigen-binding fragment into tumor cells can be confirmed using (1) an assay of visualizing an antibody or antigen-binding fragment incorporated in cells under a fluorescence microscope using a secondary antibody (fluorescently labeled) binding to the therapeutic antibody (Cell Death and Differentiation (2008) 15, 751-761), (2) an assay of measuring the amount of fluorescence incorporated in cells using a secondary antibody (fluorescently labeled) binding to the antibody or antigen-binding fragment (Molecular Biology of the Cell, Vol. 15, 5268-5282, December 2004), or (3) a Mab-ZAP assay using an immunotoxin binding to the antibody or antigen-binding fragment wherein the toxin is released upon incorporation into cells to inhibit cell growth (Bio Techniques 28: 162-165, January 2000).

For example, the tumor may be selected from tumors associated with expression of the following group: 5T4, AGS-16, ANGPTL4, ApoE, CD19, CTGF, CXCR5, FGF2, MCPT8, MFI2, MS4A7, NCA, Sema5b, SLITRK6, STC2, TGF, 0772P, 5T4, ACTA2, ADGRE1, AG-7, AIF1, AKR1C1, AKR1C2, ASLG659, Axl, B7H3, BAFF-R, BCMA, BMPR1B, BNIP3, C1QA, C1QB, CA6, CADM1, CCD79b, CCL5, CCR5, CCR7, CD11c, CD123, CD138, CD142, CD147, CD166, CD19, CD19, CD22, CD21, CD20, CD205, CD22, CD223, CD228, CD25, CD30, CD33, CD37, CD38, CD40, CD45, CD45 (PTPRC), CD46, CD47, CD49D (ITGA4), CD56, CD66e, CD70, CD71, CD72, CD74, CD79a, CD79b, CD80, CDCP1, CDH11, CD11b, CEA, CEACAM5, c-Met, COL6A3, COL7A1, CRIPTO, CSF1R, CTSD, CTSS, CXCL11, CXCL10, DDIT4, DLL3, DLL4, DR5, E16, EFNA4, EGFR, EGFRvIII, EGLN, EGLN3, EMR2, ENPP3, EpCAM, EphA2, EphB2R, ETBR, FcRH2, FcRH1, FGFR2, FGFR3, FLT3, FOLR-α, GD2, GEDA, GPC-1, GPNMB, GPR20, GZMB, HER2, HER3, HLA-DOB, HMOX1, IF16, IFNG, IGF-1R, IGFBP3, IL10RA1, IL-13R, IL-2, IL20Ra, IL-3, IL-4, IL-6, IRTA2, KISSIR, KRT33A, LIV-1, LOX, LRP-1, LRRC15, LUM, LY64, LY6E, Ly86, LYPD3, MDP, MMP10, MMP14, MMP16, MPF, MSG783, MSLN, MUC-1, *NaPi*2b, *Napi*3b, Nectin-4, Nectin-4, NOG, P2X5, pCAD, P-Cadherin, PDGFRA, PDK1, PD-L1, PFKFB3, PGF, PGK1, PIK3AP1, PIK3CD, PLOD2, PSCA, PSCAhlg, PSMA, PSMA, PTK7, P-Cadherin, RNF43, NaPi2b, ROR1, ROR2, SERPINE1, SLC39A6, SLTRK6, STAT1, STEAP1, STEAP2, TCF4, TENB2, TGFB1, TGFB2, TGFBR1, TNFRSF21, TNFSF9, Trop-2, TrpM4, Tyro7, UPK1B, VEGFA, WNT5A, epidermal growth factor, glycan, mesothelin, sodium phosphate cotransporter 2B, occludin 18.2, endothelin receptor, mucin (eg mucin 1 and mucin 16), guanylate cyclase C, integrin a4p7, integrin a5p6, trophoblast glycoprotein and tissue factor.

Dosing

The specific dose level of a compound of the present application for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound described herein per kilogram of the subject's body weight (mg/kg). Dosages of between about 0.1 and 150 mg/kg may be appropriate. In some embodiments, about 0.1 and 100 mg/kg may be appropriate. In other embodiments a dosage of between 0.5 and 60 mg/kg may be appropriate. In some embodiments, a dosage of from about 0.0001 to about 100 mg per kg of body weight per day, from about 0.001 to about 50 mg of compound per kg of body weight, or from about 0.01 to about 10 mg of compound per kg of body weight may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

Synthesis of the Compounds

The compounds may be prepared using the methods disclosed herein and routine modifications thereof, which will be apparent given the disclosure herein and methods well known in the art.

Conventional and well-known synthetic methods may be used in addition to the teachings herein. The synthesis of typical compounds described herein may be accomplished as described in the following examples. If available, reagents may be purchased commercially, e.g., from Sigma Aldrich or other chemical suppliers.

General Synthesis

The compounds may be prepared using the methods disclosed herein and routine modifications thereof, which will be apparent given the disclosure herein and methods well known in the art. Conventional and well-known synthetic methods may be used in addition to the teachings herein. The synthesis of typical compounds described herein may be accomplished as described in the following examples. If available, reagents and starting materials may be purchased commercially, e.g., from Sigma Aldrich or other chemical suppliers.

It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in Wuts, P. G. M., Greene, T. W., & Greene, T. W. (2006). Greene's protective groups in organic synthesis. Hoboken, N.J., Wiley-Interscience, and references cited therein.

Furthermore, the compounds of this disclosure may contain one or more chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wisconsin, USA), Bachem (Torrance, California, USA), Emka-Chemce or Sigma (St. Louis, Missouri, USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

The compounds described herein can be prepared according to the Schemes that follow.

Scheme I shows the preparation of compounds of Formula I where $R^1$, $R^2$, or $R^3$ is hydrogen. In Scheme I, $R^4$ is as defined herein, and PG is a protecting group (e.g., Ac).

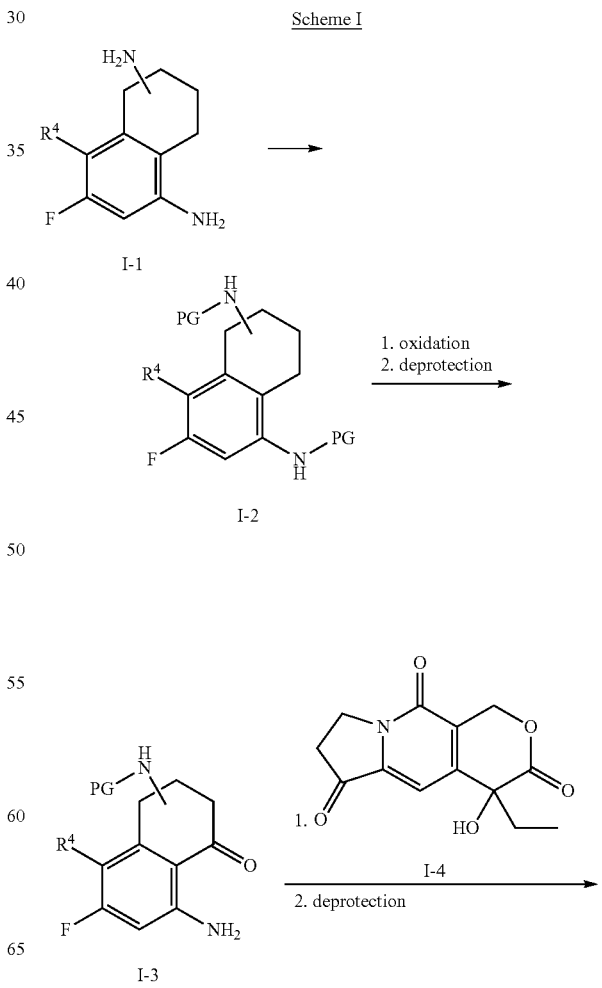

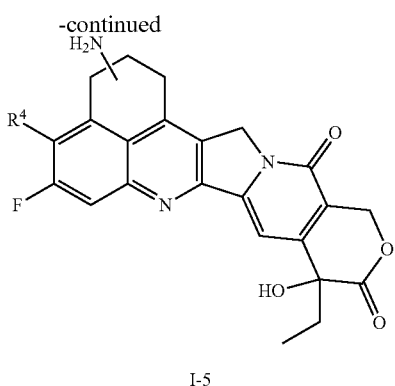

I-5

In Scheme I, compounds of Formula II-2 are provided by protecting compound I-1 using a suitable amine protecting group (e.g., an acetyl halide). Oxidation of compound I-2, followed by selective deprotection affords compound I-3. Contacting compound I-3 with compound I-4, followed by deprotection affords compounds of Formula I-5 (i.e., compounds of Formula I wherein $R^1$, $R^2$, or $R^3$ is hydrogen)

Scheme II shows the preparation of additional compounds of Formula I. In Scheme II, x, $R^4$ and $R^5$ are as defined herein, Ab is an antibody or antigen-binding fragment, and LG is a leaving group (e.g., —OH, -alkoxy, halo, etc.).

In Scheme II, compounds of Formula II-2 are provided by contacting compound I-5 with compound II-1 under standard amide bond forming reaction conditions. Antibody drug conjugates of Formula II-3 can be provided from compounds of Formula II-2 where $R^5$ comprises a suitable functional group for bonding to an amino acid side chain of an antibody or antigen-binding fragment (e.g., compounds wherein $R^6$ is a pyrrole-2,5-dion-1-yl) under conditions known in the art. Compounds of Formula II-4 (e.g., Formula I where $R^1$ is —$C_6$ aryl-$C_{1-6}$ alkyl-$NH_2$) are provided from compound I-5 by contacting compound I-5 with a suitable arylating reagent (e.g., tris(3-(((tert-butyldimethylsilyl)oxy)methyl)phenyl)bismuthane, followed by deprotection and amination. Acylation of compound II-4 using compound II-1 under standard amide bond forming reaction conditions provides compound II-5. Antibody drug conjugates of Formula II-6 can be provided from compounds of Formula II-5 where $R^5$ comprises a suitable functional group for bonding to an amino acid side chain of an antibody or antigen-binding fragment (e.g., compounds wherein $R^6$ is a pyrrole-2,5-dion-1-yl) under conditions known in the art.

Appropriate starting materials and reagents can be purchased or prepared by methods known to one of skill in the art. Upon each reaction completion, each of the intermediate or final compounds can be recovered, and optionally purified, by conventional techniques such as neutralization, extraction, precipitation, chromatography, filtration and the like.

Scheme II

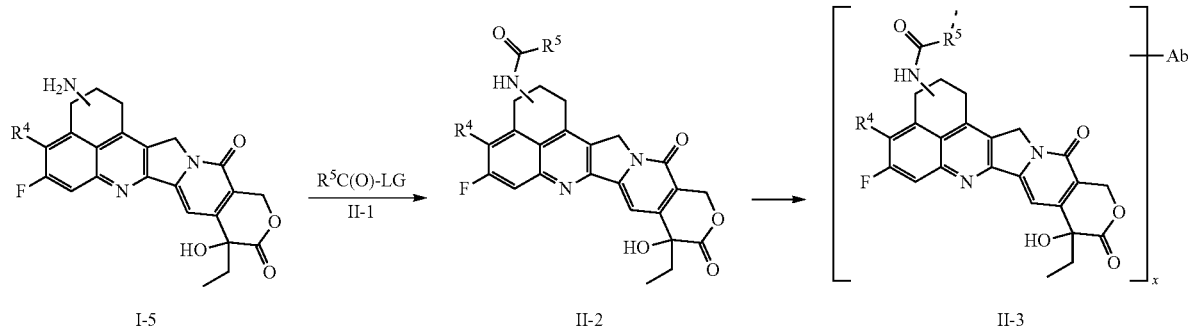

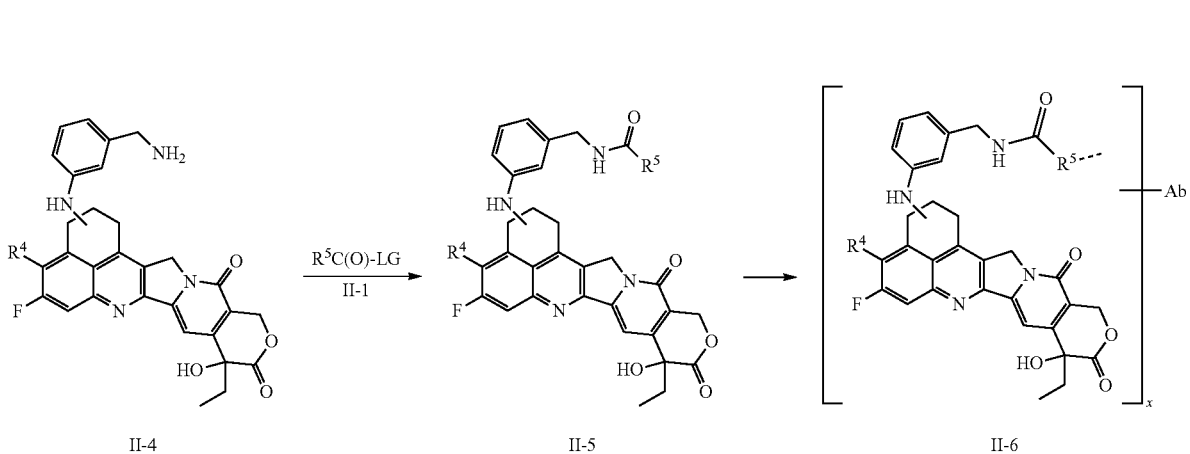

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

Example 1: Synthesis of Compounds C-1a and C-1b

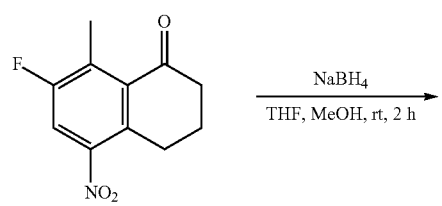

1-1

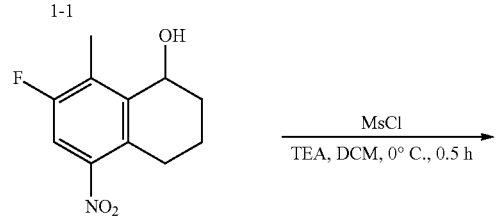

1-2

1-3

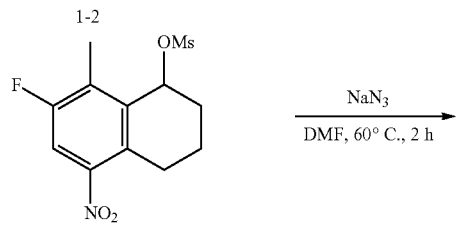

1-4

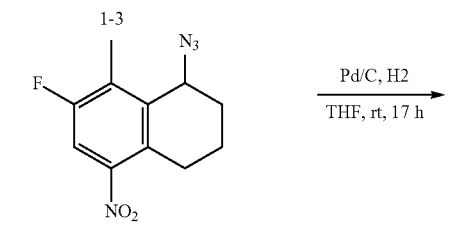

1-5

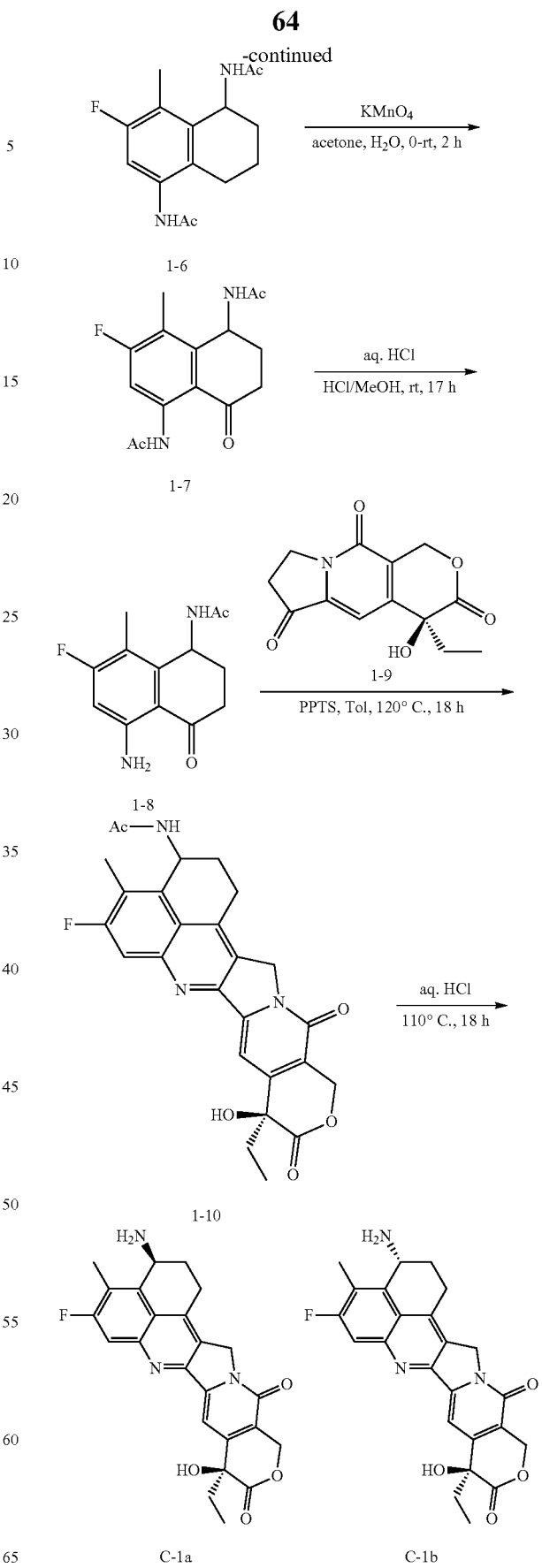

1-6

1-7

1-8

1-9

1-10

C-1a

C-1b

The Preparation of Compound 1-2

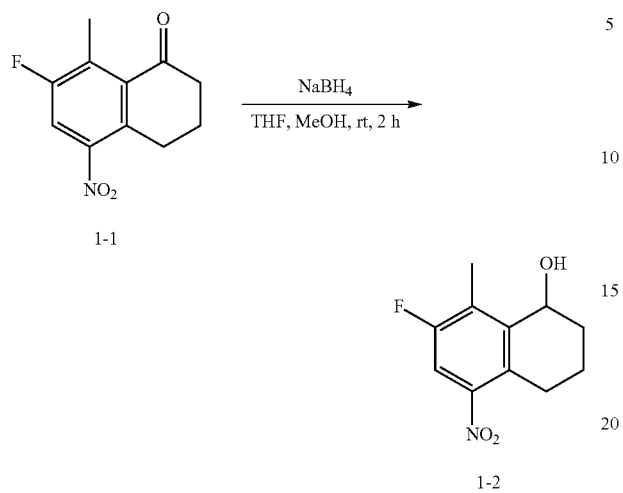

To a solution of Compound 1-1 (3 g, 13.5 mmol) in THF (15 mL) and MeOH (15 mL), NH$_4$HCO$_2$ (5.09 g, 80.7 mmol) and NaBH$_4$ (2.55 g, 67.4 mmol) were added, and the reaction solution reacted at room temperature for 2 h. The reaction was monitored by LCMS. When the raw materials disappeared, the reaction was complete. At the end of the reaction, white solids were precipitated and filtered from the reaction solution to obtain 2.9 g of Compound 1-2. LCMS (m/z) [M+H]$^+$=208.0.

The Preparation of Compound 1-3

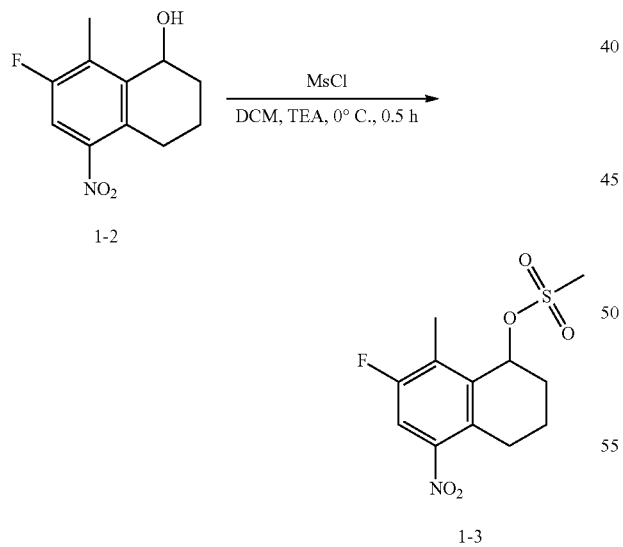

Compound 1-2 (3.0 g, 13.3 mmol) was placed in a reaction flask and dissolved in DCM (30 mL), cooled with ice ethanol, added with TEA (6.75 g, 66.7 mmol), and stirred for 10 min, followed by the slow dropwise addition of MsCl (4.12 g, 36.0 mmol) and stirred for half an hour. Completion of reaction was monitored by LCMS. The reaction solution was extracted with water (50 mL) and DCM (3×50 mL). The organic phase was collected, washed with saturated salt water, dried over anhydrous sodium sulfate, and concentrated at a low temperature to obtain 2.91 g of Compound 1-3. LCMS (m/z) [M−95]$^+$=208.0.

The Preparation of Compound 1-4

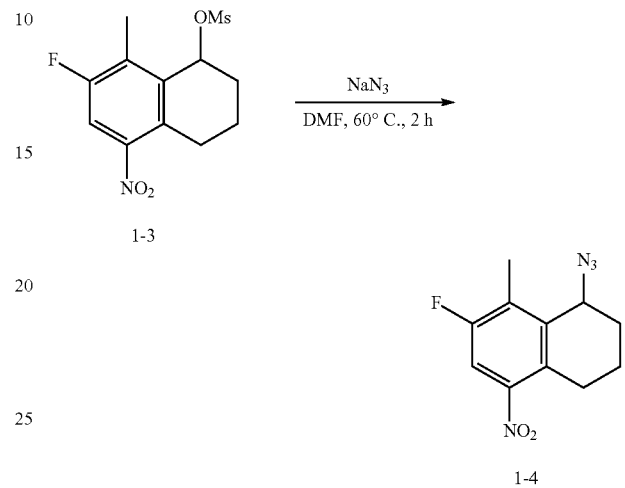

Compound 1-3 (2.91 g, 9.6 mmol) and NaN$_3$ (1.24 g, 19.2 mmol) were placed in a reaction flask and added with DMF (30 mL). The reaction solution was warmed to 60° C. and reacted for 2 h. Completion of reaction was monitored by LCMS. The reaction solution was added with water (100 mL) and extracted with EA (3×60 mL). The organic phase was collected, washed with saturated salt water, dried over anhydrous sodium sulfate, and concentrated to obtain Compound 1-4. The yield was not calculated. LCMS (m/z) [M−42]$^+$=208.0, RT: 1.33 min.

The Preparation of Compound 1-5

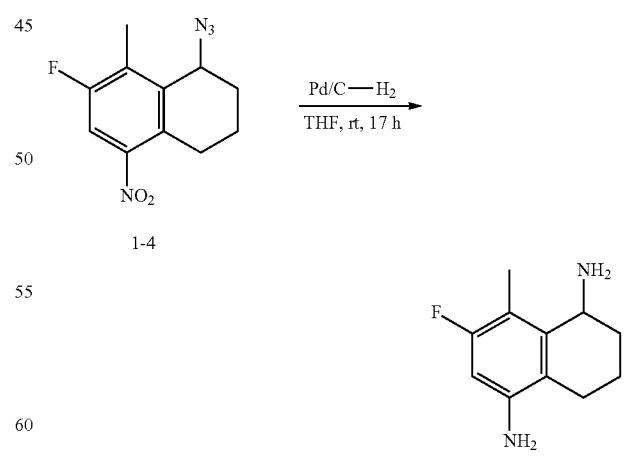

Compound 1-4 (crude) and THF (40 mL) were placed in a reaction flask, added with Pd/C (200 mg) and stirred overnight under H$_2$. Completion of reaction was monitored by LCMS. The reaction solution was filtered and concentrated to obtain 1.4 g of Compound 1-5. The yield is not counted. LCMS (m/z) [M−16]$^+$=178.2, RT: 0.513 min.

The Preparation of Compound 1-6

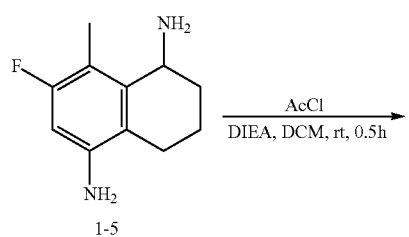

Compound 1-5 (1.4 g, 7.21 mmol) was placed in a reaction flask, added with DCM (14 ml) to dissolve under nitrogen protection, added with DIPEA (2.8 g, 21.6 mmol), and followed by the slow dropwise addition of CH$_3$COCl (1.41 g 18.0 mmol) in an ice-water bath. The reaction solution was reacted with natural warming for 0.5 h. Completion of reaction was monitored by LCMS. The reaction solution was added with water (50 ml) and extracted with DCM (3×50 ml). The organic phase was collected, washed with saturated salt water, dried over anhydrous sodium sulfate and concentrated to obtain 1.6 g of Compound 1-6. The four-step yield was 43%.

The Preparation of Compound 1-7

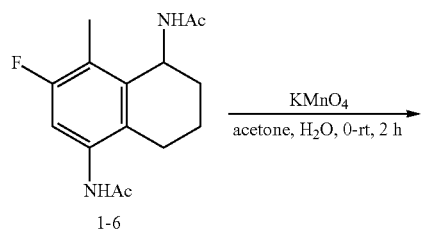

Compound 1-6 (1.46 g, 5.76 mmol) was placed in a reaction flask, added with acetone (16 ml) and 15% MgSO$_4$ (16 ml) aqueous solution to dissolve, followed by the addition of KMnO$_4$ (1.86 g, 11.8 mmol) in batches under nitrogen protection in an ice-water bath at 0° C. The reaction solution was stirred for 1 h under ice-water bath conditions, and stirred for another 1 h with natural warming. Completion of reaction was monitored by LCMS. The reaction solution was filtered and washed with ethyl acetate. The filtrate was extracted with water, and the organic phase was collected, washed with saturated salt water, dried over anhydrous sodium sulfate, concentrated, purified by reversed-phase column (acetonitrile: water was 30%), collected and lyophilized to obtain 800 mg of Compound 1-7. The yield was 48%.

The Preparation of Compound 1-8

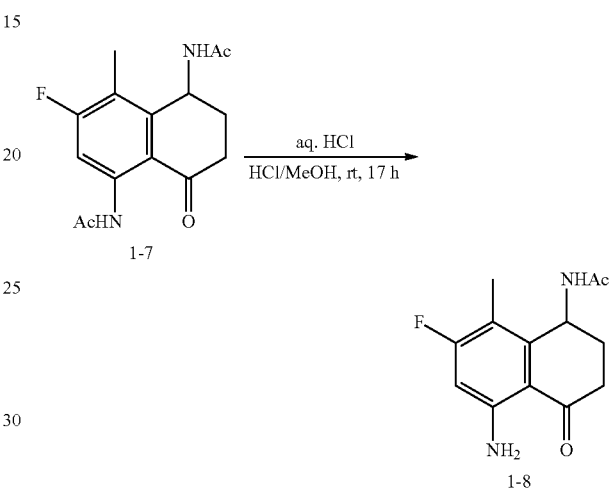

Compound 1-7 (800 mg, 2.74 mmol) was dissolved in a mixture of DCM/MeOH (16 ml/8 ml, 20V/10V), added dropwise with concentrated hydrochloric acid (4.8 ml, 6V) and reacted at 25° C.-30% for 17 h C. The reaction was monitored by TLC. After completion of reaction was monitored by the TLC, the reaction solution was diluted by adding DCM, and the pH was adjusted to 6-7 by slowly adding aqueous sodium hydroxide (0.5 M) dropwise. After the reaction solution was separated, the aqueous phase was extracted with DCM, and the organic phases were combined and washed with saturated salt water, dried over anhydrous sodium sulfate, concentrated, and pulped with methyl tert-butyl ether to obtain 553 mg of Compound 1-8. The yield was 80%.

The Preparation of Compound 1-10

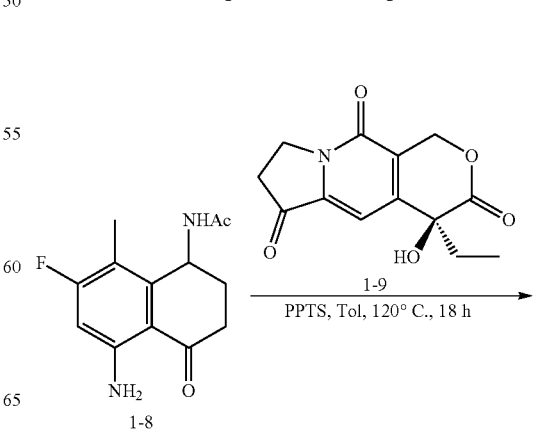

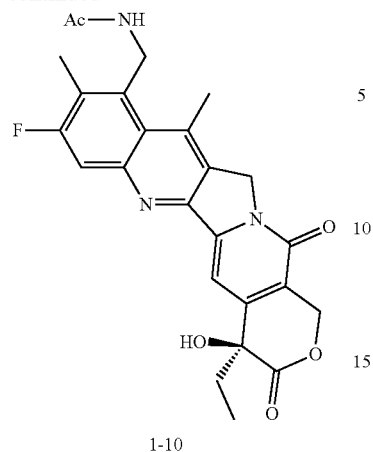

1-10

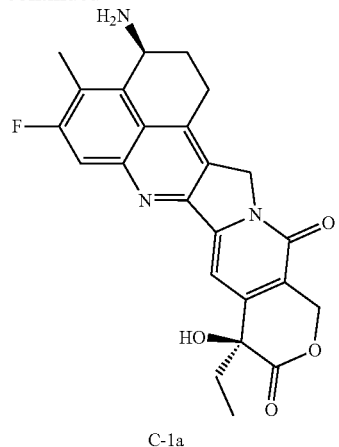

C-1a

Compound 1-8 (230 mg, 0.92 mmol) and Compound 1-9 (220 mg, 0.836 mmol) were placed in a reaction flask, added with toluene (5 ml) to dissolve, followed by the addition of PPTS (150 mg, 0.6 mmol) under nitrogen protection, heated to 120° C., and reacted with reflux for 18 h. Black solids were precipitated from the reaction solution. Completion of reaction was monitored by LCMS. The reaction solution was concentrated and spun dry, and the resulting solids were dissolved by adding DMF, purified by reversed-phase column (acetonitrile: water was 20%), collected and lyophilized to obtain 245 mg of Compound 1-10. The yield was 56%.

The Preparation of Compound C-1a and C-1b

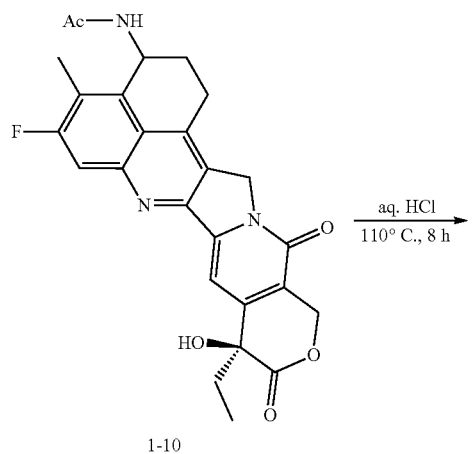

1-10

C-1b

Compound 1-10 (245 mg, 0.51 mmol) was dissolved with aqueous hydrochloric acid (6 mol, 5 ml), heated to 110° C. and reacted with reflux for 8 h. Completion of reaction was monitored by LCMS. The reaction solution was freeze-dried after mixing with water and acetonitrile and removal of hydrochloric acid. Compound C-1a (30 mg) and Compound C-1b (58 mg) were obtained.

Compound C-1a: LCMS (m/z) [M+H]+=436.2. $^1$H NMR (400 MHz, DMSO): δ 8.32 (brs, 3H), 8.00 (d, J=10.8 Hz, 1H), 7.33 (s, 1H), 6.54 (s, 1H), 5.49-5.33 (m, 3H), 5.30-5.13 (m, 2H), 3.31-3.27 (m, 2H), 2.56 (s, 3H), 2.20 (d, J=8.0 Hz, 1H), 1.90-1.80 (m, 2H), 0.89 (t, J=7.2 Hz, 3H).

Compound C-1b: LCMS (m/z) [M+H]+=436.2. $^1$H NMR (400 MHz, DMSO) δ 8.34 (brs, 3H), 8.00 (d, J=10.8 Hz, 1H), 7.34 (s, 1H), 6.53 (s, 1H), 5.51-5.31 (m, 3H), 5.30-5.13 (m, 2H), 3.33-3.25 (m, 2H), 2.56 (s, 3H), 2.25-2.14 (m, 1H), 1.98-1.77 (m, 2H), 0.88 (t, J=7.2 Hz, 3H).

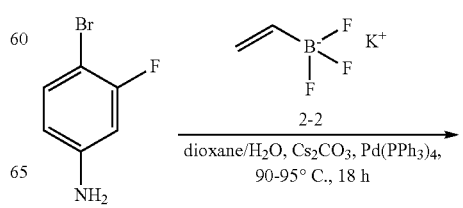

71
-continued
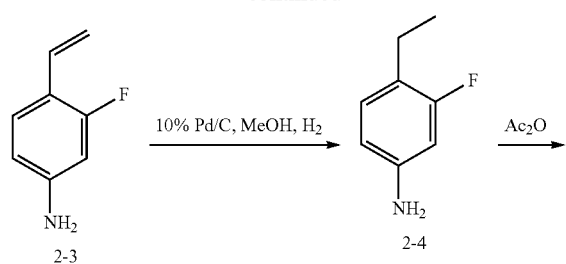
2-3
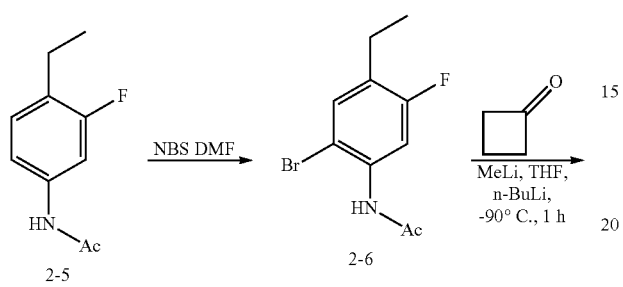
2-5  2-6
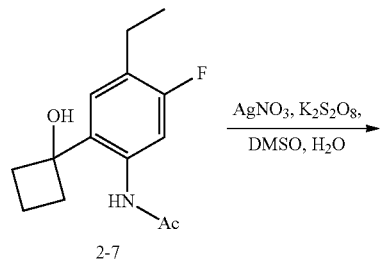
2-7
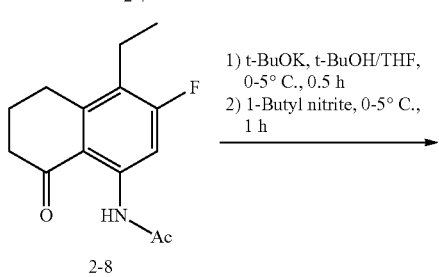
2-8
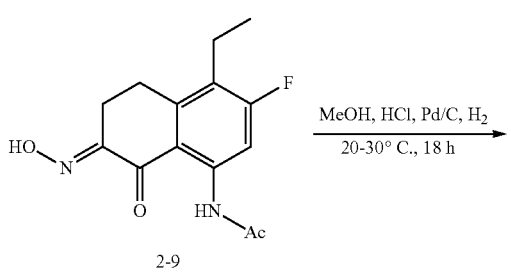
2-9
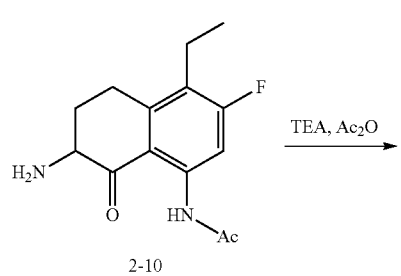
2-10
72
-continued
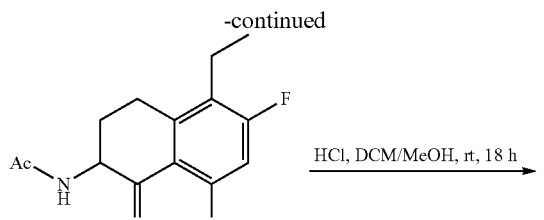
2-11
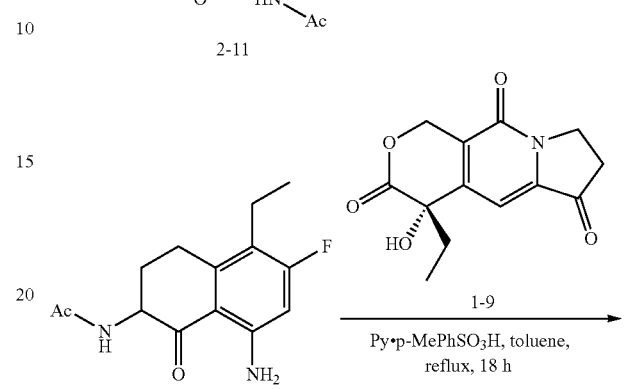
2-12
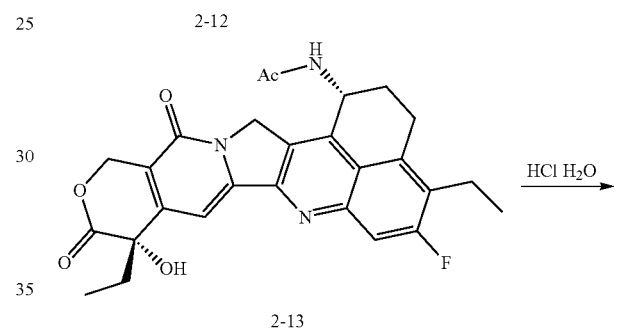
2-13
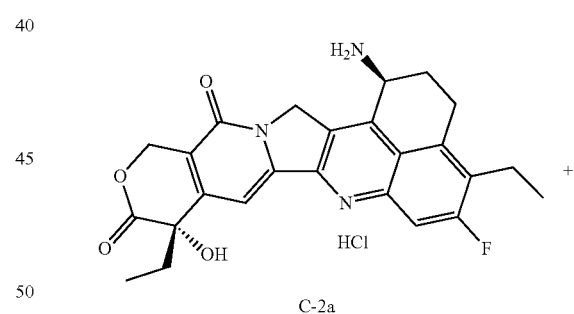
C-2a
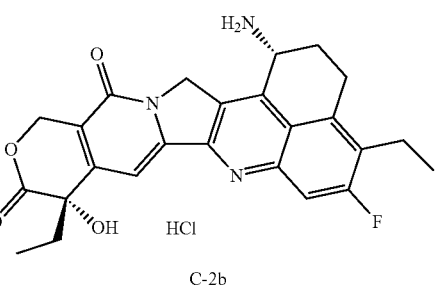
C-2b

The Preparation of Compound 2-3

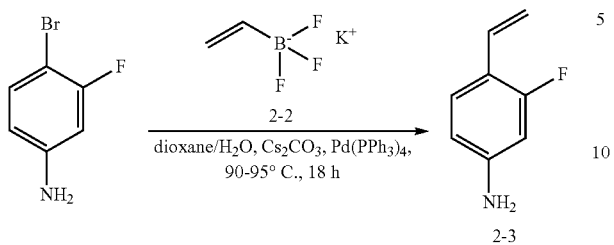

Compound 2-1 (50.0 g, 263 mmol) was dissolved in dioxane (1.2 L) and H$_2$O (300 mL), added with Compound 2-2 (38.8 g, 290 mmol), Cs$_2$CO$_3$ (257 g, 789 mmol), and Pd(PPh$_3$)$_4$ (3.04 g, 2.63 mmol), and reacted at 95° C. for 18 h. The reaction was monitored by LCMS, and the raw materials disappeared. After the reaction was completed, water (500 mL) was added to the reaction solution, followed by extraction with EA (3×200 mL). The organic phases were combined, washed with water (3×300 mL) and saturated sodium chloride (1 L), dried over anhydrous sodium sulfate, filtered, and concentrated to obtain crude product. The crude product was mixed with silica gel and purified by column chromatography (PE/EA) to obtain 32 g of Compound 2-3. The yield was 88%.

The Preparation of Compound 2-4

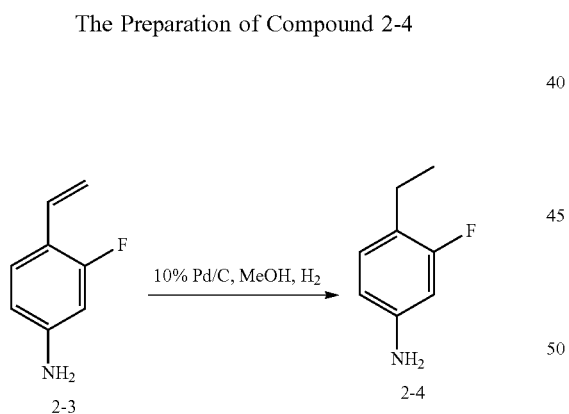

Compound 2-3 (32 g, 233 mmol) was dissolved by adding MeOH (300 mL), followed by the addition of 10% Pd/C (3.2 g), and reacted at room temperature (25° C.) for 18 h. The reaction was monitored by LCMS and the raw material disappeared. The reaction solution was filtered with diatomaceous earth and washed with methanol (1 L). The filtrate was spun dry to obtain 27 g of Compound 2-4. The yield was 84%.

The Preparation of Compound 2-5

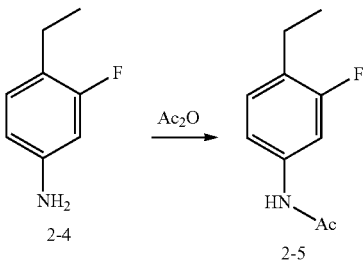

Compound 2-4 (27 g, 194 mmol) was dissolved in DCM (300 mL), added with Ac$_2$O (23.8 g, 232.8 mmol), and stirred at 25° C. for 3 h. TLC (PE/EA=1/1) detected the completion of reaction. After that, water (500 mL) was added to the reaction solution, followed by extraction with DCM (3×200 mL). The organic phases were combined, washed with saturated sodium chloride (1 L), dried over anhydrous sodium sulfate, filtered, and concentrated to obtain 32 g of Compound 2-5. The crude product was directly used in the next step of reaction. The yield was 91%.

The Preparation of Compound 2-6

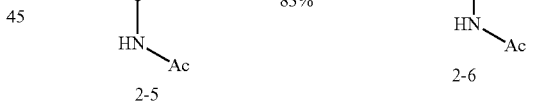

Compound 2.5 (32 g, 182 mmol) was dissolved in DMF (320 mL), followed by the addition of NBS (65 g, 363 mmol), and stirred at 25° C. for 18 h. TLC (PE/EA=1/1) detected the completion of reaction. 500 mL of water was added to the reaction solution, followed by extraction with EA (3×200 mL). The organic phases were combined, washed with water (3×300 mL), washed with saturated sodium chloride (500 mL), dried over anhydrous sodium sulfate, filtered, and concentrated to obtain crude product. The crude product was purified by column chromatography to obtain 38 g of Compound 2-6. The yield was 83%.

The Preparation of Compound 2-7

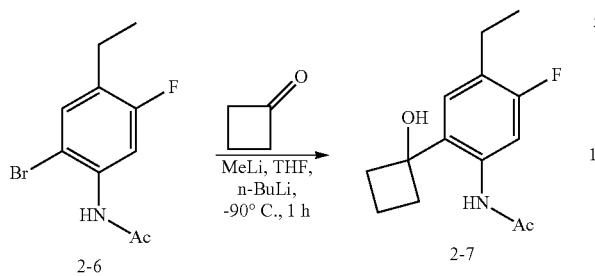

Compound 2-6 (30 g, 119 mmol) was placed in a dry three-necked flask under $N_2$ protection, dissolved by adding 250 mL of THF, cooled to about −90° C., slowly added dropwise 3 M of MeLi solution (60 mL, 179 mmol) while keeping the temperature remain below −80° C., and stirred at the same temperature for 30 min, followed by the slow dropwise addition of 2.5 M of n-BuLi/THF solution (72 mL, 178.8 mmol) and stirred at −90° C. for 30 min. After that, a solution of cyclobutanone (10.1 g, 143 mmol) in THF (50 mL) was slowly added dropwise and stirred at that temperature for 1 h. The reaction was detected by LCMS and 15% of the raw materials were left with the main peak being the product. The reaction was quenched by adding 200 mL of saturated aqueous ammonium chloride to the reaction solution, followed by extraction with EA (3×50 mL). The organic phases were combined, washed with saturated sodium chloride (100 mL), dried over anhydrous sodium sulfate, filtered, and concentrated to obtain crude product. The crude product was purified by column chromatography to obtain 27 g of Compound 2-7. The yield was not counted.

The Preparation of Compound 2-8

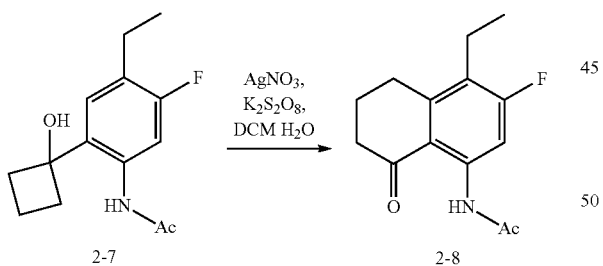

Compound 2-7 (27 g, 107 mmol) was added to DCM (540 mL) and $H_2O$ (540 mL), followed by the addition of $AgNO_3$ (3.65 g, 21.5 mmol) and $K_2S_2O_8$ (87.1 g, 322.3 mmol), and stirred at 25° C. for 18 h. The reaction was detected by LCMS and the raw materials disappeared with the main peak being the product. The reaction was shut down. 1 L of water was added to the reaction solution, followed by extraction with DCM (3×300 mL). The organic phases were combined, washed with saturated sodium chloride (1 L), dried over anhydrous sodium sulfate, filtered and concentrated to obtain crude product. The crude product was mixed with silica gel and purified by column chromatography to obtain 11 g of Compound 2-8. The two-step yield was 38%.

The Preparation of Compound 2-9

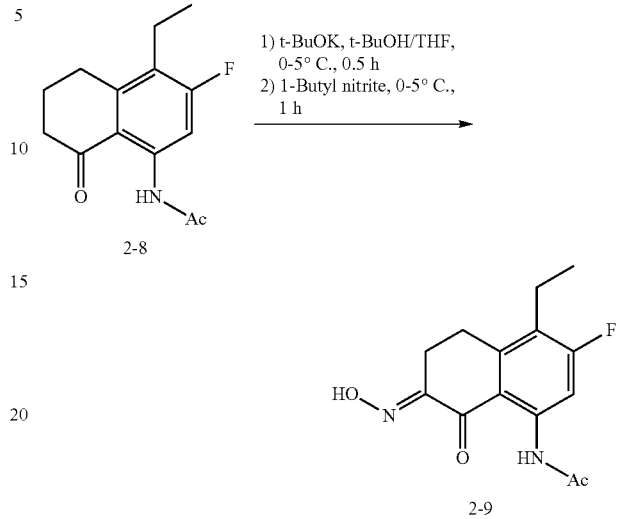

Potassium tert-butoxide (9.45 g, 84.3 mmol) was added to tert-butanol (30 mL) and THF (60 mL) under $N_2$ protection, followed by the slow dropwise addition of a solution of Compound 2-8 (6 g, 24.1 mmol) in THF (60 mL) at about 0° C., and stirred at 0° C. for 30 min, followed by the slow addition of n-butyl nitrite (9.45 g, 84.3 mmol) and stirred at 0° C. for 1 h. TLC (PE/EA=1/1) showed that the reaction was completed. 300 mL of water was added to the reaction solution, followed by the addition of 1 M of HCl to adjust the pH to 2-3. A large amount of solids were precipitated, filtered and washed with water (500 mL). The filter cake was collected, added with 50 mL of PE:MTBE=10:1, stirred at 25° C. for 1 h and filtered, and the filter cake was collected and dried with oil pump to obtain 6.3 g of Compound 2-9. The yield was 94%.

The Preparation of Compound 2-11

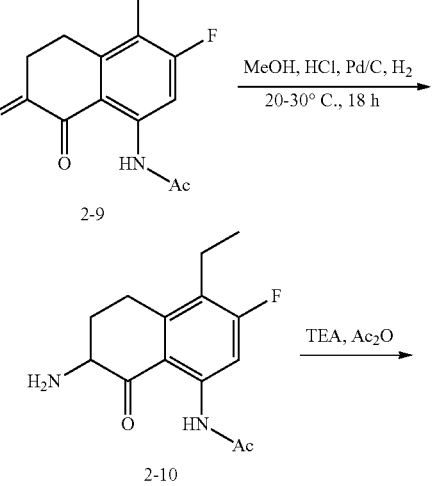

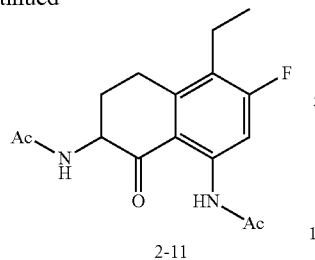

2-11

Compound 2-9 (7.3 g, 26.2 mmol) was dissolved in MeOH (220 mL), added with 4 M of HCl/MeOH (13.2 mL, 52.4 mmol), followed by the addition of 10% Pd/C (730 mg), and stirred at 28° C. for 18 h. The reaction was detected by LCMS and the raw materials disappeared. TEA (9.37 g, 91.8 mmol) and Ac$_2$O (6.16 g, 60.3 mmol) were added to the reaction solution, and stirred at 28° C. for 1 h. The reaction was detected by LCMS, and the raw materials disappeared. The reaction solution was filtered with diatomaceous earth and washed with methanol (1 L). The filtrate was spun dry to obtain crude product. The crude product was purified by column chromatography to obtain 2 g of Compound 2-11. The two-step yield was 25%.

The Preparation of Compound 2-12

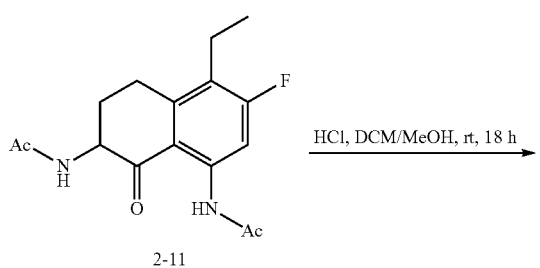

Compound 2-11 (2 g, 6.53 mmol) was added to DCM (40 mL) and MeOH (20 mL), followed by the addition of concentrated hydrochloric acid (12 mL), and stirred at 28° C. for 18 h. The reaction was detected by LCMS and the raw materials disappeared with the main peak being the product. The reaction was shut down. 30 mL of water was added to the reaction solution, followed by the addition of saturated aqueous sodium bicarbonate to adjust the pH to 9-10, followed by extraction with DCM (3×20 mL). The organic phases were combined, washed with saturated sodium chloride (50 mL), dried over anhydrous sodium sulfate, filtered and concentrated to obtain crude product. The filter cake was added with 20 mL of PE:MTBE=10:1, stirred at 25° C. for 1 h and filtered, and the filter cake was collected to obtain 1.7 g of Compound 2-12. The yield was not counted.

The Preparation of Compound 2-13

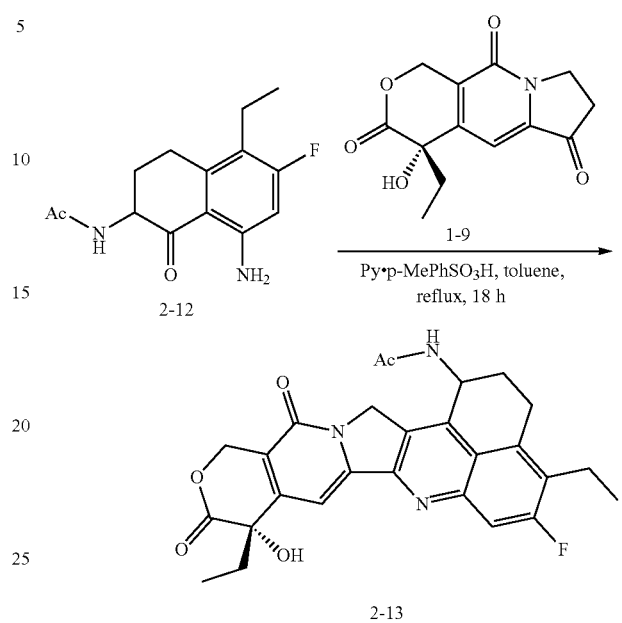

Compound 2-12 (330 mg, 1.25 mmol) was dissolved in toluene (10 mL), added with HM-582_8 (299 mg, 1.14 mmol) and PPTS (143 mg, 0.57 mmol), and stirred at 125° C. for 24 h. The reaction was detected by LCMS and 15% of the raw materials were left with the main peak being the product. The reaction was shut down. The reaction solution was spun dry to directly obtain the crude product. The crude product was mixed with silica gel and purified by column chromatography to obtain 350 mg of Compound 2-13. The two-step yield was 57%.

The Preparation of Compound C-2a and C-2b

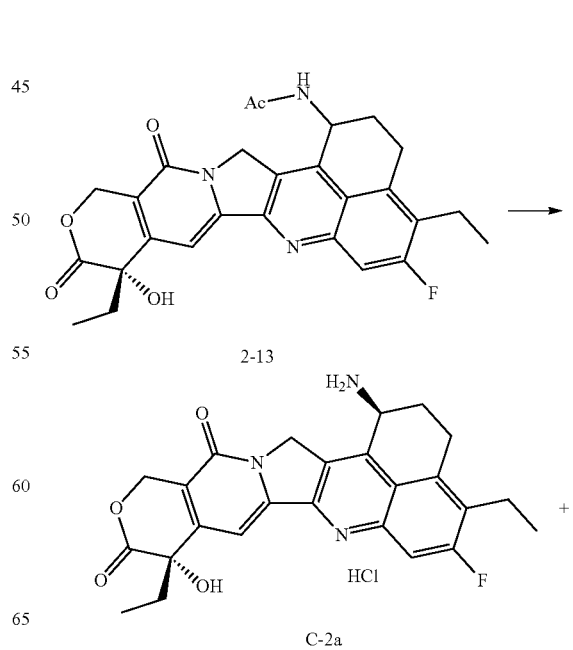

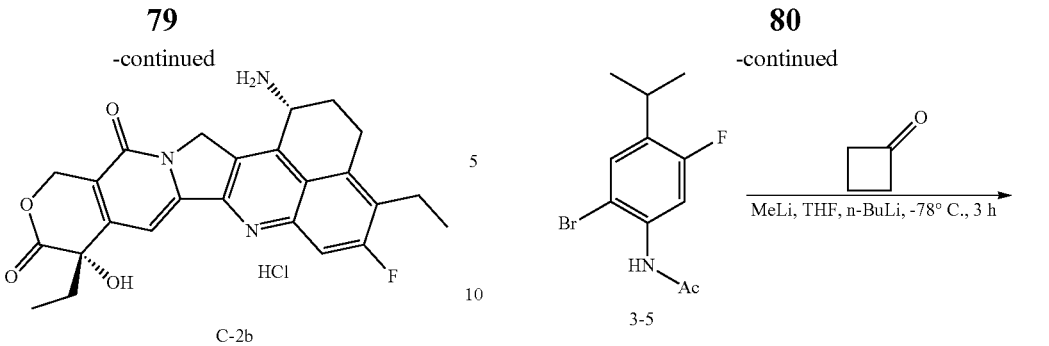

C-2b

Compound 2-13 (350 mg, 0.712 mmol) was added to 6M of HCl aqueous solution (7 mL), and stirred under reflux at 110° C. for 4 h. The reaction was detected by LCMS and the raw materials disappeared. The reaction was shut down. The reaction solution was directly lyophilized to obtain crude product. The crude product was directly purified by NP-HPLC to obtain 80 mg of Compound C-2a and 75 mg of Compound C-2b, both of which were light yellow solids. The two-step yield was 49%.

Compound C-2a: LCMS (m/z) [M+H]+=450.2. $^1$H NMR (400 MHz, DMSO): δ 8.52-8.38 (m, 3H), 7.89 (d, J=11.1 Hz, 1H), 7.36 (s, 1H), 6.56 (s, 1H), 5.74-5.69 (m, 2H), 5.55-5.30 (m, 3H), 5.10 (s, 1H), 3.48-3.43 (m, 1H), 3.24-3.10 (m, 1H), 2.94-2.88 (m, 2H), 2.56-2.53 (m, 1H), 2.28-2.13 (m, 1H), 1.99-1.81 (m, 2H), 1.22 (t, J=7.5 Hz, 3H), 0.89 (t, J=7.3 Hz, 3H).

Compound C-2b: LCMS (m/z) [M+H]+=450.2. $^1$H NMR (400 MHz, DMSO): δ 8.57-8.35 (m, 3H), 7.90 (d, J=11.1 Hz, 1H), 7.36 (s, 1H), 6.55 (s, 1H), 5.78-5.64 (m, 1H), 5.53-5.36 (m, 3H), 5.11 (s, 1H), 3.44-3.37 (m, 1H), 3.24-3.12 (m, 1H), 2.97-2.85 (m, 2H), 2.56-2.52 (m, 1H), 2.26-2.14 (m, 1H), 1.96-1.81 (m, 2H), 1.22 (t, J=7.5 Hz, 3H), 0.88 (t, J=7.3 Hz, 3H).

Example 3: Synthesis of Compounds C-3a and C-3b

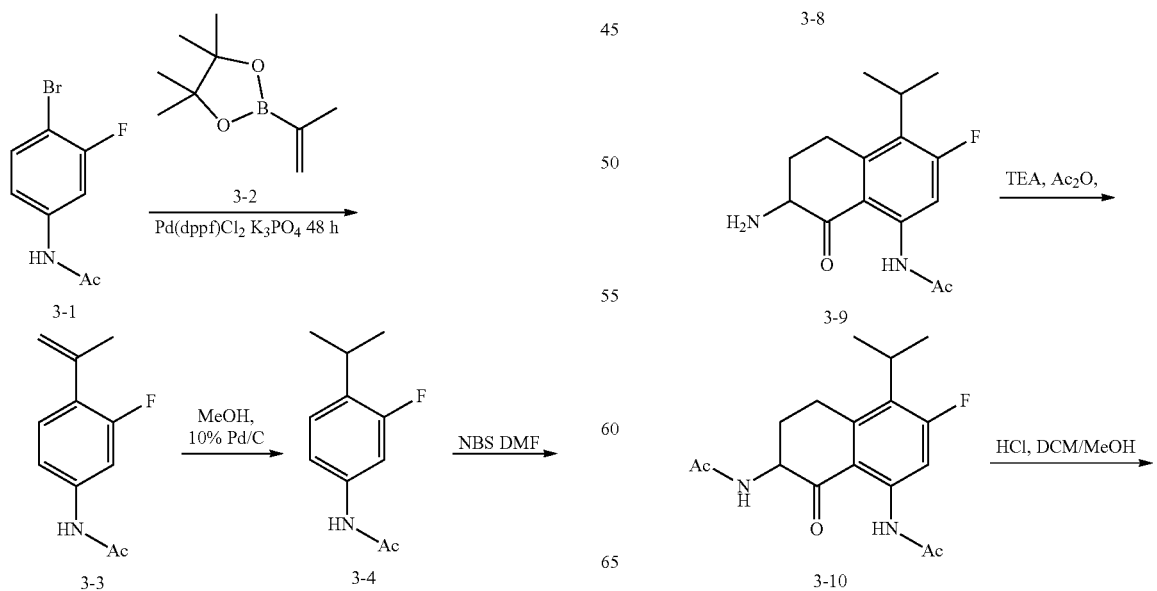

The Preparation of Compound 3-3

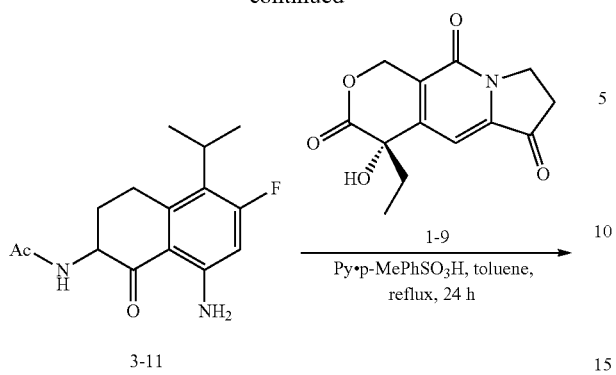

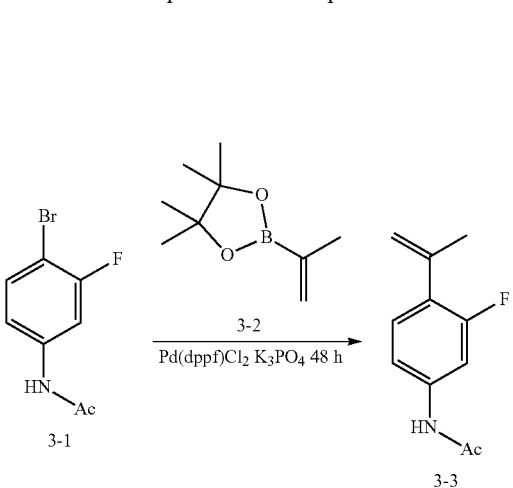

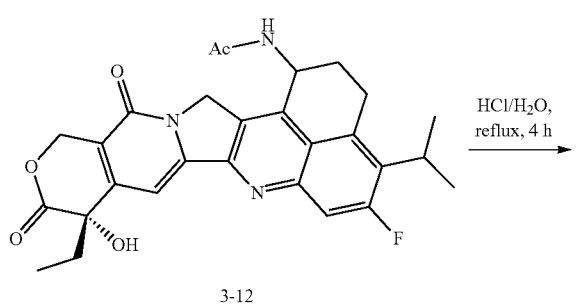

Compound 3-1 (33 g, 142 mmol) was dissolved in dioxane (300 mL) and H$_2$O (150 mL), and added with boronic acid ester 3-2 (28.7 g, 171 mmol), K$_3$PO$_4$ (90.6 g, 427 mmol), and Pd(dppf)Cl$_2$ (10.4 g, 14.2 mmol). The reaction solution was reacted at 115° C. for 48 h. The reaction was monitored by LCMS and the raw materials disappeared. After the completion of reaction, water (1 L) was added to the reaction solution, followed by extraction with EA (3×300 mL). The organic phases were combined, washed with water (3×500 mL) and saturated sodium chloride (1 L), dried over anhydrous sodium sulfate, filtered and concentrated to obtain crude product. The crude product was purified by column chromatography to obtain 24 g of Compound 3-3. The yield was 87%.

The Preparation of Compound 3-4

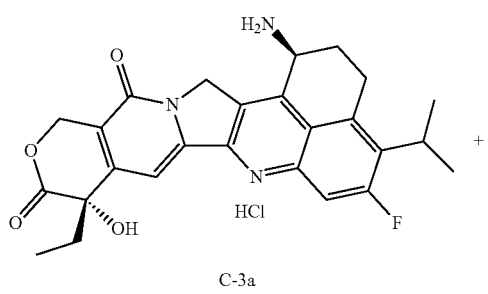

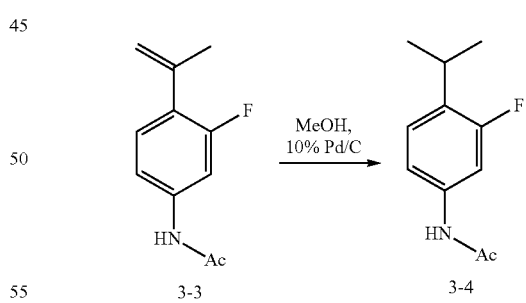

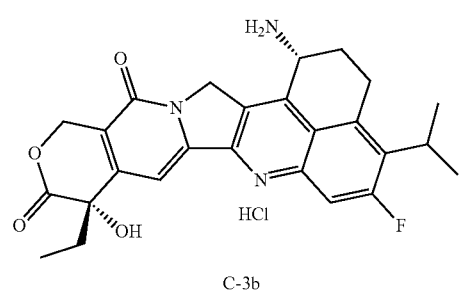 [SMILES: CCc1c(F)cc2nc3c(c4c2c1CC[C@H]4N)Cn1c-3cc2c(c1=O)COC(=O)[C@]2(O)CC ; Cl]

Compound 3-3 (24 g, 124 mmol) was dissolved by adding MeOH (300 mL), followed by the addition of 10% Pd/C (3.0 g) and reacted at room temperature (28° C.) for 18 h. The reaction was detected by LCMS and the raw materials disappeared. The reaction solution was filtered with diatomaceous earth and washed with methanol (1 L). The filtrate was spun dry to obtain 25 g of Compound 3-4. The yield was not counted.

The Preparation of Compound 3-5

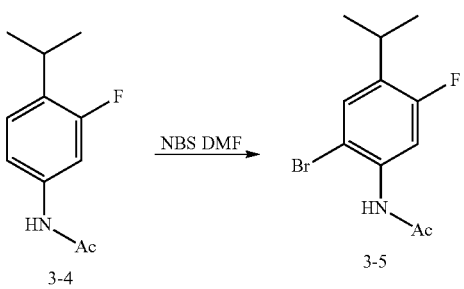

Compound 3-4 (25 g, 128 mmol) was dissolved in DMF (300 mL), followed by the addition of NBS (46 g, 256 mmol), and stirred at 25° C. for 18 h. TLC (PE/EA=1/1) showed the completion of reaction. The reaction solution was added with 500 mL of water, followed by extraction with EA (3×200 mL). The organic phases were combined, washed with water (3×300 mL), washed with saturated sodium chloride (500 mL), dried over anhydrous sodium sulfate, filtered, and concentrated to obtain crude product. The crude product was mixed with silica gel and purified by column chromatography to obtain 28 g of Compound 3-5. The two-step yield was 80%.

The Preparation of Compound 3-6

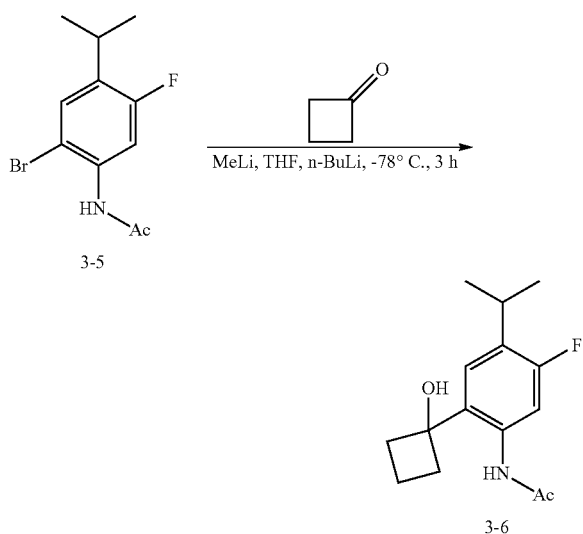

Compound 3-5 (10 g, 36.5 mmol) was placed in a dry three-necked flask under $N_2$ protection, dissolved by adding 100 mL of THF, cooled to about −90° C., slowly added dropwise 1.6 M of MeLi solution (46 mmol, 73.0 mmol) while keeping the temperature remain below −80° C., and stirred at the same temperature for 30 min, followed by the slow dropwise addition of 2.5 M of n-BuLi/THF solution (29.1 mmol, 73.0 mmol) and stirred at −90° C. for 30 min. After that, a solution of cyclobutanone (3.07 g, 143 mmol) in THF (50 mL) was slowly added dropwise and stirred at that temperature for 1 h. The reaction was detected by LCMS and 15% of the raw materials were left with the main peak being the product. The reaction was quenched by adding 200 mL of saturated aqueous ammonium chloride to the reaction solution, followed by the addition of 200 mL of water, and extracted with EA (3×100 mL). The organic phases were combined, washed with saturated sodium chloride (100 mL), dried over anhydrous sodium sulfate, filtered and concentrated to obtain crude product. The crude product was mixed with silica gel and purified by column chromatography to obtain 7.9 g of Compound 3-6. The yield was not counted.

The Preparation of Compound 3-7

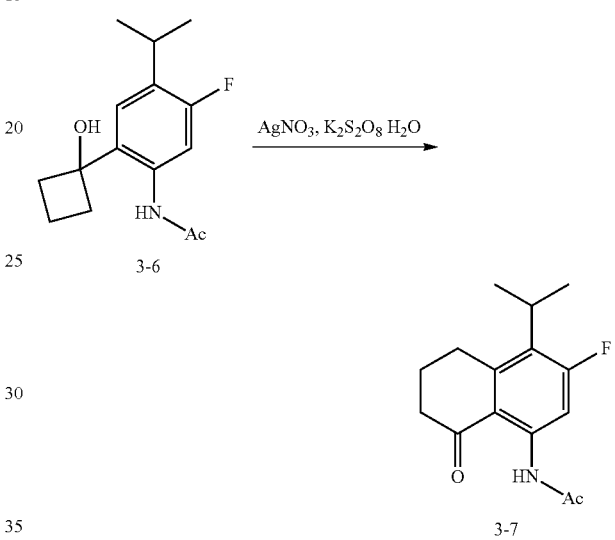

Compound 3-6 (7.9 g, 29.8 mmol) was added to DCM (160 mL) and $H_2O$ (160 mL), followed by the addition of $AgNO_3$ (1.01 g, 5.96 mmol) and $K_2S_2O_8$ (24.2 g, 89.3 mmol), and stirred at 28° C. for 18 h. The reaction was detected by LCMS and the raw materials disappeared with the main peak being the product. The reaction was shut down. 1 L of water was added to the reaction solution, followed by extraction with DCM (3×100 mL). The organic phases were combined, washed with saturated sodium chloride (500 mL), dried over anhydrous sodium sulfate, filtered, and concentrated to obtain crude product. The crude product was mixed with silica gel and purified by column chromatography to obtain 1.45 g of Compound 3-7. The two-step yield was 16%.

The Preparation of Compound 3-8

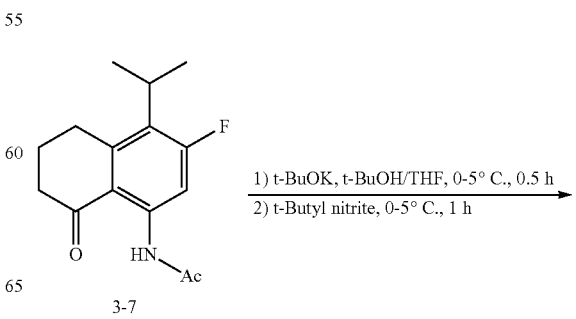

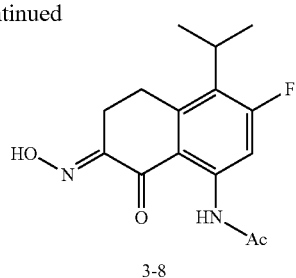

Potassium tert-butoxide (2.16 g, 19.3 mmol) was added to tert-butanol (8 mL) and THF (8 mL) under $N_2$ protection, followed by the slow dropwise addition of a solution of Compound 3-7 (1.45 g, 5.51 mmol) in THF (13 mL) at about 0° C., and stirred at 0° C. for 30 min, followed by the slow addition of n-butyl nitrite (1.14 g, 11.1 mmol) and stirred at 0° C. for 1 h. TLC (PE/EA=1/1) showed that the reaction was completed. 50 mL of water was added to the reaction solution, followed by the addition of 1 M of HCl to adjust the pH to 2-3, and extracted with EA (3×20 mL). The organic phases were combined, washed with saturated sodium chloride (500 mL), dried over anhydrous sodium sulfate, filtered, and concentrated to obtain crude product. 20 mL of PE:MTBE=10:1 was added to the crude product, stirred at 25° C. for 1 h and filtered. The filter cake was collected and dried with oil pump to obtain 1.55 g of Compound 3-8. The yield was not counted.

The Preparation of Compound 3-10

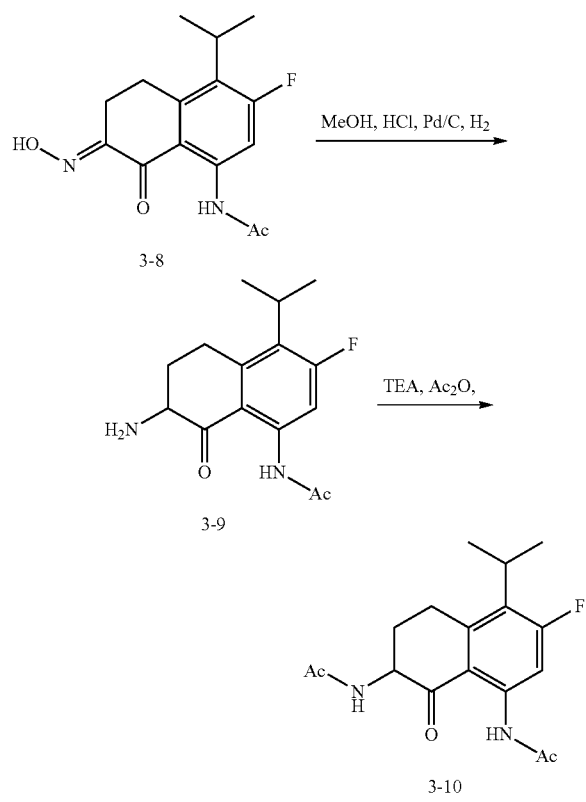

Compound 3-8 (1.55 g, 5.30 mmol) was dissolved in MeOH (47 mL), added with 4 M of HCl/MeOH (2.65 mL, 52.4 mmol), followed by the addition of 10% Pd/C (300 mg) and stirred at 28° C. for 3 h. The reaction was detected by LCMS and the raw materials disappeared. TEA (1.89 g, 18.6 mmol) and $Ac_2O$ (1.25 g, 12.2 mmol) were added to the reaction solution and stirred at 28° C. for 1 h. The reaction was detected by LCMS and the raw material disappeared. The reaction solution was filtered with diatomaceous earth and washed with methanol (300 mL). The filtrate was spun dry to obtain crude product. The crude product was purified by column chromatography to obtain 500 mg of Compound 3-10. The three-step yield was 37%.

The Preparation of Compound 3-11

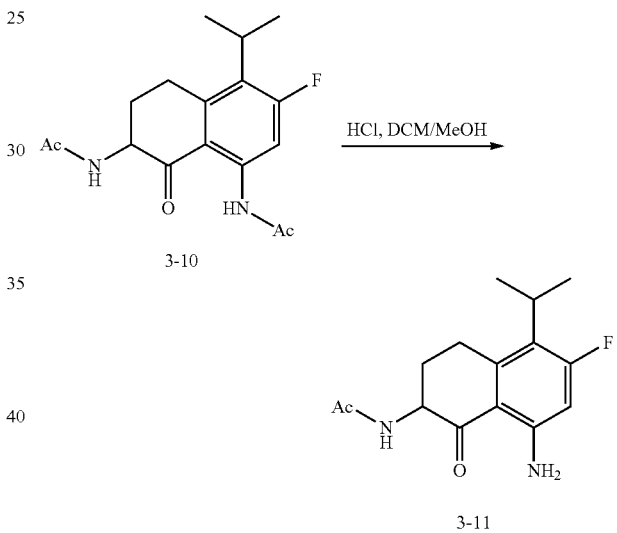

Compound 3-10 (500 mg, 1.56 mmol) was added to DCM (10 mL) and MeOH (5 mL), followed by the addition of concentrated hydrochloric acid (3 mL), and stirred at 28° C. for 18 h. The reaction was detected by LCMS, and the raw materials disappeared with the main peak being the product. The reaction was shut down. 30 mL of water was added to the reaction solution, followed by the addition of saturated aqueous sodium bicarbonate to adjust the pH to 9-10, and extracted with DCM (3×10 mL). The organic phases were combined, washed with saturated sodium chloride (30 mL), dried over anhydrous sodium sulfate, filtered and concentrated to obtain crude product. The filter cake was added with 15 mL of PE:MTBE=10:1, stirred at 25° C. for 1 h, and filtered. The filter cake was collected to obtain 320 mg of Compound 3-11. The yield was not counted.

The Preparation of Compound 3-12

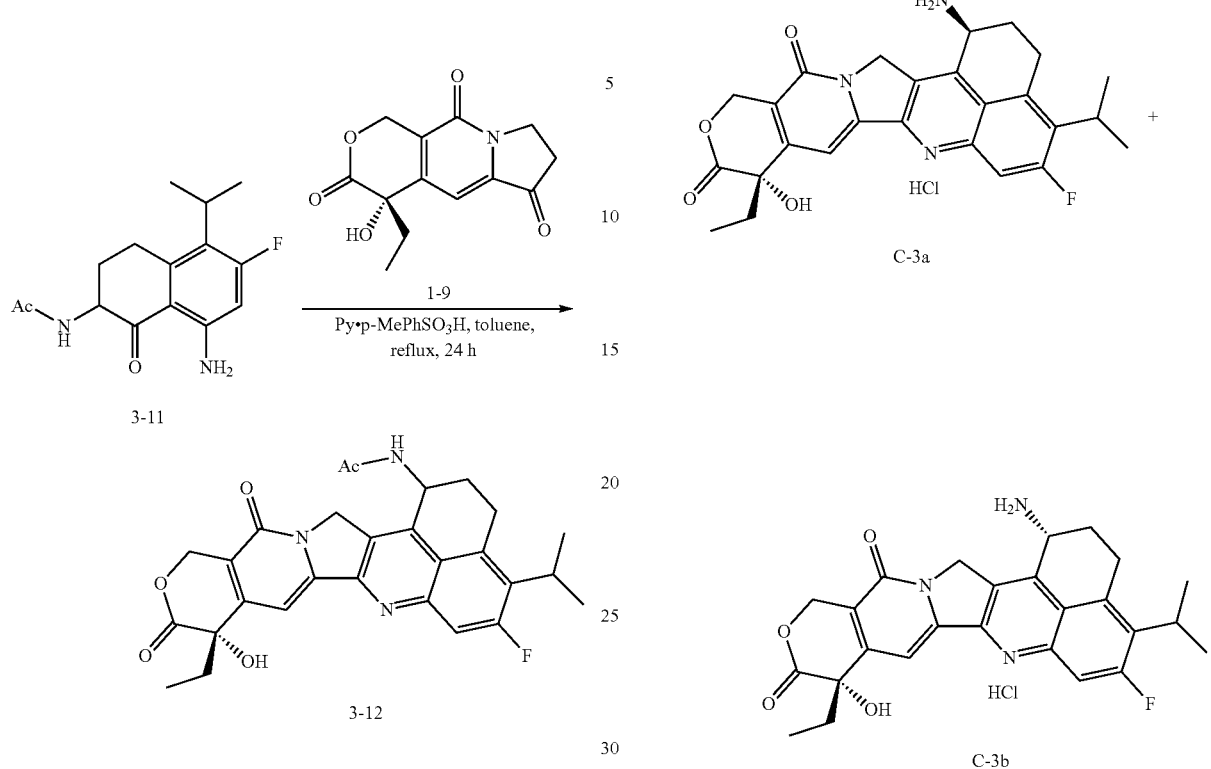

Compound 3-11 (320 mg, 1.15 mmol) was dissolved in toluene (8 mL), added with HM-582_8 (275 mg, 1.05 mmol) and PPTS (132 mg, 0.52 mmol), and stirred at 125° C. for 24 h. The reaction was detected by LCMS and 15% of the raw materials were left with the main peak being the product. The reaction was shut down. The reaction solution was spun dry directly to obtain crude product. The crude product was mixed with silica gel and purified by column chromatography to obtain 400 mg of Compound 3-12. The wo-step yield was 69%.

1.2.10 the Preparation of Compounds C-3a and C-3b

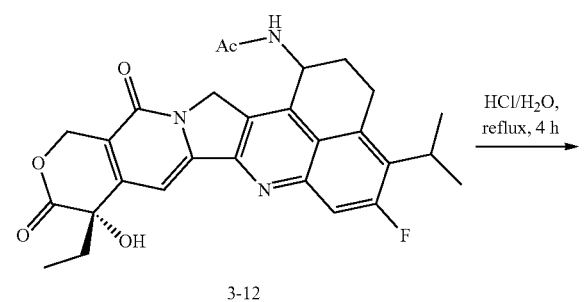

Compound 3-12 (400 mg) was added to 6 M of HCl aqueous solution (5 mL), and stirred under reflux at 110° C. for 4 h. The reaction was detected by LCMS and the raw materials disappeared. The reaction was shut down. The reaction solution was directly lyophilized to obtain crude product. The crude product was directly purified by NP-HPLC to obtain 55 mg of Compound C-3a and 90 mg of Compound C-3b. The yield was 40%

Compound C-3a: LCMS (m/z) [M+H]+=464.2. $^1$H NMR (400 MHz, DMSO) δ 8.51 (brs, 3H), 7.89 (d, J=10.2 Hz, 1H), 7.37 (s, 1H), 6.57 (s, 1H), 5.74-5.69 (m, 1H), 5.56-5.36 (m, 3H), 5.11 (s, 1H), 3.66-3.54 (m, 1H), 3.49-3.40 (m, 1H), 3.26-3.13 (m, 1H), 2.59-2.54 (m, 1H), 2.26-2.15 (m, 1H), 1.97-1.82 (m, 2H), 1.45-1.35 (m, 6H), 0.91 (t, J=7.6 Hz, 3H).

Compound C-3b: LCMS (m/z) [M+H]+=464.2. $^1$H NMR (400 MHz, DMSO) δ 8.50 (brs, 3H), 7.89 (d, J=10.2 Hz, 1H), 7.37 (s, 1H), 6.57 (s, 1H), 5.79-5.64 (m, 1H), 5.55-5.38 (m, 3H), 5.12 (s, 1H), 3.63-3.57 (m, 1H), 3.48-3.41 (m, 1H), 3.26-3.13 (m, 1H), 2.58-2.54 (m, 1H), 2.27-2.13 (m, 1H), 1.97-1.83 (m, 2H), 1.46-1.34 (m, 6H), 0.90 (t, J=7.6 Hz, 2H).

Example 4: Synthesis of Compound C-4a

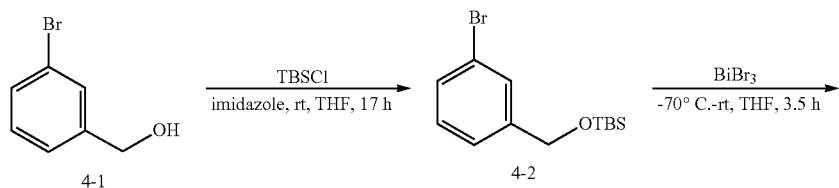

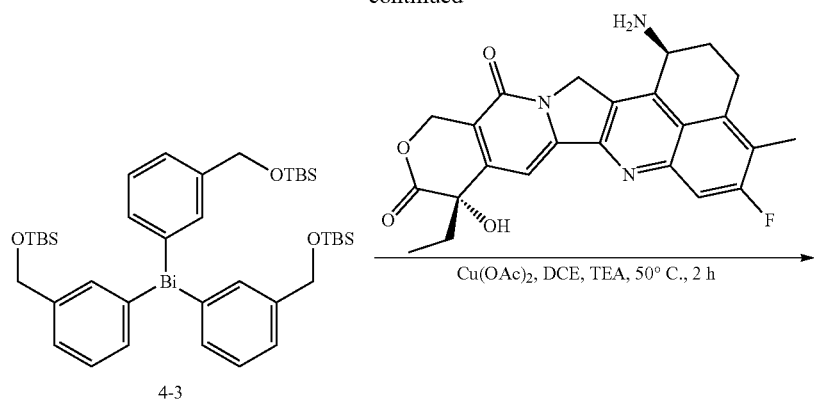
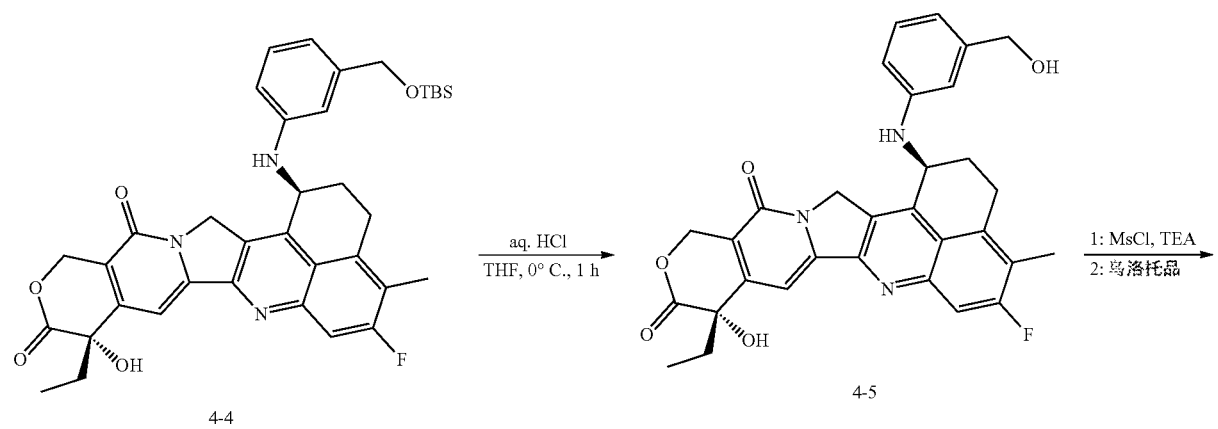
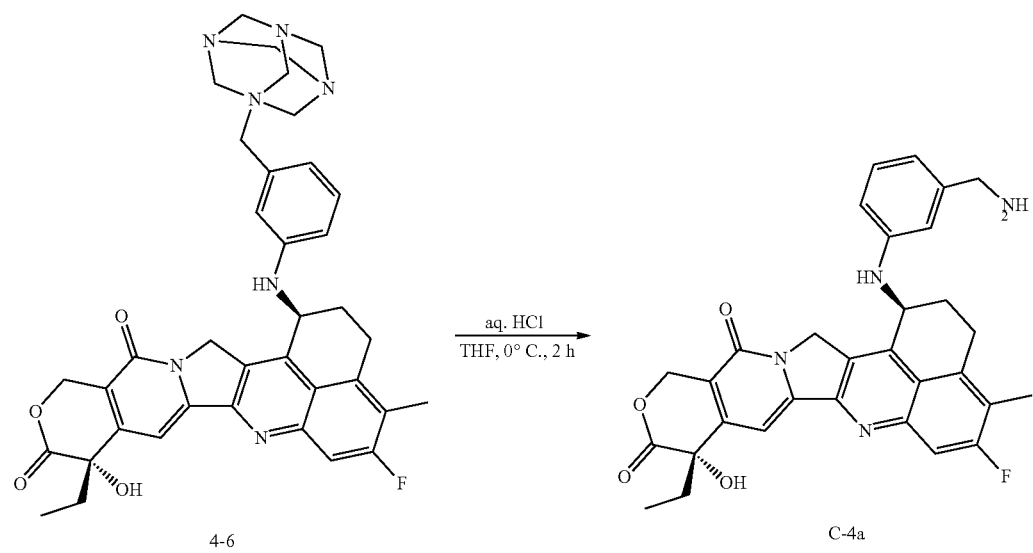

The Preparation of Compound 4-2

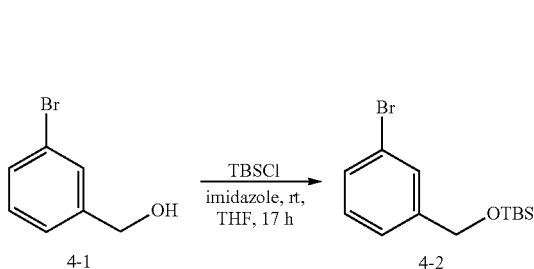 [SMILES: OCc1cccc(Br)c1 ; "TBSCl" ; CC(C)(C)[Si](C)(C)OCc1cccc(Br)c1]

Compound 4-1 (10 g, 53.5 mmol) and imidazole (10.9 g, 160 mmol) were dissolved in THF (100 ml), added with TBSCl (12.1 g, 80.1 mmol) dissolved in 30 mL of super dry THF using a pressure-balanced dropping funnel. The system was replaced with $N_2$ and the reaction solution was stirred at room temperature for 17 h. TLC (PE:EA=10) showed that the reaction was completed. The reaction solution was added to water (100 mL), extracted with ethyl acetate (150 mL), washed with water (50 mL) for 3 times. The organic phase was dried over anhydrous sodium sulfate, concentrated, and further purified by column chromatography to obtain 15 g of Compound 4-2. The yield was 94%.

The Preparation of Compound 4-3

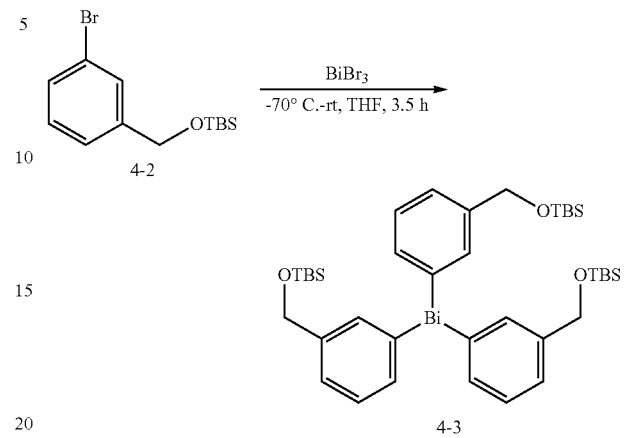

To a solution of Compound 4-2 (15.0 g, 49.7 mmol) in THF (150 ml), n-butyllithium (24.45 ml, 61 mmol, 2.5 M) was added at −70° C., and stirred at −70° C. for 1 h, followed by the addition of bismuth bromide (8.19 g, 19.9 mmol) dissolved in super-dry THF (20 ml) and stirred at −70° C. for 0.5 h, gradually warmed to room temperature and stirred for 2 h. TLC (PE:EA=10:1) showed that the reaction was completed. The reaction solution was poured into water (100 mL), extracted with DCM (100 mL), washed with water (50 mL), dried over anhydrous sodium sulfate, spun dry, and further purified by column chromatography to obtain 5 g of Compound 4-3. The yield was 12%.

The Preparation of Compound 4-4

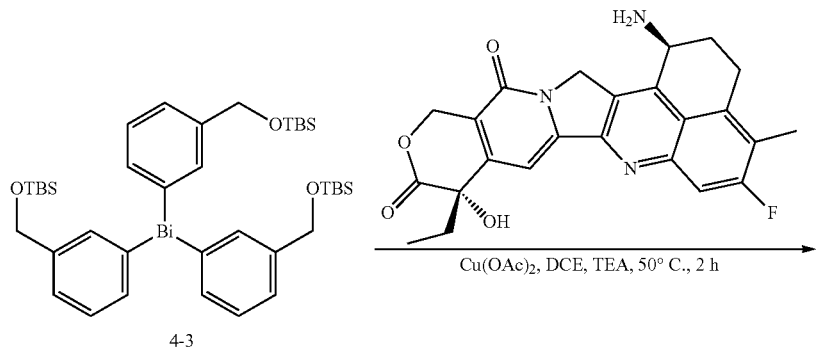

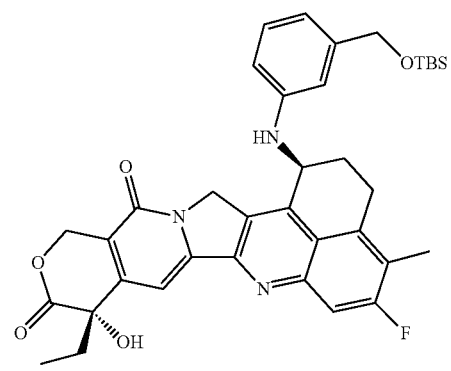

Compound 4-3 (4.0 g, 4.5 mmol), exatecan (400 mg, 0.919 mmol, prepared according to Example 5), and anhydrous copper acetate (33.8 mg, 1.83 mmol) in 1,2-dichloroethane (40 mL) were added with TEA (279 mg, 2.7 mmol), and reacted at 50° C. for 2 h. LCMS showed that the reaction was completed. The reaction solution was added with water (50 mL), extracted with DCM (100 mL), dried over anhydrous sodium sulfate, spun dry, and purified by a column to obtain 110 mg of Compound 4-4. The yield was 17%.

The Preparation of Compound 4-5

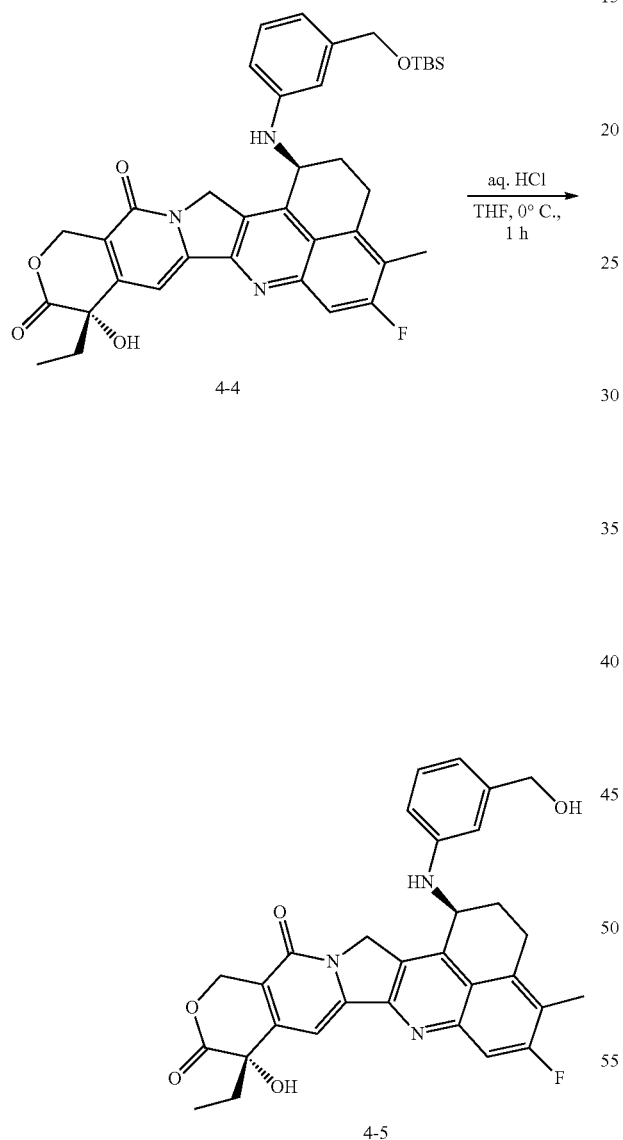

Compound 4-4 (100 mg, 0.153 mmol) was added to a 50 mL reaction flask, followed by the addition of THF (1 mL) and HCl aqueous solution (2 M, 1 mL), and reacted at 0° C. for 1 h. LCMS showed the complete reaction of the raw materials. The reaction solution was added with 1 mL of acetonitrile, and directly lyophilized to obtain 90 mg of Compound 4-5. The yield was not counted.

The Preparation of Compound 4-6

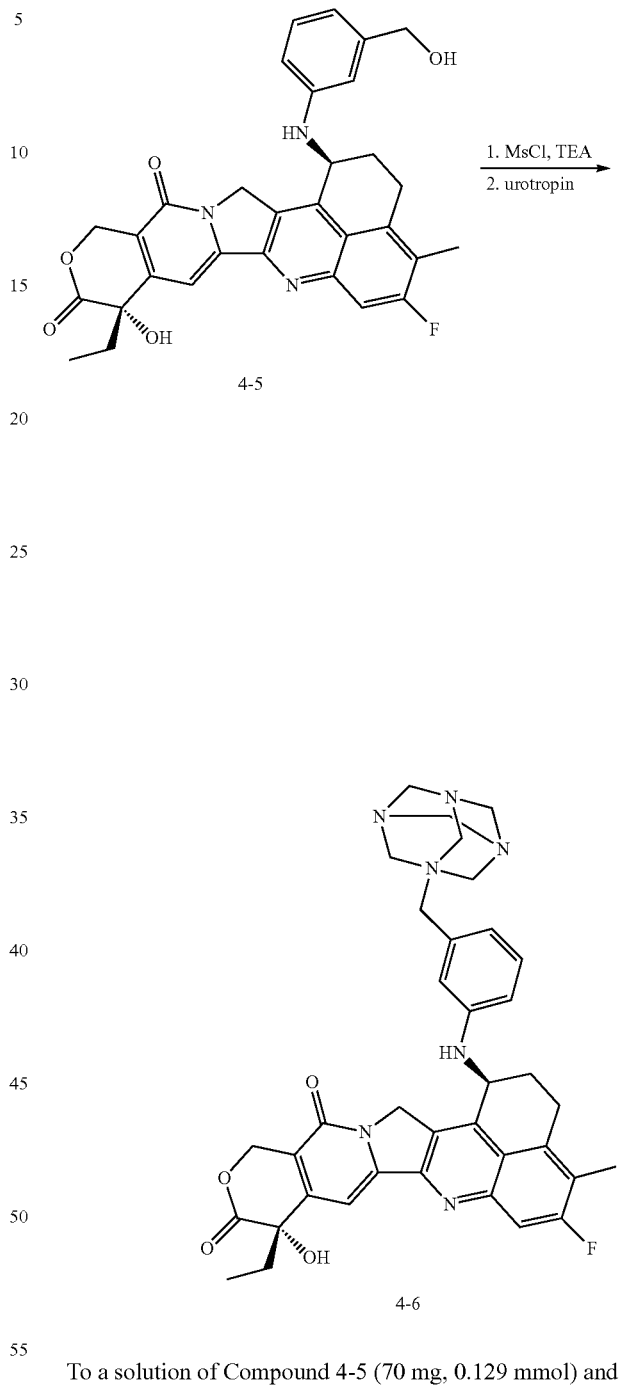

To a solution of Compound 4-5 (70 mg, 0.129 mmol) and TEA (39 mg, 0.387 mmol) in DCM (1 ml), MsCl (29 mg, 0.26 mmol) was added at 0° C. and reacted for 1 h. After the completion of reaction was monitored by LCMS, urotropine (90 mg, 0.65 mmol) was added to the reaction flask and reacted at room temperature for 2 h. LCMS showed that the reaction was completed. The reaction solution was added to water and extracted with DCM. Then the organic phase and aqueous phase were sent for analysis, with the product being in aqueous phase. 55 mg of Compound 4-6 were obtained by lyophilization of the aqueous phase. The yield was not counted.

The Preparation of Compound C-4a

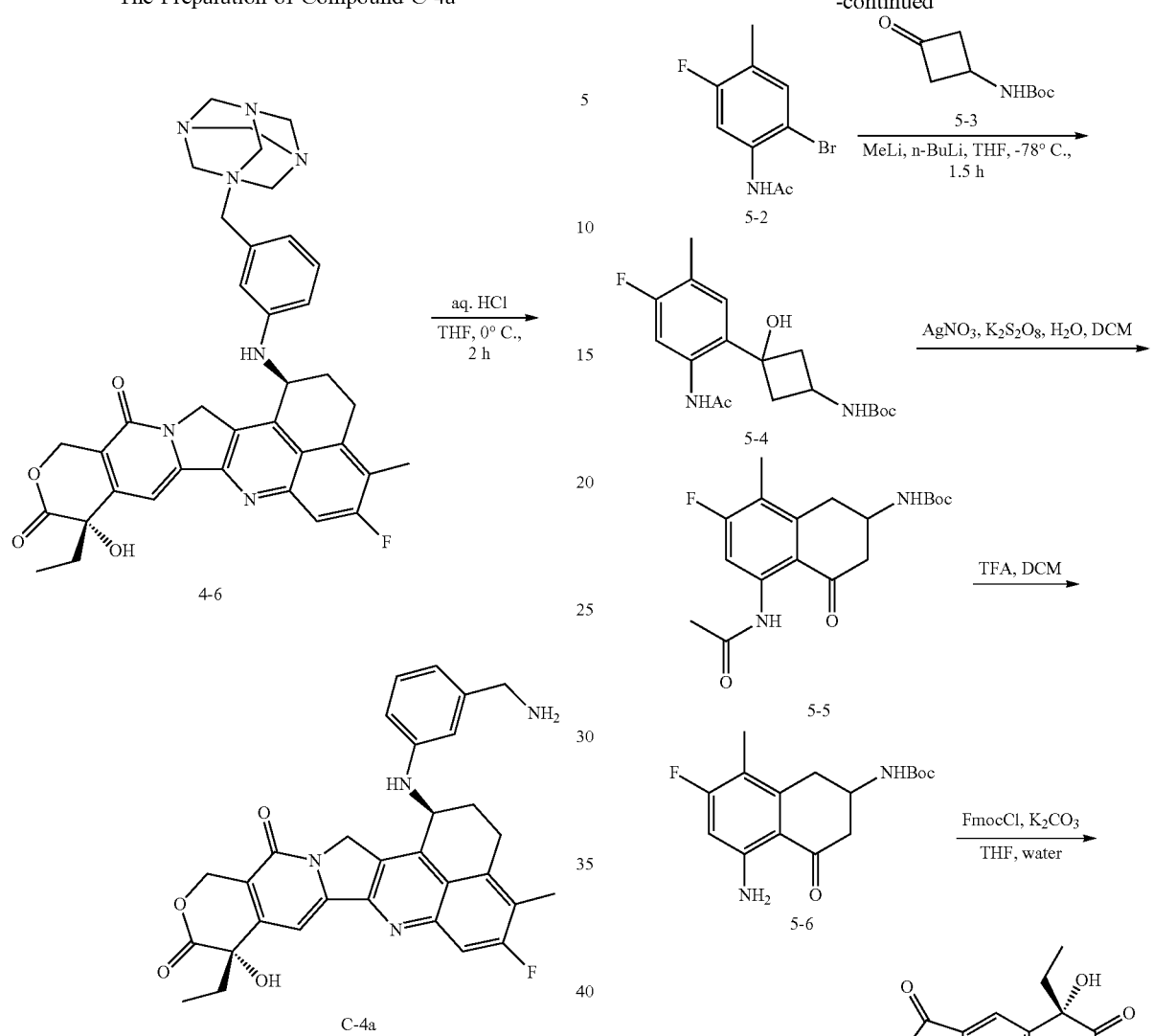

Compound 4-6 (50 mg, mmol) was added to the reaction flask, followed by the addition of 1 mL of THF and 1 mL of aqueous hydrochloric acid (6 M), and reacted at 0° C. for 2 h. LCMS showed that the reaction was completed. The reaction solution was sent directly to the preparation to obtain 1.3 mg of product. The yield was not counted. LCMS (m/z) [M+H]*=541.3

Example 5: Synthesis of Compounds C-5a and C-5b

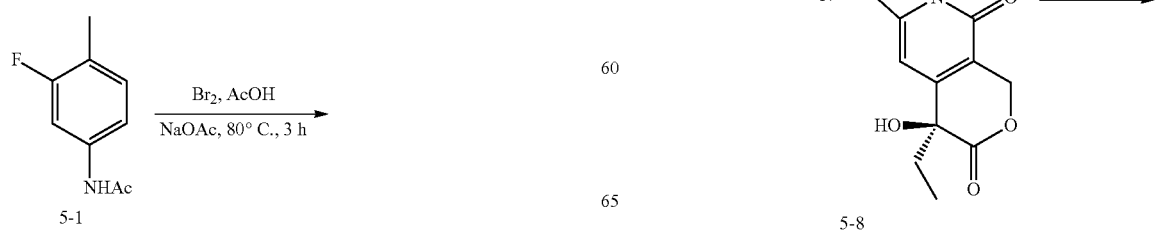

-continued

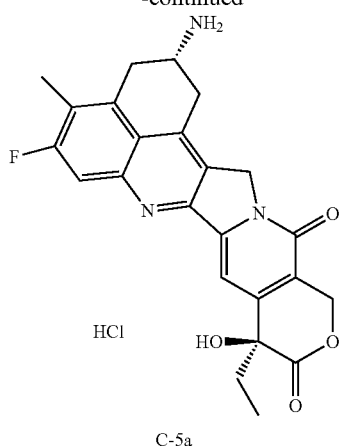

C-5a

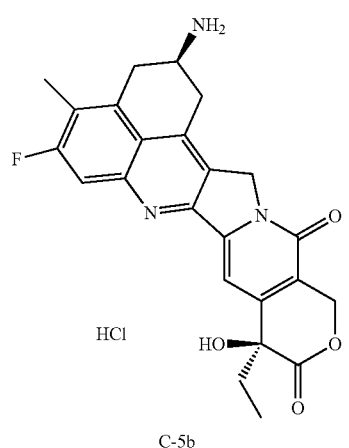

C-5b

The Preparation of Compound 5-2

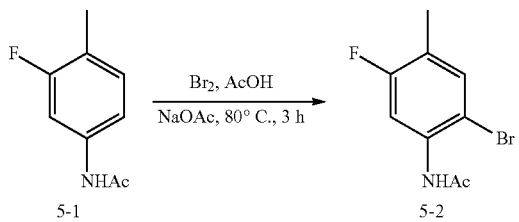

In N₂ environment, a solution of Compound 5-1 (48.0 g, 287 mmol) and NaOAc (28.3 g, 345 mmol) in AcOH (165 mL) was warmed to 60° C., and added dropwise with Br₂ (in AcOH, 55.0 g, 345 mmol). Then the reaction solution was warmed to 80° C. and stirred for 3 h. After LCMS monitored the completion of reaction, the reaction solution was cooled to room temperature, and then poured into ice water (2.5 L) and stirred for 30 min. Yellow solids were filtered out, dried at 50° C., and further purified by silica gel column chromatography to obtain 62 g of Compound 5-2. The yield was 90%. LCMS (m/z)=246.0.

The Preparation of Compound 5-4

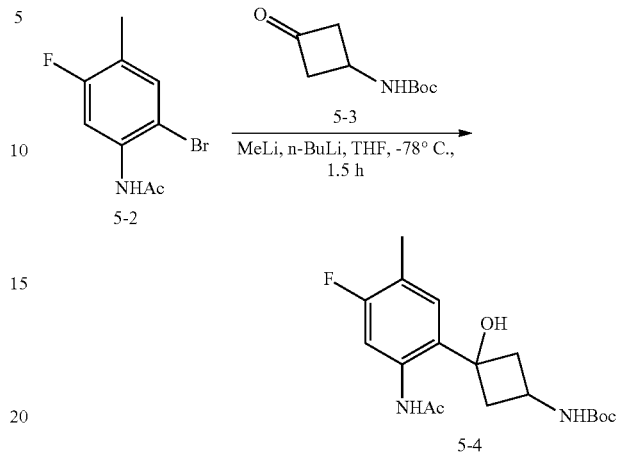

In N₂ environment, a solution of Compound 5-2 (5.0 g, 20.3 mmol) in THF (50 mL) was cooled to −78° C., added dropwise with MeLi (8.13 mL, 24.4 mmol) and stirred for 1 h, followed by the addition of n-BuLi (9.76 mL, 24.4 mmol) and stirred for 1.5 h. After that, a solution of Compound 5-3 (4.52 g, 24.4 mmol) in THF (10 mL) was added dropwise into the reaction solution and stirred at −78° C. for 1.5 h. After LCMS monitored the completion of reaction, the reaction solution was added with saturated aqueous NH₄Cl (200 mL) and extracted with EA (150 mL*3). The organic layer was washed with saturated NaCl (200 mL*3), dried and concentrated to obtain a yellow crude product, which was further purified by column chromatography to obtain 2.0 g of Compound 5-4. The yield was 28%.

The Preparation of Compound 5-5

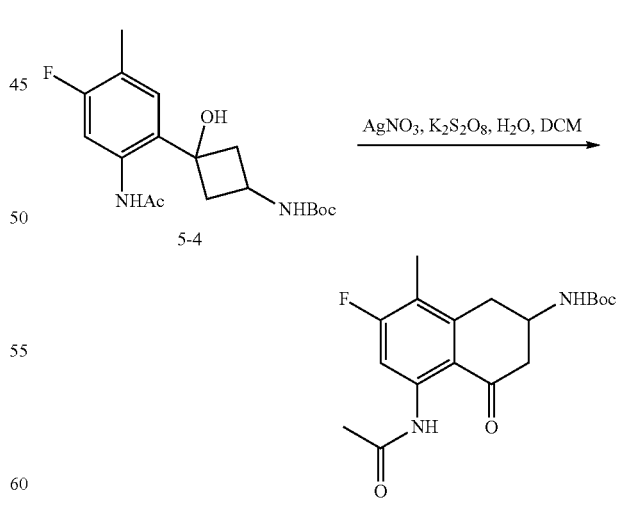

In N₂ environment, to a solution of Compound 5-4 (3.67 g, 10.4 mmol) in DCM (70 mL)/water (70 mL), AgNO₃ (169 mg, 1.0 mmol) and K₂S₂O₈ (8.42 g, 31.2 mmol) were added at 0° C. The reaction solution was stirred overnight, from 0°

C. to room temperature. After the completion of reaction was monitored by TLC, the reaction solution was separated and extracted with DCM (50 mL*3). The organic layer was washed with saturated Na₂SO₃ (100 mL*3), dried and concentrated to obtain a crude product, which was further purified by column chromatography to obtain 1.77 g of Compound 5-5. The yield was 47%.

The Preparation of Compound 5-6

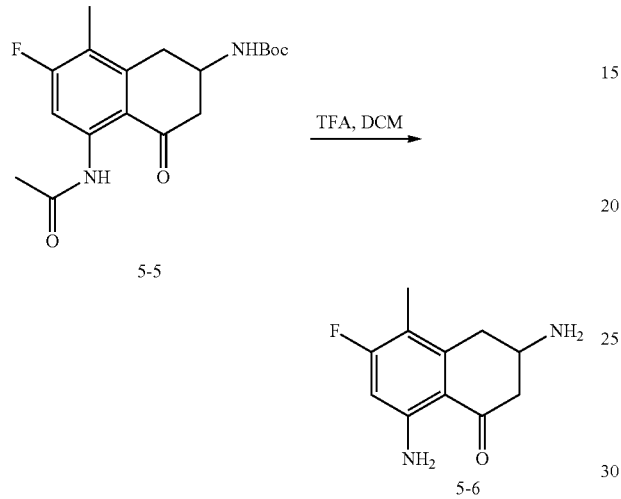

In $N_2$ environment, to a solution of Compound 5-5 (1.77 g, 5.1 mmol) in a mixture of DCM (40 mL) and MeOH (20 mL), concentrated HCl (5.0 mL) was added dropwise at 0° C. The reaction solution was stirred overnight at room temperature. After completion of reaction was monitored by TLC, the reaction solution was concentrated to obtain 1.05 g of Compound 5-6, which was directly used in the next step of reaction.

The Preparation of Compound 5-7

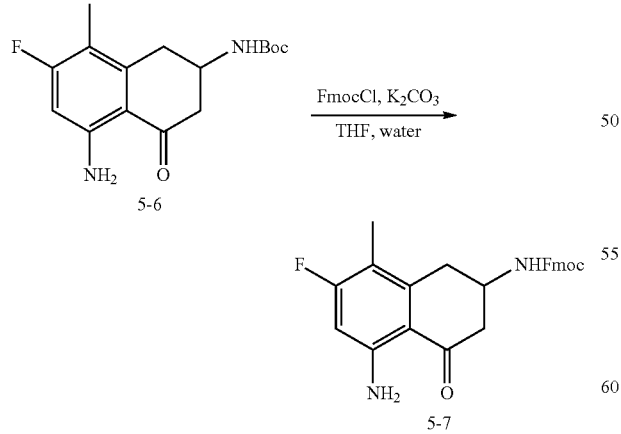

In $N_2$ environment, to a solution of FmocCl (1.16 g, 4.5 mmol) in THF (2 mL), a solution of Compound 5-6 (1.05 g, 4.3 mmol) and K₂CO₃ (1.3 g, 9.4 mmol) in THF (18 mL)/water (27 mL) was added dropwise at 0° C. The reaction solution was stirred at the same temperature for 3 h. After completion of reaction was monitored by TLC, the reaction solution was separated by adding with 2-Me-THF (100 mL). The organic layer was washed with water (70 mL*3), dried and concentrated, and further purified by column chromatography to obtain 927 mg of Compound 5-7. The yield was 48%.

The Preparation of Compound 5-8

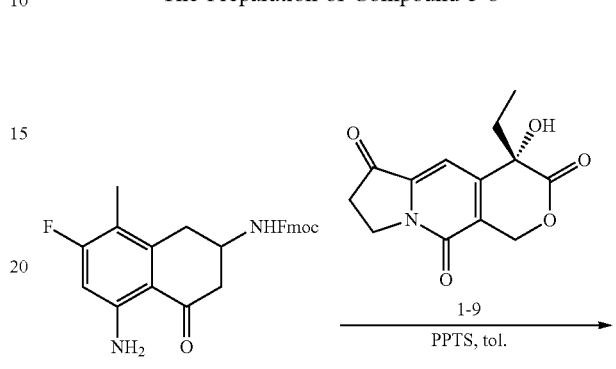

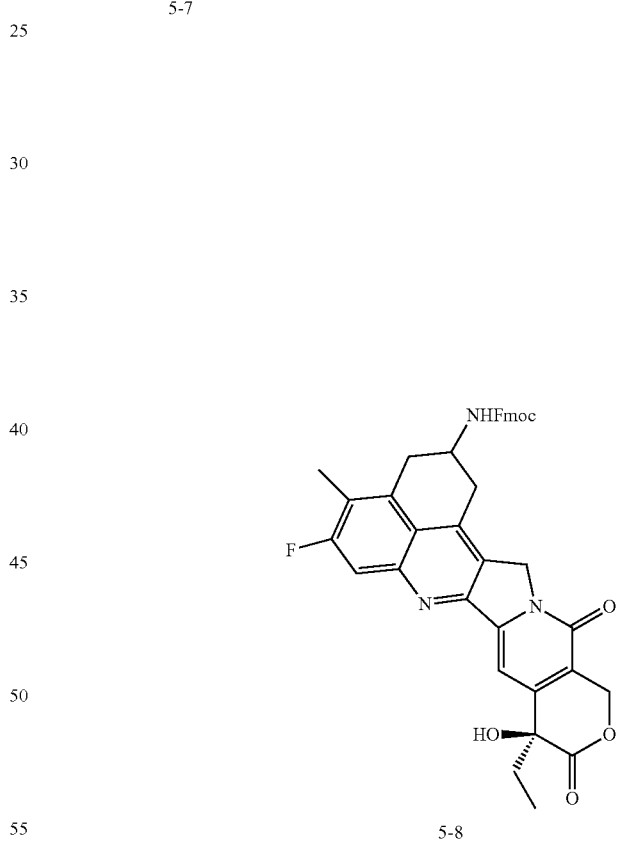

In $N_2$ environment, a solution of Compound 5-7 (368 mg, 0.86 mmol), Compound 1-9 (202 mg, 0.86 mmol) and PPTS (43 mg, 0.17 mmol) in toluene (9.0 mL) was heated to 125° C. (external temperature) and stirred under reflux overnight. After the reaction is completed, the reaction solution was cooled to room temperature and concentrated to dryness to obtain reddish-brown solids, which were further separated by preparative high-performance liquid chromatography and lyophilized to obtain 52 mg of Compound 5-8. The yield was 14%.

The Preparation of Compound C-5 (Compounds C-5a and C-5b

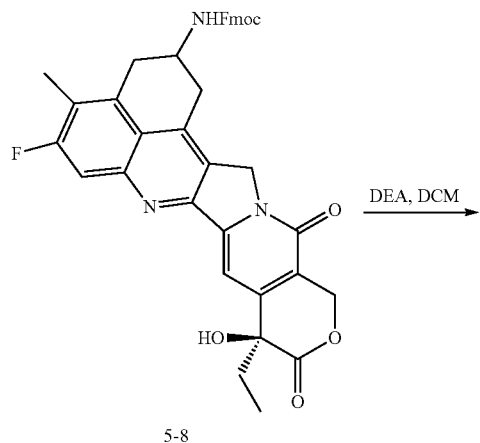

Diethylamine (1.0 mL) was added to a solution of Compound 5-8 (52 mg, 0.08 mmol) in DCM (2.0 mL) at 0° C. After completion of reaction was monitored by TLC, the reaction solution was directly concentrated to dryness, and further separated by preparative liquid chromatography to obtain 4 mg of Compound C-5 as a mixture of Compound C-5a and Compound C-5b. The yield was not counted. LCMS (m/z)=436.1. $^1$H NMR (400 MHz, DMSO): δ 7.86 (d, J=10.8 Hz, 1H), 7.35 (s, 1H), 6.56 (s, 1H), 5.46 (s, 2H), 5.30 (s, 2H), 3.89-3.85 (m, 1H), 3.52-3.50 (m, 2H), 3.27-3.20 (m, 1H), 3.12-3.09 (m, 1H), 2.46 (s, 1H), 2.41 (s, 2H), 1.96-1.81 (m, 2H), 0.90 (t, J=7.4 Hz, 3H).

Example 6: Synthesis of Compound C-6a and C-6b

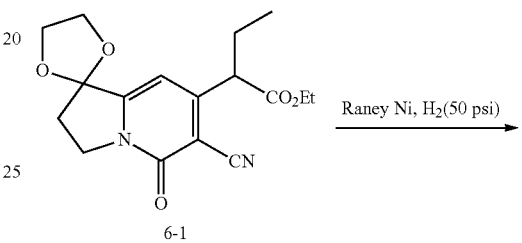

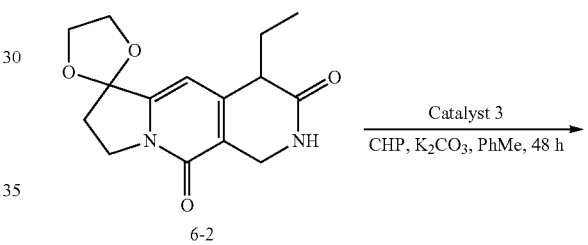

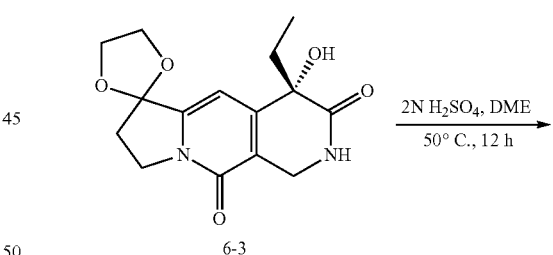

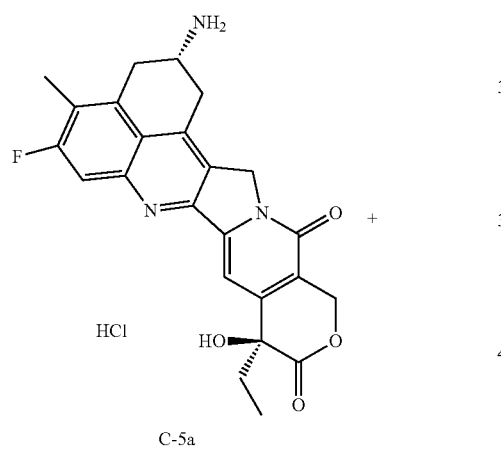

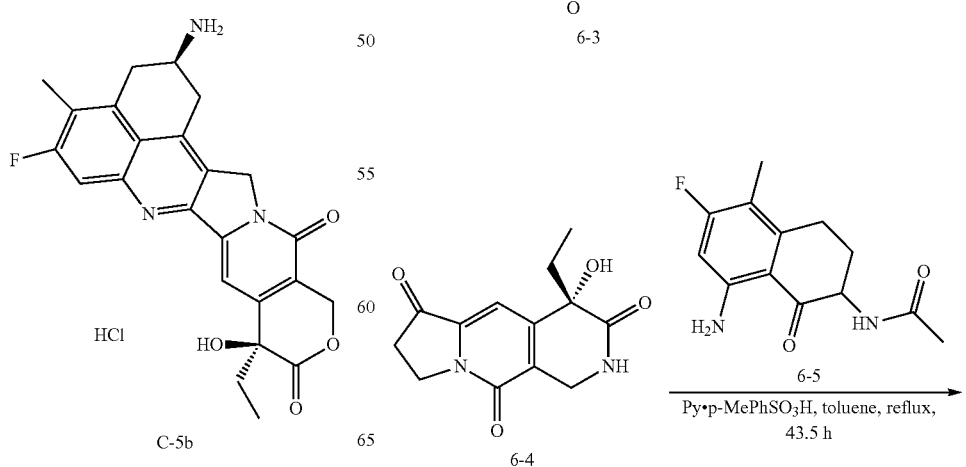

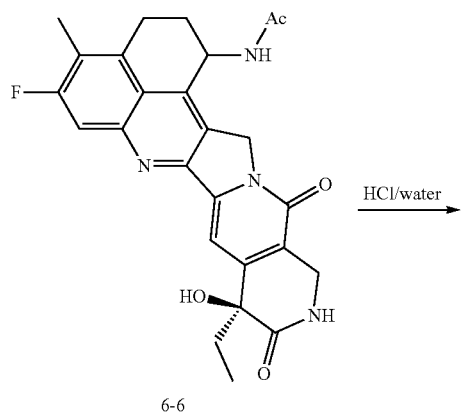

6-6

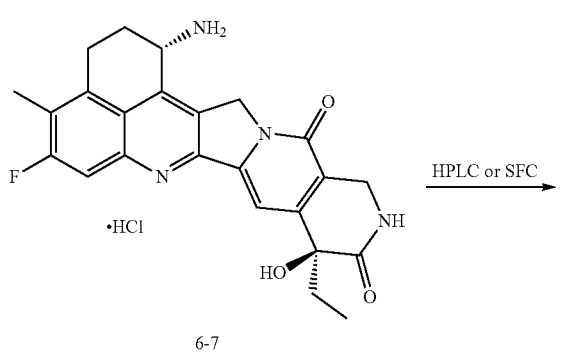

6-7

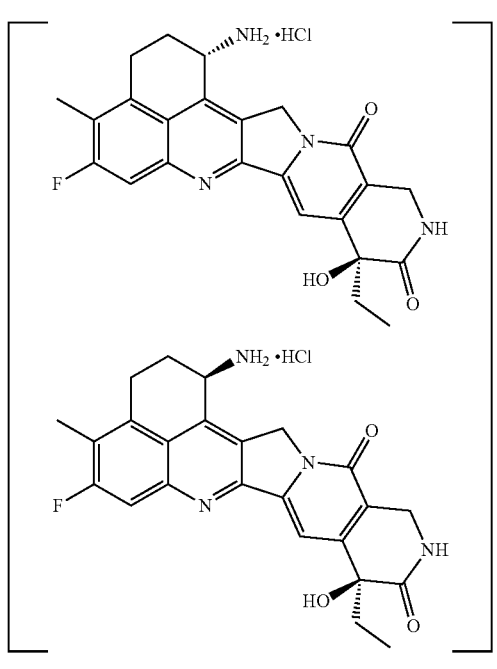

C-6a

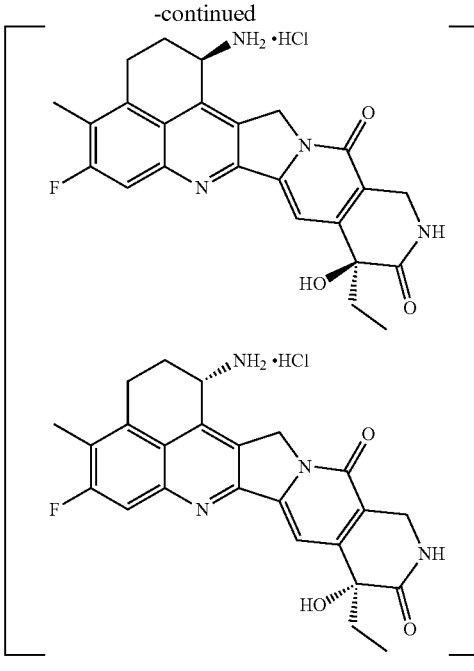

C-6b

The Preparation of Compound 6-2

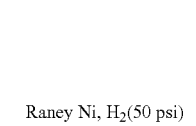

6-1

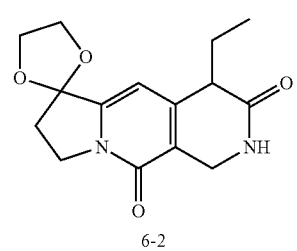

6-2

In $N_2$ environment, to a solution of Compound 6-1 (9.0 g, 27.1 mmol) in MeOH (450 mL), Ra-Ni (4.0 g) was added. The system with replaced with $H_2$ for three times, warmed to 50° C. and stirred for 16 h. After LCMS monitored the completion of reaction, the reaction solution was cooled to room temperature, filtered, concentrated, and further purified by column chromatography to obtain 6.7 g of Compound 6-2. The yield was 85%.

The Preparation of Compound 6-3

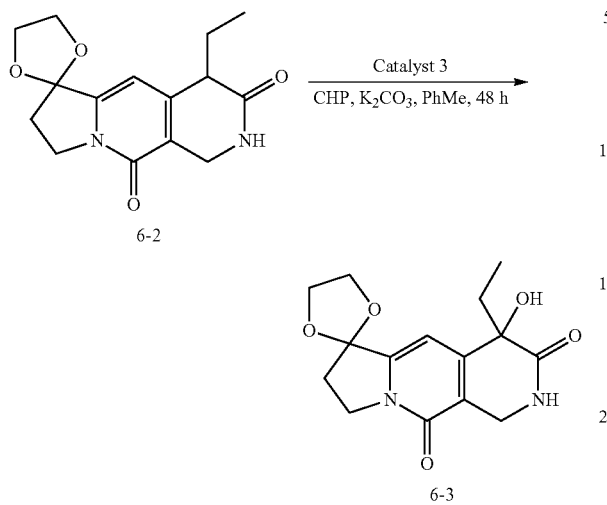

In N₂ environment, to a solution of Compound 6-2 (2.0 g, 6.9 mmol), HM-582B_24 (93 mg, 1.3 mmol) and K₂CO₃ (2.39 g, 17.3 mmol) in toluene (120 mL), CHP (cumene hydroperoxide, 2.1 g, 13.8 mmol, 2.0 eq) was added dropwise, and the reaction solution was stirred at 50° C. for 24 h. CHP (cumene hydroperoxide, 2.1 g, 13.8 mmol, 2.0 eq) was added, and the reaction solution was continued to be stirred at 50° C. for 24 h. CHP (cumene hydroperoxide, 2.1 g, 13.8 mmol, 2.0 eq) was added, and the reaction solution was continued to be stirred at 50° C. for 24 h. After LCMS monitored the completion of reaction, the reaction solution was cooled to room temperature, diluted with water (200 mL), extracted with EA (150 mL*3). The organic layer was washed with saturated Na₂SO₃ (200 mL*3), dried and concentrated to obtain a reddish-brown mixture, and further separated by silica gel column chromatography (DCM/MeOH=50/1-10/1 elution) to obtain a crude product of Compound 6-3 (354 mg, Y 17%).

The Preparation of Compound 6-4

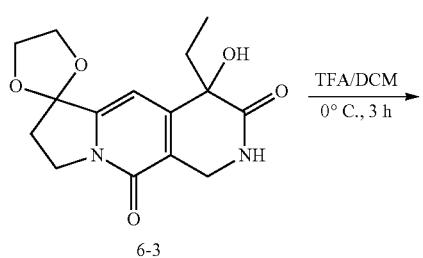

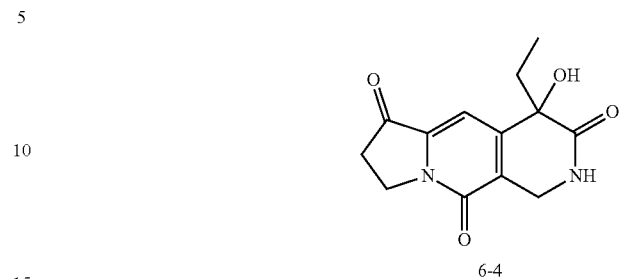

In N₂ environment, TFA (2.5 mL) was added dropwise to a solution of Compound 6-3 (354 mg, 1.16 mmol, 1.0 eq) in DCM (5 mL) at 0° C. The reaction solution was stirred at the same temperature for 3 h. After LCMS monitored the completion of reaction, the reaction solution was concentrated, and the resulting reddish-brown mixture was lyophilized at 0° C. to obtain Compound 6-4 (332 mg), which could be directly used in the next step of reaction.

The Preparation of Compound 6-6

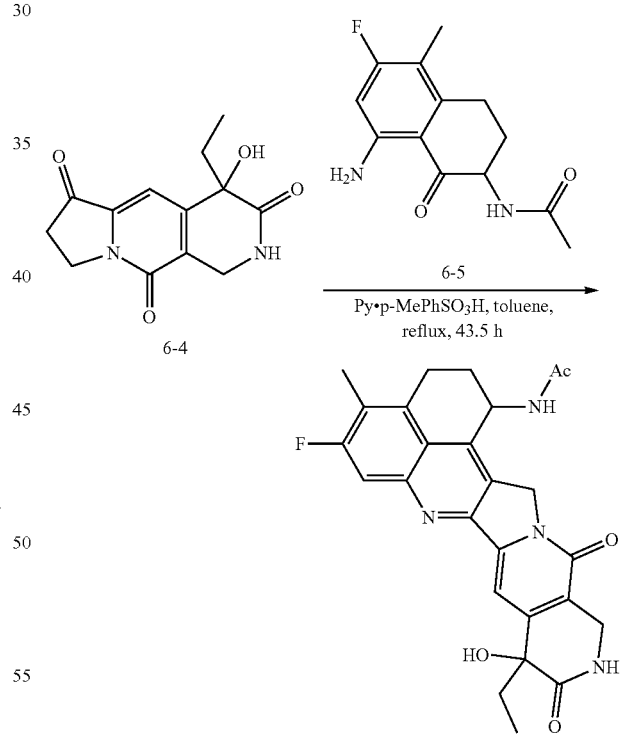

In N₂ environment, the solution of Compound 6-4 (332 mg, 1.27 mmol), Compound 6-5 (317 mg, 1.27 mmol) and PPTS (64 mg, 0.25 mmol) in toluene (9.0 mL) was heated to 125° C. (external temperature) and stirred under reflux overnight. After the reaction was complete, the reaction solution was cooled to room temperature, concentrated to dryness to obtain reddish-brown solids, and further purified by column chromatography to obtain 122 mg of Compound 6-6 (the yield was 26%), which was used directly in the next step of reaction.

The Preparation of Compounds 6-7, C-6a, and C-6b

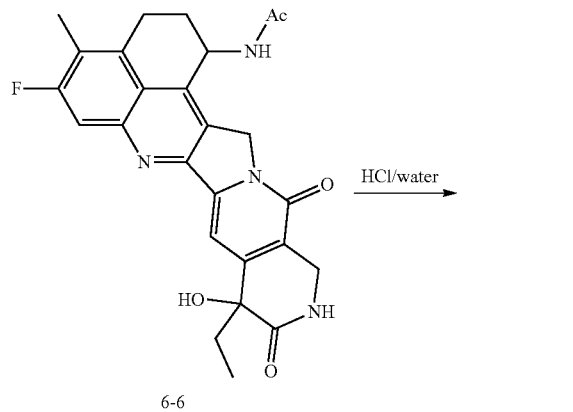

6-6

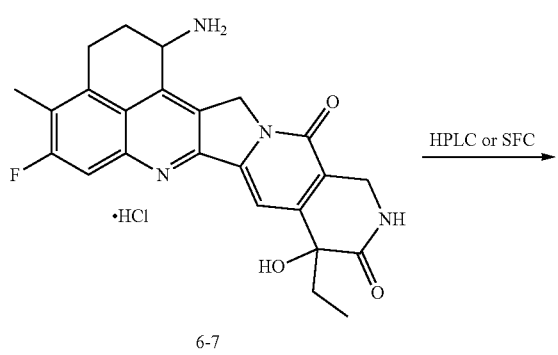

6-7

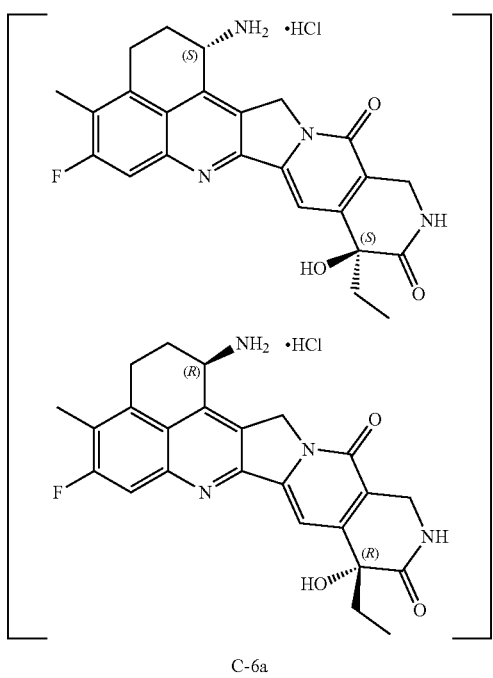

C-6a

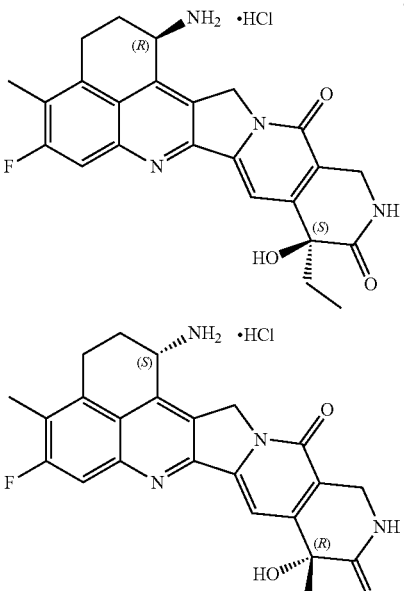

C-6b

The solution of Compound 6-6 (122 mg, 256 mmol) in dilute HCl solution (6 M in water, 5 mL) was heated under reflux for 3 h. LCMS monitored the completion of reaction. The reaction solution was directly concentrated to dryness, and two major peaks were separated by preparative liquid chromatography. The preparative solution containing the products were lyophilized to obtain P1 (C-6a, 7.2 mg) and P3 (C-6b, 8.1 mg), respectively.

LCMS (m/z)=435.2. $^1$H NMR (400 MHz, MeOD) δ 7.79 (d, J=10.7 Hz, 1H), 7.68 (s, 1H), 5.50 (dd, J=41.9, 18.8 Hz, 2H), 5.11 (s, 1H), 4.59 (d, J=18.6 Hz, 1H), 4.31 (d, J=18.6 Hz, 1H), 3.42 (d, J=18.1 Hz, 1H), 3.18 (s, 1H), 2.62 (d, J=12.7 Hz, 1H), 2.49 (s, 3H), 2.41 (s, 1H), 2.00-1.85 (m, 2H), 0.93 (t, J=7.4 Hz, 3H).

LCMS (m/z)=435.2. $^1$H NMR (400 MHz, MeOD) δ 7.79 (d, J=10.7 Hz, 1H), 7.67 (s, 1H), 5.51 (q, J=18.8 Hz, 2H), 4.58 (d, J=18.4 Hz, 1H), 4.31 (d, J=18.6 Hz, 1H), 3.41 (s, 1H), 3.18 (s, 1H), 2.60 (s, 1H), 2.50 (s, 3H), 2.41 (s, 1H), 1.99-1.85 (m, 2H), 0.92 (t, J=7.4 Hz, 3H).

Example 7: Synthesis of Compound D-2
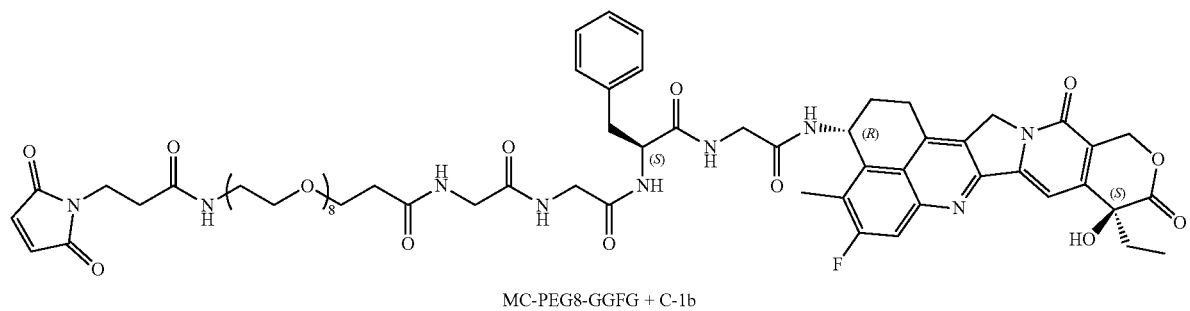
MC-PEG8-GGFG + C-1b
The Reaction Theme:
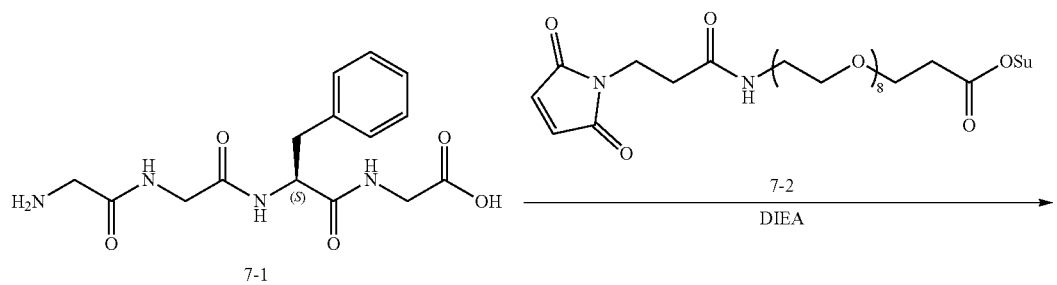
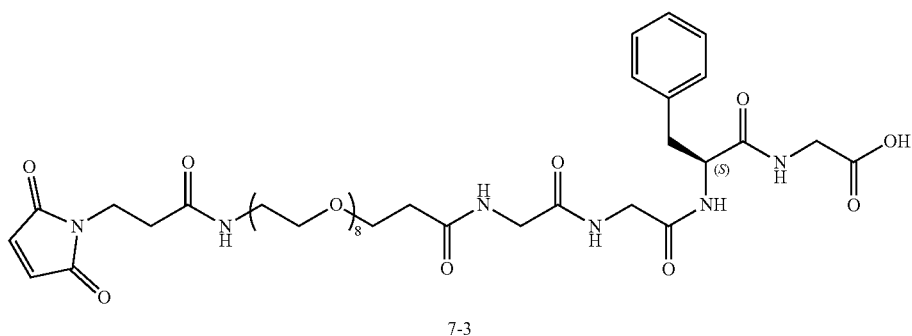
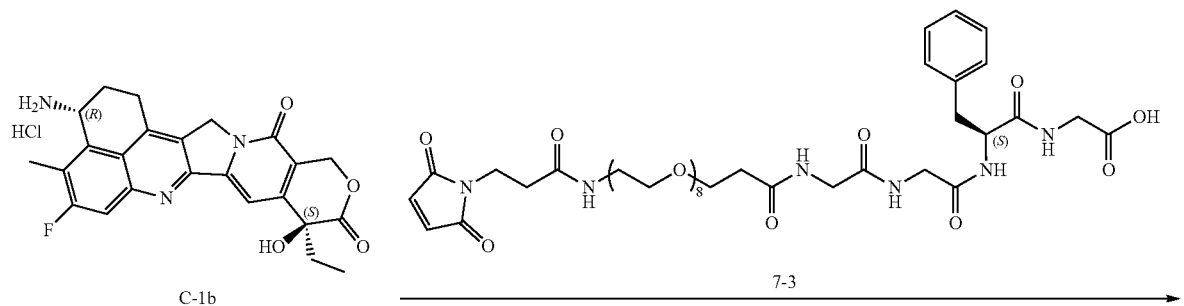

-continued

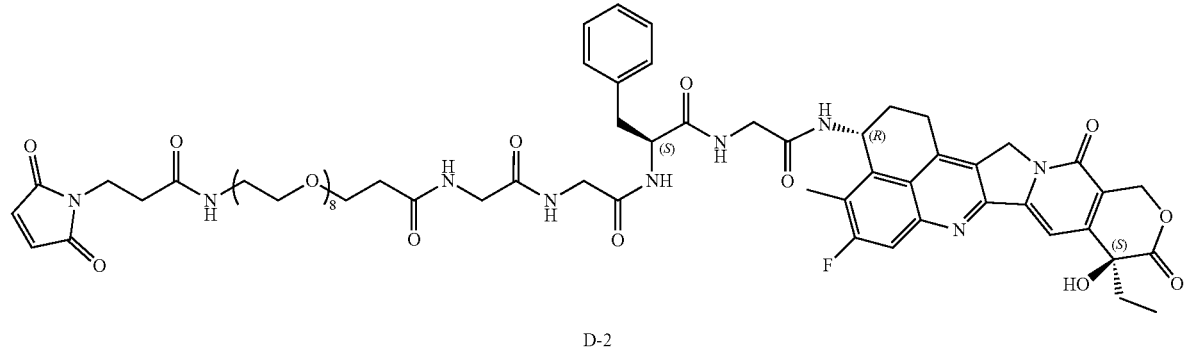

D-2

The Preparation of 7-3

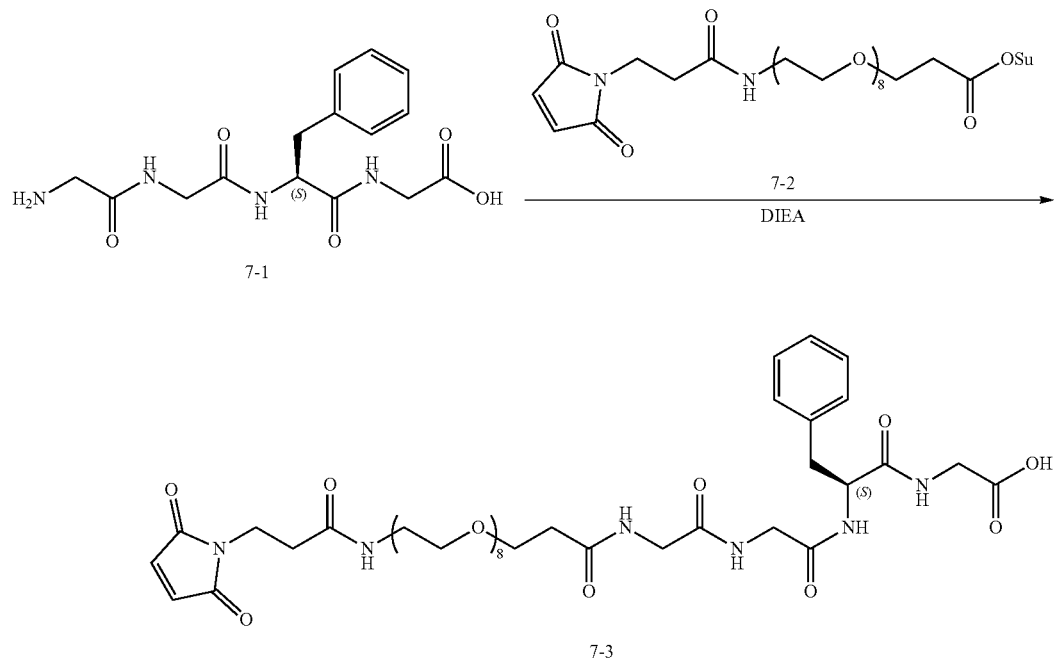

Compound 7-2 (7 g, 10.16 mmol) and Compound 7-1 (3.41 g, 10.16 mmol) were dissolved in DMF (70 mL), to which DIPEA (3.93 g, 30.5 mmol) was added. The reaction was carried for 1 hour in room temperature to obtain clear, transparent viscous product (5 g, yield: 54).

LCMS: Mobile Phase: A: water (0.01% TFA) B: ACN (0.01% TFA); Gradient: 5% to 95% B within 0.6 min; Flow Rate: 0.8 ml/min; Column: Poroshell 120 EC-C18, 2.1*50 mm, 1.9 μm A=RP=517; Oven Temperature: 45° C. MS (+)=117; Rt=0.91 min.

The Preparation of Compound D-2

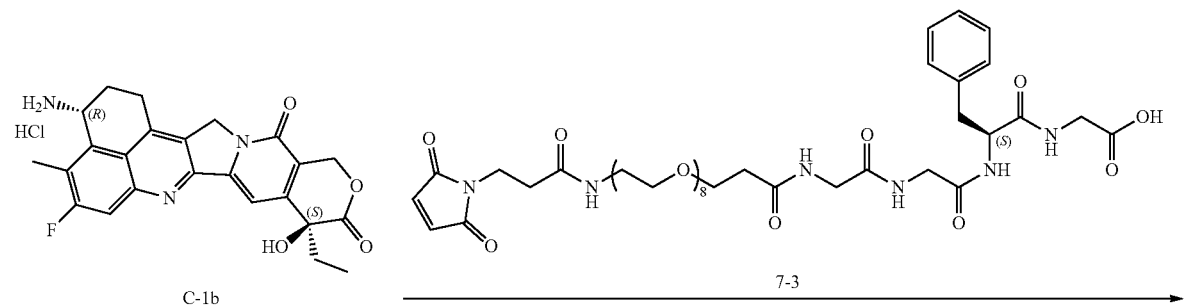

-continued

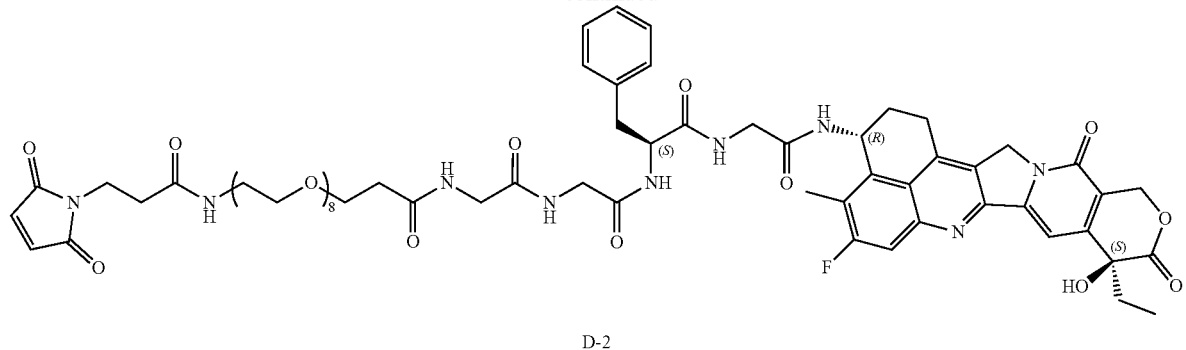

D-2

Compound C1-b (2.6 g, 5.5 mmol) and compound 7-3 (5 g, 5.5 mmol) were dissolved in DMF (50 mL). DIC (1.4 g, 11 mmol), HOBT (1.5 g, 11 mmol) and DIPEA (709 mg, 5.5 mmol) were then added to the reaction, which was stirred in room temperature for 1 hour, to obtain white product D-2 (2.1 g, yield: 28%).

LCMS: Mobile Phase: A: water (0.01% TFA) B: ACN (0.01% TFA); Gradient: 5% to 95% B within 0.6 min; Flow Rate: 0.8 ml/min; Column: Poroshell 120 EC-C18, 2.1*50 mm, 1.9 μm A=RP=517; Oven Temperature: 45° C. MS (+)=117; Rt=1.06 min.

Example 8: Synthesis of Compound D-3

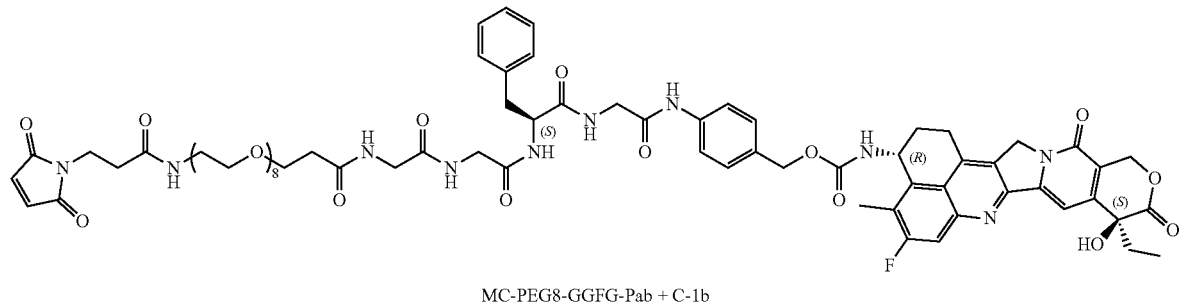

MC-PEG8-GGFG-Pab + C-1b

The Reaction Theme:

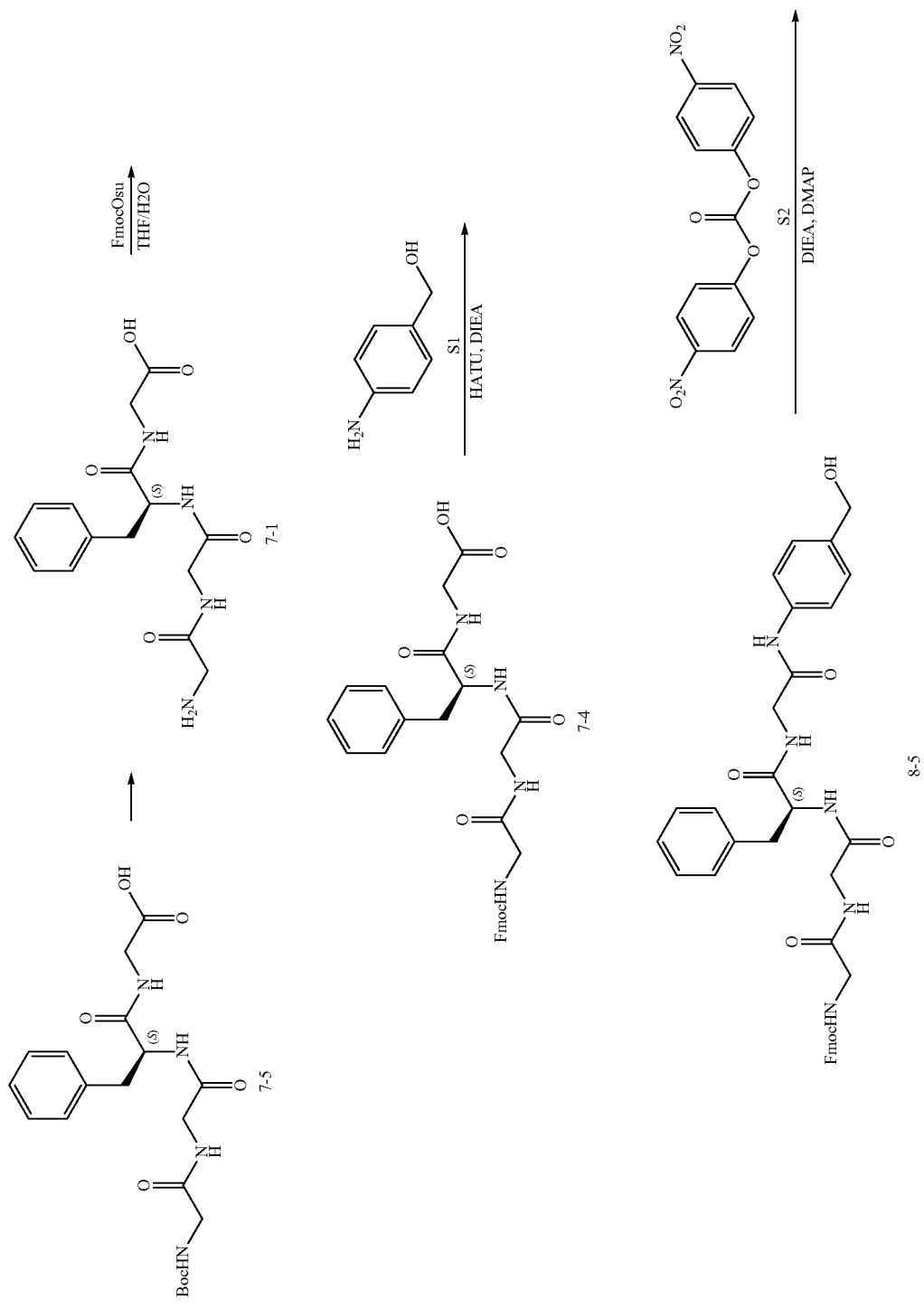

-continued
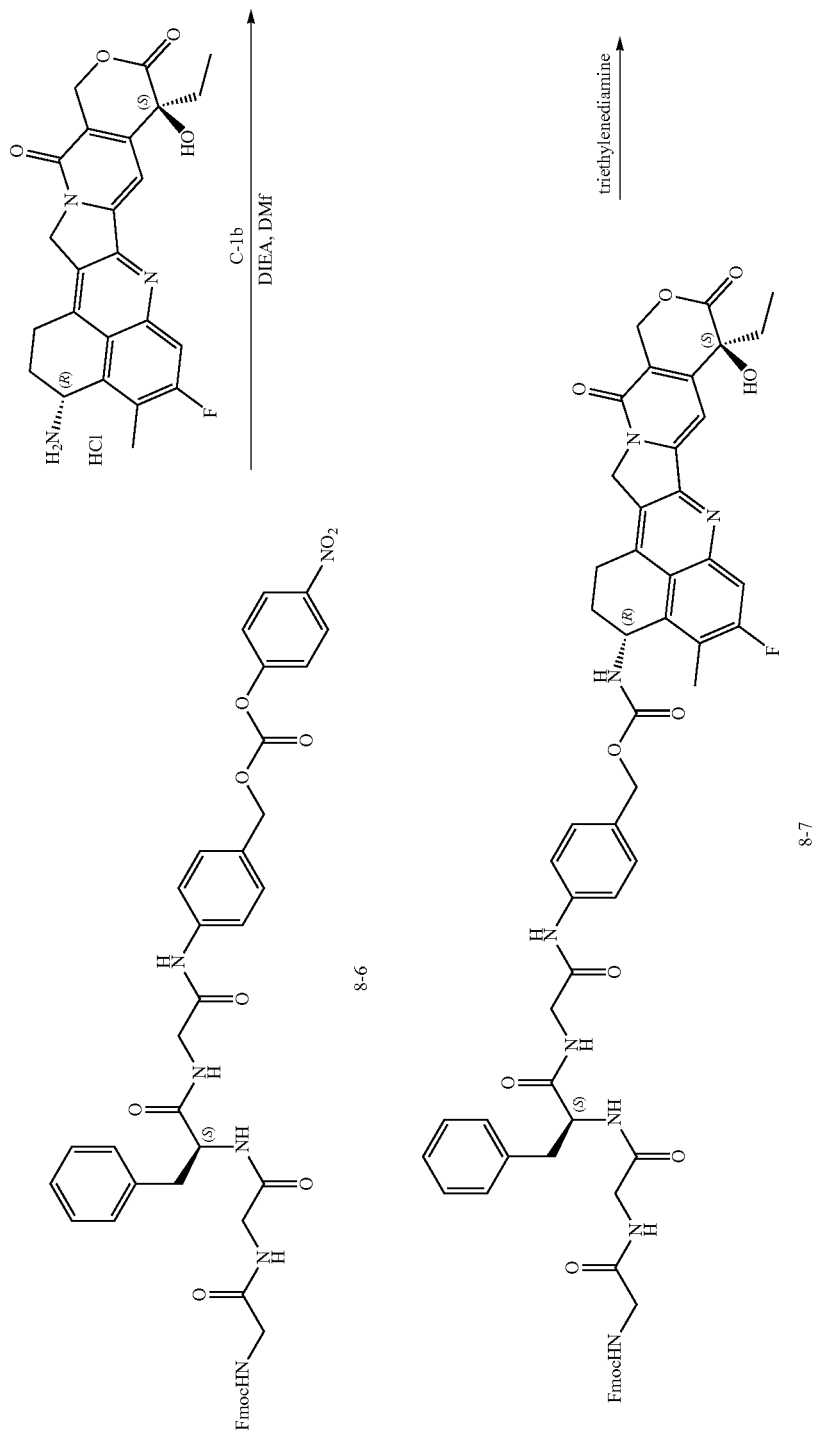

-continued
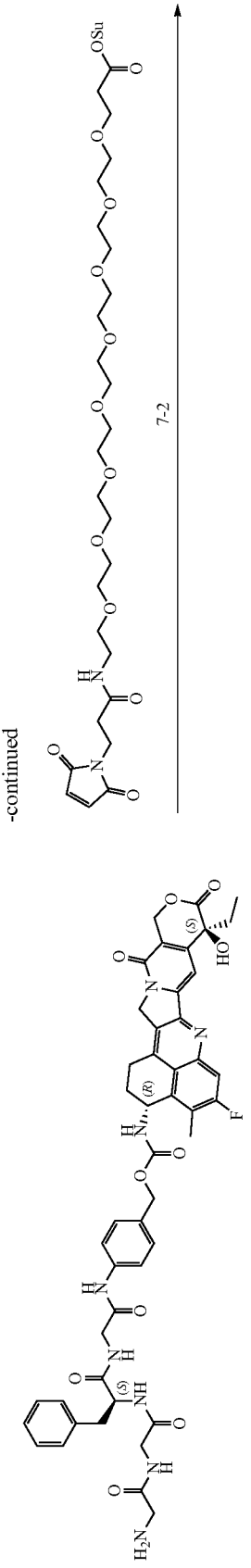
7-2
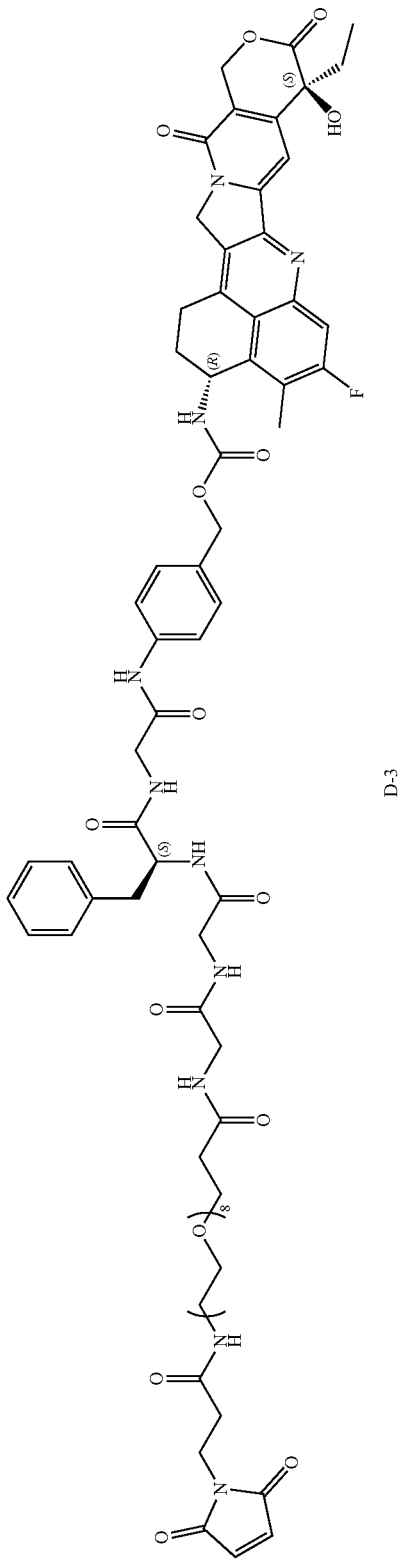
D-3
8-8

10 g of Compound 7-5 was dissolved in 100 mL DCM/TFA (1:1), stirred for 1 hour at room temperature, and was spun-dried to obtain white product 7-1 (11.5 g, yield: 100%).

LCMS: Mobile Phase: A: water (0.01% FA) B: ACN (0.01% FA); Gradient: 5% to 95% B within 0.8 min; Flow Rate: 0.8 ml/min; Column: Poroshell 120 EC-C18, 2.1*50 mm, 1.9 μm; Oven Temperature: 45° C. MS (+)=337; Rt=0.42 min.

The Preparation of 7-4

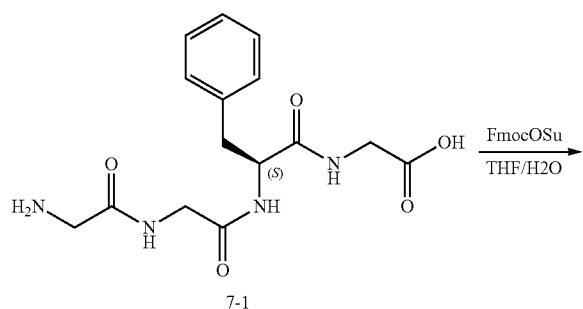

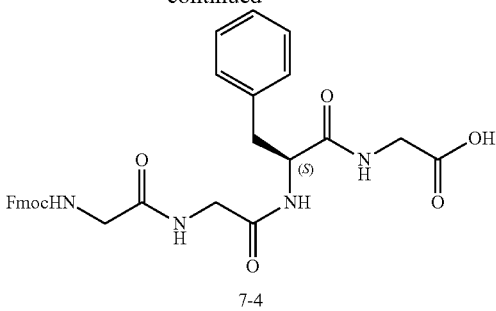

7-4

Compound 7-1 (11.5 g, 34 mmol) and FmocOSu (17.3, 51 mmol) were dissolved in THF/H₂O (120 mL, 1:1), to which NaHCO₃ (5.75 g, 68 mmol) was added. The reaction was stirred for 16 hours at room temperature, and the pH was adjusted to <5 with HCl. White solid precipitated, which was filtered and dried to obtain white final product (16.9 g, yield: 88%).

LCMS: Mobile Phase: A: water (0.01% FA) B: ACN (0.01% FA); Gradient: 5% to 95% B within 0.8 min; Flow Rate: 0.8 ml/min; Column: Poroshell 120 EC-C18, 2.1*50 mm, 1.9 μm; Oven Temperature: 45° C. MS (+)=559; Rt=1.00 min.

The Preparation of 8-5

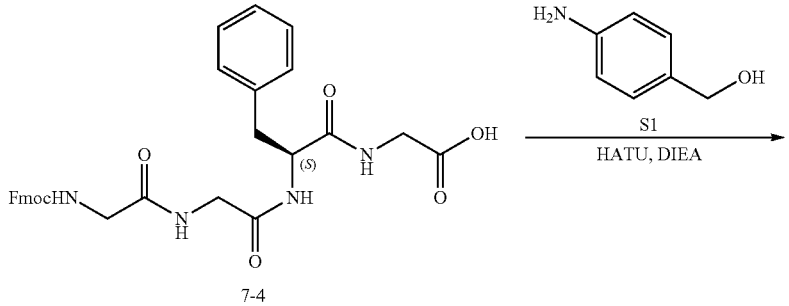

7-4

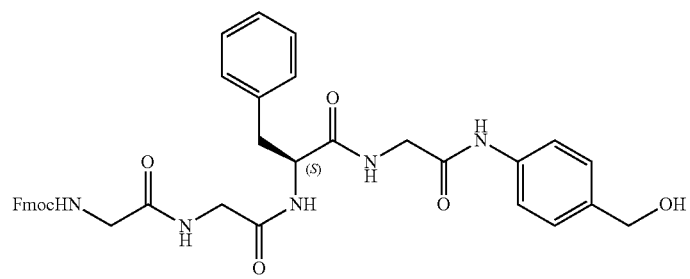

8-5

Compound 7-4 (16.8 g, 30 mmol) and S1 (4-aminobenzyl alcohol, 4.07 g, 33 mmol) were dissolved in DMF (180 mL), to which HATU (14.9 g, 39 mmol) and DIPEA (9.7 g, 75 mmol) were added. The reaction was carried out for 2 hours at room temperature.

LCMS: Mobile Phase: A: water (0.01% TFA) B: ACN (0.01% TFA); Gradient: 5% to 95% B within 1.3 min; Flow Rate: 0.8 ml/min; Column: Poroshell 120 EC-C18, 2.1*50 mm, 1.9 μm; Oven Temperature: 45° C. MS (+)=646; Rt=1.04 min.

The Preparation of 8-6

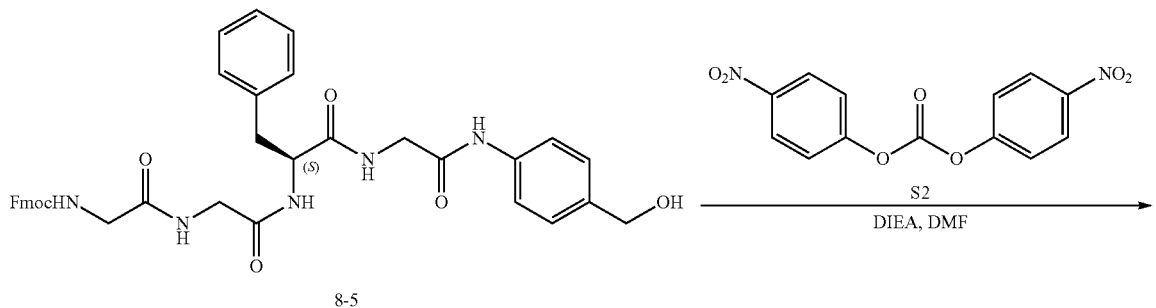

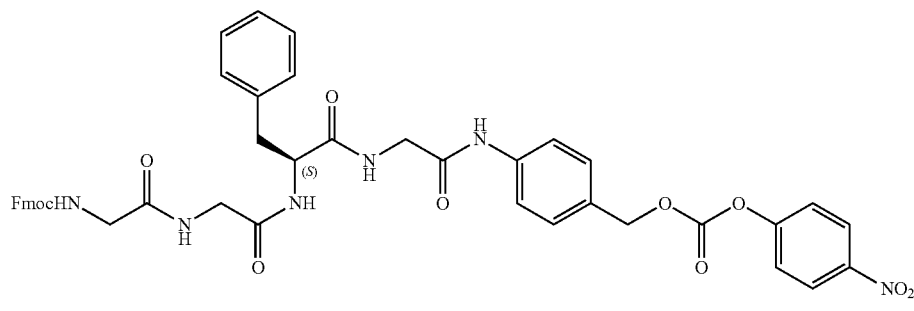

Compound 8-5 (6 g, 9 mmol) and S1 (bis (4-nitrophenyl) carbonate, 4.13 g, 13.5 mmol) were dissolved in DMF (60 mL), to which DIPEA (3.5 g, 27 mmol) was added. The reaction was carried out at room temperature for 2 hours, and the final product in white was obtained through reversed-phase purification (4.16 g, yield: 55%).

LCMS: Mobile Phase: A: water (0.01% TFA) B: ACN (0.01% TFA); Gradient: 5% to 95% B within 1.3 min; Flow Rate: 0.8 ml/min; Column: Poroshell 120 EC-C18, 2.1*50 mm, 1.9 μm; Oven Temperature: 45° C. Rt=1.23 min.

The Preparation of 8-7

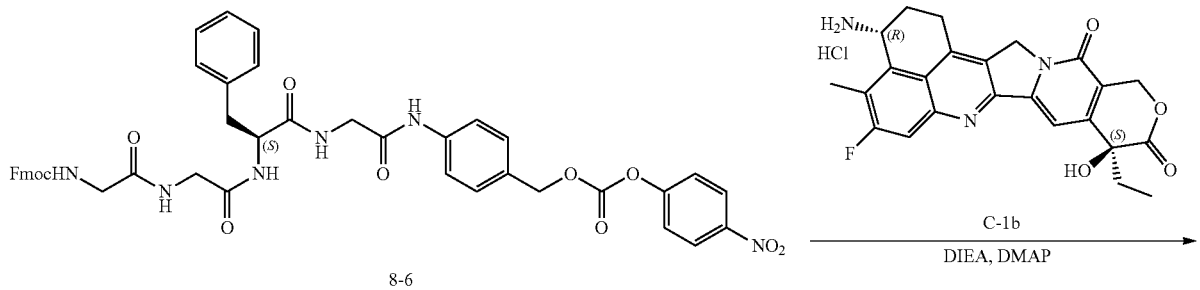

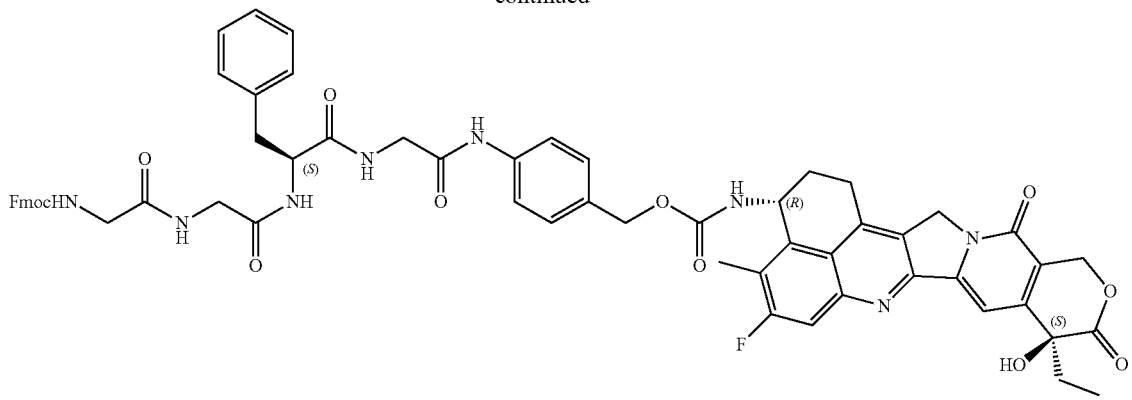

8-7

Compound 8-6 (7 g, 8.45 mmol) and compound C-1b (3.58 g, 7.6 mmol) were dissolved in DMF (70 mL), to which HOBT (2.28 g, 16.9 mmol) and DIPEA (3.27 g, 25.3 mmol) were added. The reaction was carried out at room temperature for 1 hour, and was then added to methyl tertiary ether to precipitate white solid, which was dried to obtain light brown raw product (7 g, yield: 73%).

LCMS: Mobile Phase: A: water (0.01% TFA) B: ACN (0.01% TFA); Gradient: 5% to 95% B within 2.0 min; Flow Rate: 1.2 ml/min; Column: Shim-pack Scepter C18-120, 3.0*33 mm, 3 μm; Oven Temperature: 45° C. Rt=1.57 min.

The Preparation of 8-6

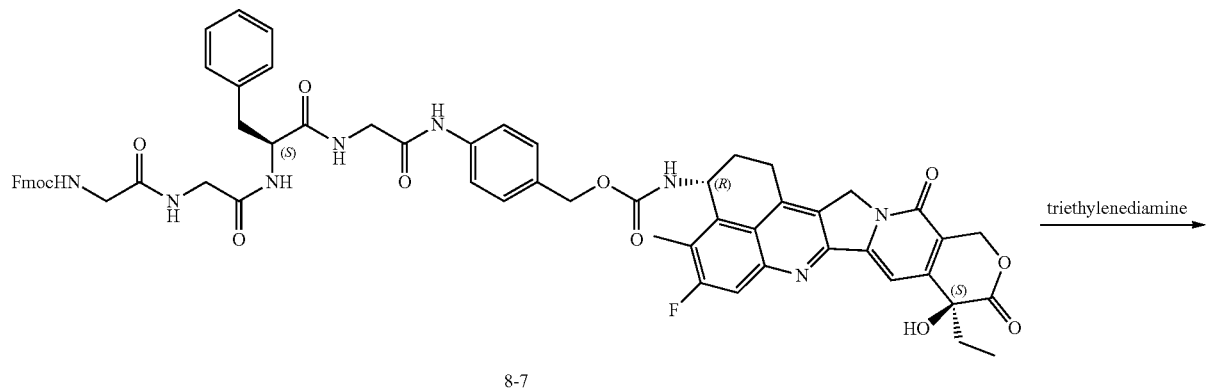

8-7

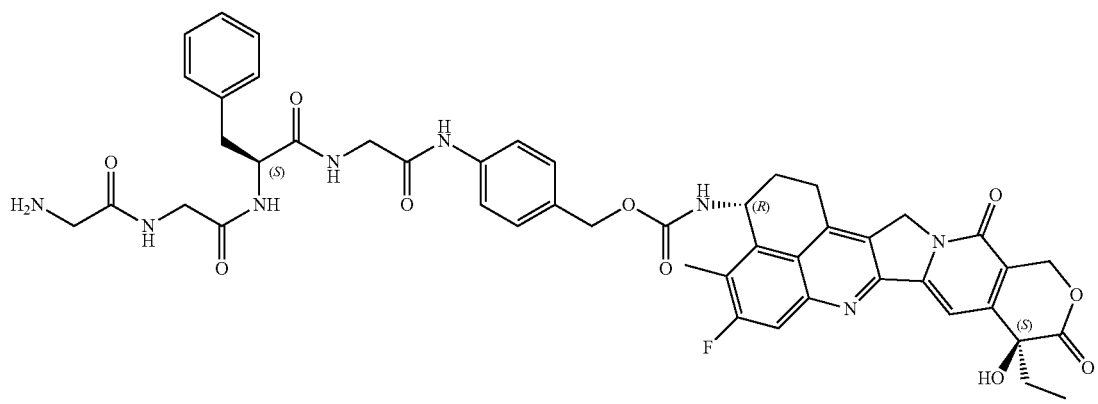

8-8

Compound 8-7 was dissolved in DMF (70 mL), and triethylenediamine (1.4 g, 12.45 mmol) was added. The reaction was carried out at room temperature for 2 hours, and the final product in white was obtained through reversed-phase purification (3.65 g, yield: 65%).

LCMS: Mobile Phase: A: water (0.01% TFA) B: ACN (0.01% TFA); Gradient: 5% to 95% B within 1.3 min; Flow Rate: 0.8 ml/min; Column: Poroshell 120 EC-C18, 2.1*50 mm, 1.9 μm; Oven Temperature: 45° C. Rt=0.93 min.

The Preparation of D-3

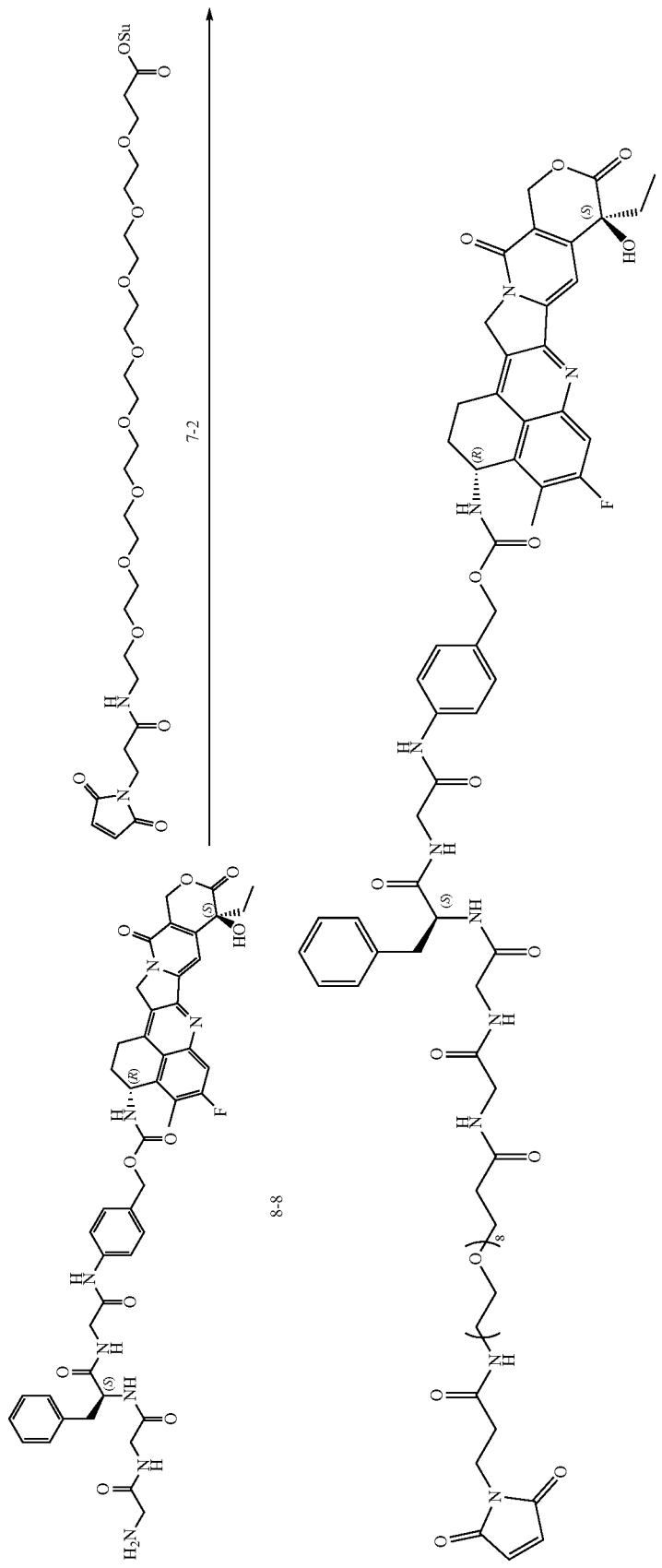

Compounds 8-8 (3.65 g, 4 mmol) and 7-2 (3.07 g, 4.45 mmol) were dissolved in DMF (40 mL), to which DIPEA (522 mg, 4 mmol) was added. The reaction was carried out at room temperature for 0.5 hours, and the final product in white was obtained through reversed-phase purification (3.1 g, yield: 52%).

LCMS: Mobile Phase: A: water (0.01% TFA) B: ACN (0.01% TFA); Gradient: 5% to 95% B within 1.3 min; Flow Rate: 0.8 ml/min; Column: Poroshell 120 EC-C18, 2.1*50 mm, 1.9 μm; Oven Temperature: 45° C. MS (+)=84; Rt=1.01 min.

Biological Assays

Example 1. Cytotoxicity Testing of Compounds

This example tested four of the compounds for their ability to induce cytotoxicity. The molecules were Compounds C-2a, C-2b, C-6a and C-6b. MMAE and DXD (exatecan derivative for ADC) were used as benchmark references.

HT-29 (colorectal cancer) and MDA-MB-468 (TNBC) cells were harvested and seeded with 3000 cell per well into 96-well cell culture plates respectively. They were then incubated at 37° C., 5% $CO_2$ for overnight. Each compound was diluted 3-fold from 500 nM, and added to each well respectively. After 5 days, 30 μL cell titer-Glo Luminescent buffer was added to each well and the plate was incubated for 20 min at room temperature. Luminescence signal was detected by the Envison microplatereader.

The results are shown in Table 1. As shown, MMAE, DXD, C-2a and C-2b inhibited cells proliferation in a concentration-dependent manner.

TABLE 1

Cytotoxicity Testing Results

| Compound | | MMAE | DXD | C-2a | C-2b | C-6a | C-6b |
|---|---|---|---|---|---|---|---|
| HT29 | IC50 | ~0.5 | 25.2 | 5.7 | 5.6 | NA | NA |
| | Min cell viability | 21.3 | 4.0 | 4.6 | 1.9 | 130.0 | 101.4 |
| MDA-MB-468 | IC50 | 0.1 | 3.2 | 1.6 | 1.0 | NA | NA |
| | Min cell viability | 4.6 | 1.2 | 0.9 | 0.9 | 15.4 | 58.9 |

In a second round of testing, C-2a and C-2b, along with 6 other compounds (C-1a, C-1b, C-3a, C-3b, C-5a, and C-4a) were tested with the same cell lines plus A549, a NSCLC cell line. The results are shown in Table 2.

TABLE 2

Second Round Cytotoxicity Testing Results

| Compound | | MMAE | DXD | C-2a | C-2b | C-1a | C-1b | C-3a | C-3b | C-5a | C-4a |
|---|---|---|---|---|---|---|---|---|---|---|---|
| HT29 | IC50 | 1.1 | 105 | 40.1 | ~52.7 | 21.1 | 18.5 | 76.6 | NA | 26.57 | NA |
| | Min cell viability | 35.5 | 11.4 | 4.8 | 3.7 | 7.7 | 4.0 | 5.1 | 14.6 | 4.4 | 99.4 |
| MDA-MB-468 | IC50 | 0.3 | 4.2 | 5.6 | 5.2 | 3.6 | 3.1 | 8.8 | 17.6 | 2.4 | 114.7 |
| | Min cell viability | 6.3 | 4.1 | 3.7 | 2.9 | 3.0 | 2.3 | 3.3 | 3.7 | 2.4 | 8.3 |
| A549 | IC50 | 2.0 | 125.7 | 18.9 | 24.2 | 16.6 | 13.7 | 36.6 | 113.6 | 22.0 | NA |
| | Min cell viability | 30.8 | 28.4 | 19.7 | 23.6 | 20.3 | 14.5 | 23.8 | 30.6 | 19.4 | 83.0 |

All of the tested compounds inhibited cells proliferation in a concentration-dependent manner.

Example 2. Binding of HER2 ADCs with Human HER2 Positive and Negative Cells

Cell based binding of antibody drug conjugates (Trastuzumab-DXd, ADC-1, ADC-2, ADC-3, ADC-4 and ADC-5) to tumor cells was assessed using flow cytometry method (all of ADC-1 through ADC-5 included trastuzumab as the antibody). Briefly, The NCI-N87, SK-BR-3, BT-474, JIMT-1 and MDA-MB-468 cells were incubated with titrated antibody drug conjugates (from 100 nM, 5 folds dilution, 8 points) at 4° C. for 60 minutes. Then the cells were washed with FACS buffer twice and stained with fluorescent conjugated secondary antibody (Alexa Fluor® 647 Goat Anti-Human IgG, Jackson, 109-605-098) at 4° C. for 60 minutes. After that the cells were washed twice and analyzed by flow cytometry.

As seen in FIGS. 1A-1E, all antibody drug conjugates (Trastuzumab-DXd, ADC-1, ADC-2, ADC-3, ADC-4 and ADC-5) could effectively bind to human Her2-expressing tumor cells in a dose dependent manner.

| | NCI-N87 | | SK-BR-3 | | BT-474 | |
|---|---|---|---|---|---|---|
| Sample | EC50 (nM) | Max (MFI) | EC50 (nM) | Max (MFI) | EC50 (nM) | Max (MFI) |
| Trastuzumab-DXd | 2.961 | 276178 | 3.021 | 220188 | 4.894 | 161192 |
| ADC-1 | 3.382 | 278250 | 3.005 | 223969 | 5.296 | 163364 |
| ADC-2 | 3.046 | 281146 | 2.773 | 228856 | 5.078 | 167755 |
| ADC-3 | 3.528 | 225645 | 3.567 | 185789 | 5.758 | 143435 |
| ADC-4 | 3.141 | 232610 | 2.785 | 198090 | 4.292 | 149506 |
| ADC-5 | 4.994 | 201273 | 5.201 | 164088 | 9.016 | 131907 |
| Isotype-DXd | N.A. | 119 | N.A. | 133 | N.A. | 121 |

| | JIMT-1 | | MDA-MB-468 | |
|---|---|---|---|---|
| Sample | EC50 (nM) | Max (MFI) | EC50 (nM) | Max (MFI) |
| Trastuzumab-DXd | 1.623 | 31787 | N.A. | 115 |
| ADC-1 | 1.743 | 31703 | N.A. | 115 |
| ADC-2 | 1.461 | 32081 | N.A. | 116 |
| ADC-3 | 1.971 | 29573 | N.A. | 115 |
| ADC-4 | 1.123 | 29765 | N.A. | 150 |
| ADC-5 | 4.308 | 26472 | N.A. | 124 |
| Isotype-DXd | N.A. | 136 | N.A. | 123 |

Example 3. Binding of ADC-3 with Drug to Antibody Ratio 4 (ADC-3-4), 6 (ADC-3-6), and (ADC-3-8) to Human HER2 Positive and Negative Cells Cell based binding of antibody drug conjugates (Trastuzumab-DXd, ADC-2, ADC-3-4 (DAR4), ADC-3-6 (DAR6), and ADC-3-8 (DAR8)) to tumor cells was assessed using flow cytometry method. Briefly, The NCI-N87, SK-BR-3, BT-474, JIMT-1, MDA-MB-231 and MDA-MB-468 cells were incubated with titrated antibody drug conjugates (from 100 nM, 5 folds dilution, 8 points) at 4° C. for 60 minutes. Then cells were washed with FACS buffer twice and stained with fluorescent conjugated secondary antibody (Alexa Fluor® 647 Goat Anti-Human IgG, Jackson, 109-605-098) at 4° C. for 60 minutes. After that the cells were washed twice and analyzed by flow cytometry.

As seen in FIGS. 2A-2F, all antibody drug conjugates (Trastuzumab-DXd, ADC-2, ADC-3-4 (DAR4), ADC-3-6 (DAR6), and ADC-3-8 (DAR8)) could effectively bind to human Her2 expressing tumor cells in a dose dependent manner.

| Sample | NCI-N87 EC50 (nM) | NCI-N87 Max (MFI) | SK-BR-3 EC50 (nM) | SK-BR-3 Max (MFI) | BT-474 EC50 (nM) | BT-474 Max (MFI) |
|---|---|---|---|---|---|---|
| Trastuzumab-DXd | 3.425 | 215714 | 4.621 | 185879 | 2.813 | 174842 |
| Isotype-DXd | N.A. | 561 | N.A. | 161 | N.A. | 179 |
| ADC-2 | 3.33 | 221679 | 4.232 | 190683 | 3.114 | 183723 |
| ADC-3-8 | 4.001 | 180484 | 5.593 | 162056 | 3.624 | 153643 |
| ADC-3-4 | 3.141 | 203221 | 4.474 | 183087 | 2.807 | 170486 |
| ADC-3-6 | 3.729 | 199957 | 4.781 | 172890 | 3.34 | 162486 |

| Sample | JIMT-1 EC50 (nM) | JIMT-1 Max (MFI) | MDA-MB-231 EC50 (nM) | MDA-MB-231 Max (MFI) | MDA-MB-468 EC50 (nM) | MDA-MB-468 Max (MFI) |
|---|---|---|---|---|---|---|
| Trastuzumab-DXd | 1.347 | 31720 | 1.575 | 2913 | N.A. | 146 |
| Isotype-DXd | N.A. | 193 | N.A. | 143 | N.A. | 150 |
| ADC-2 | 1.383 | 32549 | 1.521 | 2936 | N.A. | 147 |
| ADC-3-8 | 1.897 | 29804 | 2.112 | 2819 | N.A. | 153 |
| ADC-3-4 | 1.387 | 30625 | 1.31 | 2811 | N.A. | 156 |
| ADC-3-6 | 1.592 | 29546 | 1.659 | 2776 | N.A. | 157 |

Example 4. Cytotoxicity of HER2 ADCs on Human HER2 Positive and Negative Cells Cytotoxicity of antibody drug conjugates (Trastuzumab-DXd, ADC-1, ADC-2, ADC-3, ADC-4 and ADC-5) to human Her2 expressing tumor cells was assessed using CellTiter-Glo Luminescent Cell Viability Assay (Promega, G7573). Briefly, the NCI-N87, SK-BR-3, BT-474, JIMT-1 and MDA-MB-468 cells were incubated with titrated antibody drug conjugates (from 100 nM, 5 folds dilution, 9 points) in 96-well plates at 37° C. cell incubator for 6 days. Cell viability was evaluated using the CellTiter-Gb) kit (Promega, G7573), following the manufacturer's instruction.

As seen in FIGS. 3A-3E, SK-BR-3 cells were more sensitive to all of antibody drug conjugates (Trastuzumab-DXd, ADC-1, ADC-2, ADC-3, ADC-4 and ADC-5) than other tumor cells, and ADC-1 showed the highest in vitro antitumor ability. In NCI-N87, SK-BR-3 and BT-474 cells, ADC-1's antitumor activity was about 3-fold higher than Trastuzumab-DXd.

| Sample | NCI-N87 IC50 (nM) | NCI-N87 Min cell viability (%) | SK-BR-3 IC50 (nM) | SK-BR-3 Min cell viability (%) | BT-474 IC50 (nM) | BT-474 Min cell viability (%) |
|---|---|---|---|---|---|---|
| Trastuzumab-DXd | 0.246 | 20.5 | 0.075 | 12.9 | 0.059 | 43.4 |
| ADC-1 | 0.077 | 12.6 | 0.020 | 9.0 | 0.015 | 34.5 |
| ADC-2 | 0.105 | 14.6 | 0.046 | 11.0 | 0.030 | 45.9 |
| ADC-3 | 0.135 | 34.8 | 0.079 | 18.1 | 0.178 | 57.8 |
| ADC-4 | 0.608 | 36.2 | 0.199 | 29.6 | 0.168 | 68.6 |
| ADC-5 | N.A. | 70.1 | 0.255 | 46.4 | N.A. | 95.2 |
| Isotype-DXd | N.A. | 87.7 | N.A. | 96.2 | N.A. | 80.7 |

| Sample | JIMT-1 IC50 (nM) | JIMT-1 Min cell viability (%) | MDA-MB-468 IC50 (nM) | MDA-MB-468 Min cell viability (%) |
|---|---|---|---|---|
| Trastuzumab-DXd | N.A. | 95.3 | N.A. | 70.4 |
| ADC-1 | 0.352 | 59.6 | N.A. | 86.7 |
| ADC-2 | 0.168 | 64.2 | N.A. | 97.3 |
| ADC-3 | N.A. | 69.6 | N.A. | 33.0 |
| ADC-4 | N.A. | 96.0 | N.A. | 96.9 |
| ADC-5 | N.A. | 92.3 | N.A. | 31.5 |
| Isotype-DXd | N.A. | 99.3 | N.A. | 57.5 |

Example 5. Cytotoxicity of ADC-3 with Drug to Antibody Ratio (ADC-3-4), 6 (ADC-3-6), and 8 (ADC-3-8) on Human HER2 Positive and Negative Cells Cytotoxicity of antibody drug conjugates (Trastuzumab-DXd, ADC-2, ADC-3-4 (DAR4), ADC-3-6 (DAR6), and ADC-3-8 (DAR8)) to human Her2 expressing tumor cells was assessed using CellTiter-Glo Luminescent Cell Viability Assay (Promega, G7573). Briefly, The NCI-N87, SK-BR-3, BT-474, JIMT-1, MDA-MB-231 and MDA-MB-468 cells were incubated with titrated antibody drug conjugates, (from 100 nM, 5 folds dilution, 9 points) in 96-well plates at 37° C. cell incubator for 6 days. Cell viability was evaluated using the CellTiter-Glo kit (Promega, G7573), following the manufacturer's instruction.

As seen in FIGS. 4A-4F, SK-BR-3 cells were more sensitive to all of antibody drug conjugates (Trastuzumab-DXd, ADC-1, ADC-2, ADC-3-4, ADC-3-6, ADC-3-8, ADC-4, and ADC-5) than other tumor cells, and ADC-2 showed superior in vitro antitumor ability.

| Sample | NCI-N87 IC50 (nM) | NCI-N87 Min cell viability (%) | SK-BR-3 IC50 (nM) | SK-BR-3 Min cell viability (%) | BT-474 IC50 (nM) | BT-474 Min cell viability (%) |
|---|---|---|---|---|---|---|
| Trastuzumab-DXd | 0.2852 | 32.2 | 0.08948 | 17.6 | 0.05995 | 55.9 |
| Isotype-DXd | N.A. | 89.3 | N.A. | 92.9 | N.A. | 103.2 |
| ADC-2 | 0.1472 | 20.1 | 0.06765 | 17.9 | 0.0344 | 48.2 |
| ADC-3-8 | 0.1722 | 38.7 | 0.07956 | 22.0 | 0.243 | 57.1 |
| ADC-3-4 | 0.441 | 41.2 | 0.181 | 29.0 | N.A. | 76.4 |
| ADC-3-6 | 0.3747 | 39.5 | 0.1041 | 23.9 | 1.073 | 57.0 |

| Sample | JIMT-1 IC50 (nM) | JIMT-1 Min cell viability (%) | MDA-MB-231 IC50 (nM) | MDA-MB-231 Min cell viability (%) | MDA-MB-468 IC50 (nM) | MDA-MB-468 Min cell viability (%) |
|---|---|---|---|---|---|---|
| Trastuzumab-DXd | N.A. | 91.9 | N.A. | 94.5 | N.A. | 85.5 |

-continued

| | | | | | | |
|---|---|---|---|---|---|---|
| Isotype-DXd | N.A. | 95.8 | N.A. | 85.5 | N.A. | 65.1 |
| ADC-2 | 0.2134 | 46.6 | N.A. | 95.3 | N.A. | 106.6 |
| ADC-3-8 | N.A. | 50.5 | N.A. | 54.4 | N.A. | 14.3 |
| ADC-3-4 | N.A. | 81.6 | N.A. | 89.3 | N.A. | 70.1 |
| ADC-3-6 | N.A. | 59.7 | N.A. | 74.0 | N.A. | 28.5 |

Example 6. Bystander Killing Effect of HER2 ADCs on Human HER2 Negative MDA-MB-468 Cells Bystander killing effect of antibody drug conjugates (Trastuzumab-DXd, ADC-1, ADC-2 and ADC-3) to human Her2 negative tumor cells (MDA-MB-468) was assessed using CellTiter-Glo Luminescent Cell Viability Assay (Promega, G7573). Briefly, The SK-BR-3 cells (5000 cells/well) were incubated with titrated antibody drug conjugates (from 100 nM, 5 folds dilution, 9 points) in 96-well plates at 37° C. cell incubator for 6 days. Then the cell culture supernatant was transferred to MDA-MB-468 cell culture (2000 cells/well) for another 6-day incubation. Cell viability was evaluated using the CellTiter-Glo kit (Promega, G7573), following the manufacturer's instruction.

Figure 5:
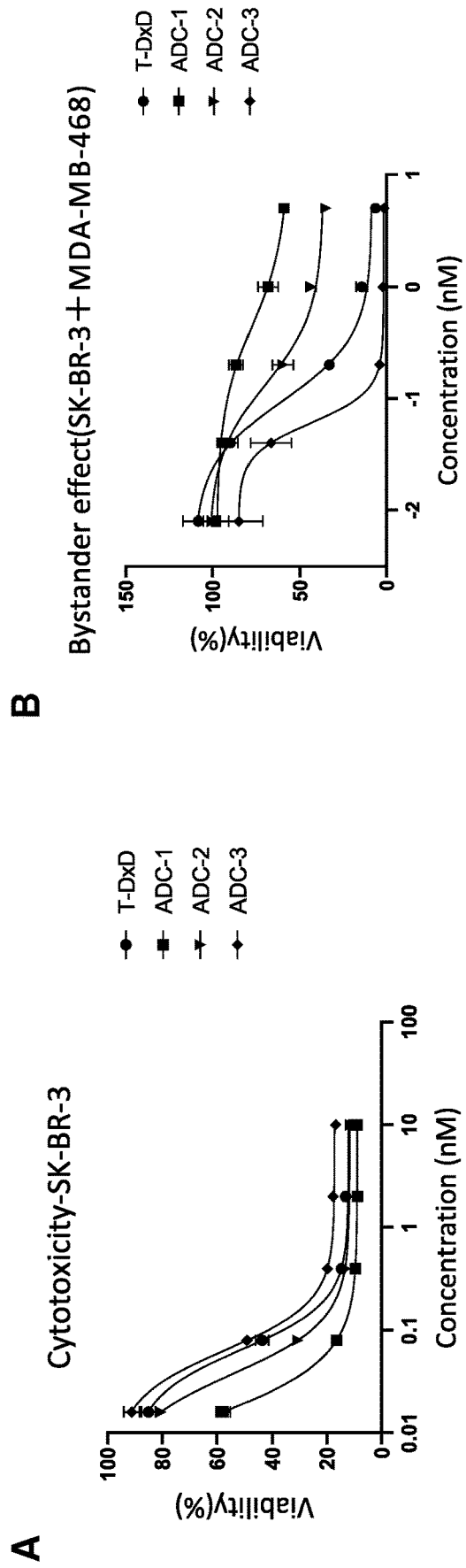
FIG. 5A and FIG. 5B show bystander killing effect of HER2 antibody drug conjugates on human HER2 negative MDA-MB-468 cells.

As shown in FIGS. 5A and 5B, ADC-1 and ADC-2 had more potent cytotoxicity against the target SK-BR-3 cells than Trastuzumab-DXd (T-DXd), and all of ADC-1, ADC-2 and ADC-3 exhibited less bystander effects than Trastuzumab-DXd. In particular, ADC-1 had the most outstanding performance in both cell lines.

Example 7. Bystander Effect of ADC-3 with Drug to Antibody Ratio 4, 6, 8 (DAR 4, 6, 8) on Human HER2 Negative MDA-MB-468 Cells Bystander killing effect of antibody drug conjugates (Trastuzumab-DXd, ADC-2, ADC-3 (DAR4), ADC-3 (DAR6), ADC-3 (DAR8)) to human Her2 negative tumor cells (MDA-MB-468) and human Her2 low expressing tumor cells (MDA-MB-231) was assessed using CellTiter-Glo Luminescent Cell Viability Assay (Promega, G7573). Briefly, the SK-BR-3 cells (5000 cells/well) were incubated with titrated antibody drug conjugates (from 100 nM, 5 folds dilution, 9 points) in 96-well plates at 37° C. cell incubator for 6 days. Then the cell culture supernatant was transferred to MDA-MB-468 cell culture (2000 cells/well) for another 6-day incubation. Cell viability was evaluated using a CellTiter-Glo kit (Promega, G7573), following the manufacturer's instruction.

Figure 6:
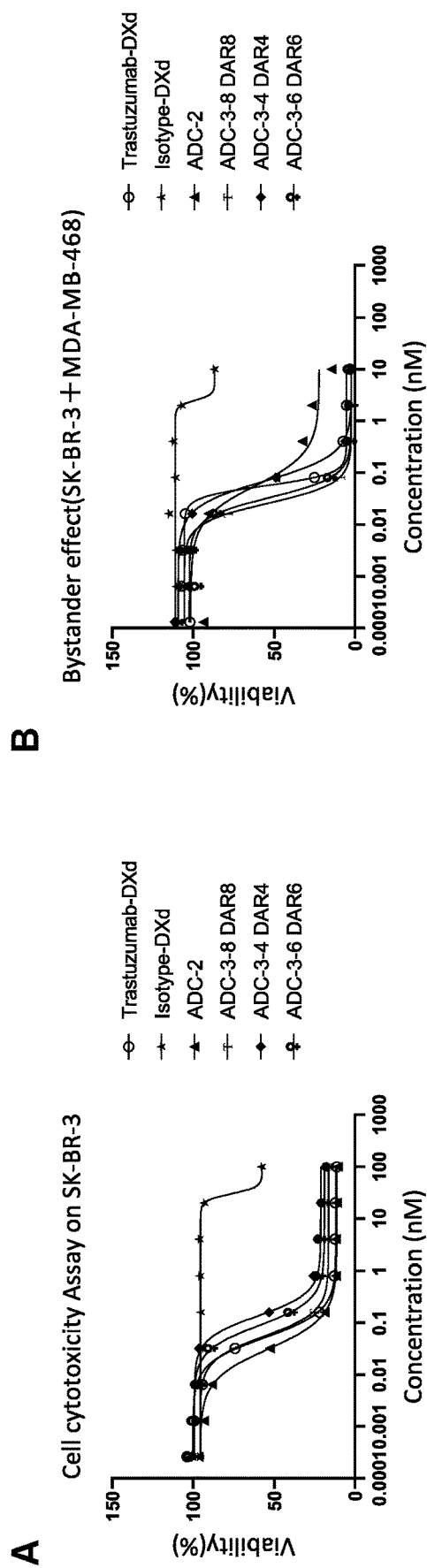
FIG. 6A and FIG. 6B show bystander effect of HER2 antibody drug conjugates with a drug to antibody ratio of 4 (ADC-3-4), 6 (ADC-3-6), and 8 (ADC-3-8) on human HER2 negative MDA-MB-468 cells.

As seen in FIGS. 6A and 6B, ADC-2 had stronger targeted cytotoxicity and more mild bystander effects than Trastuzumab-DXd, while ADC-3, at different DAR, was as good as Trastuzumab-DXd in both experiments.

Example 8. Comparison of Payload in JIMT-1 CDX Mode—Linked with Trastuzumab

NOG mice were inoculated with 8 million JIMT-1 cells for each individual. When the tumor size reached approximately 100 mm³, intravenous injection of Trastuzumab-DXd and ADC-2 were administered once a week for a total of three weeks. Tumor sizes were measured three times weekly.

Figure 7:
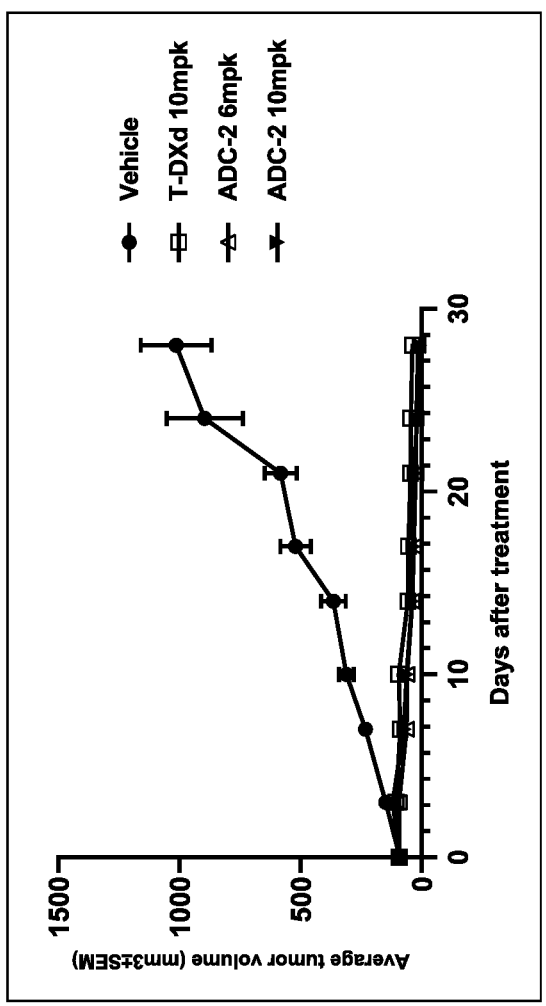
FIG. 7 shows a comparison of ADC-2 with Trastuzumab-DXd in JIMT-1 CDX mode.

As seen in FIG. 7, the tested ADC molecules had similar in vivo anti-tumor effects, even though, in one of the tests, ADC-2 (6 mpk) was used at a lower dose than Trastuzumab-DXd (10 mpk).

The present disclosure is not to be limited in scope by the specific embodiments described which are intended as single illustrations of individual aspects of the disclosure, and any compositions or methods which are functionally equivalent are within the scope of this disclosure. It will be apparent to those skilled in the art that various modifications and variations can be made in the methods and compositions of the present disclosure without departing from the spirit or scope of the disclosure. Thus, it is intended that the present disclosure cover the modifications and variations of this disclosure provided they come within the scope of the appended claims and their equivalents.

All publications and patent applications mentioned in this specification are herein incorporated by reference to the same extent as if each individual publication or patent application was specifically and individually indicated to be incorporated by reference.

The invention claimed is:

1. A compound of Formula III or IV:

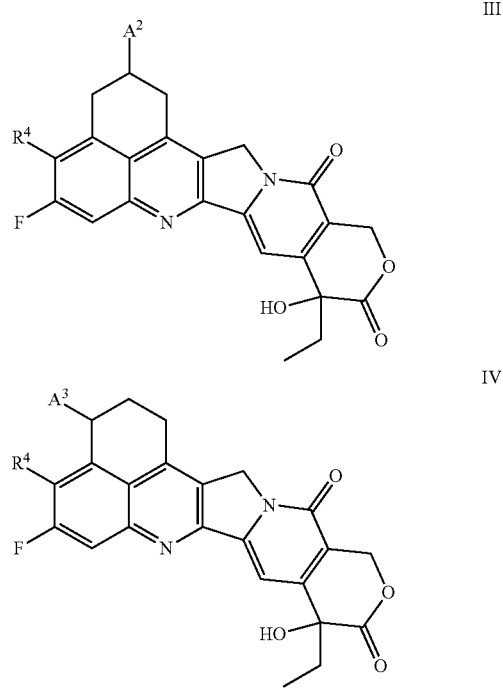

or stereoisomer or pharmaceutically acceptable salt thereof, wherein:

$A^2$ is —$NHR^2$, where $R^2$ is hydrogen, —$C_6$ aryl-$C_{1-6}$ alkyl-$NH_2$, —C(O) $R^5$, or —$C_6$ aryl-$C_{1-6}$ alkyl-NHC(O)$R^5$;

$A^3$ is —$NHR^3$, where $R^3$ is hydrogen, —$C_6$ aryl-$C_{1-6}$ alkyl-$NH_2$, —C(O) $R^5$, or —$C_6$ aryl-$C_{1-6}$ alkyl-NHC(O)$R^5$;

$R^4$ is —$C_{1-6}$ alkyl;

$R^5$ is -L-$R^6$;

L is a linker moiety; and $R^6$ is hydrogen or heterocyclyl, wherein said heterocyclyl is optionally covalently linked to an antibody or antigen-binding fragment.

2. The compound of claim 1, wherein the compound is represented by Formula III:

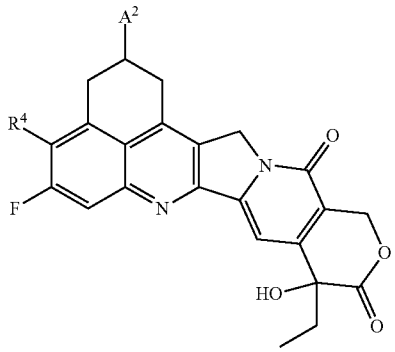

or stereoisomer or pharmaceutically acceptable salt thereof.

3. The compound of claim 1, wherein the compound is represented by Formula IV:

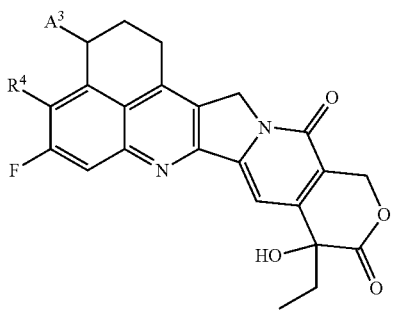

or stereoisomer or pharmaceutically acceptable salt thereof.

4. The compound of claim 3, wherein $R^5$ is -$L^1$-(AA)$_n$-$L^2$-$R^6$; and
$L^1$ is $C_{1-20}$ alkylene or $C_{2-20}$ heteroalkylene,
n is 0, 1, 2, 3, 4, 5, or 6;
each AA is independently an amino acid; and
$L^2$ is $C_{1-40}$ alkylene or $C_{2-40}$ heteroalkylene, wherein the $C_{1-40}$ alkylene or $C_{2-40}$ heteroalkylene is optionally substituted with one or more oxo.

5. The compound of claim 4 wherein $L^1$ is $C_{1-20}$ alkylene.

6. The compound of claim 4, wherein $L^1$ is $C_{2-20}$ heteroalkylene.

7. The compound of claim 4, wherein $L^1$ is —(CH$_2$)$_p$—$X^1$—(CH$_2$)$_q$—$X^2$—* or —$X^1$—(CH$_2$)$_p$-phenylene-(CH$_2$)$_q$—$X^2$—*; wherein the * bond is attached to the -(AA)$_n$-$L^2$-$R^6$:
$X^1$ is a bond, —O—, —S—, or —NH—;
$X^2$ is a bond, —O—, —S—, or —NH—;
p is 1, 2, 3, or 4; and
q is 1, 2, 3, or 4.

8. The compound of claim 7, wherein $L^1$ is —(CH$_2$)$_p$—O—(CH$_2$)$_q$—NH—*.

9. The compound of claim 4, wherein each AA is independently selected from Gly and Phe.

10. The compound of claim 4, wherein -(AA)$_n$- is -GFGG- or -FGG-.

11. The compound of claim 4, wherein $L^2$ is $C_{1-40}$ alkylene optionally substituted with one or more oxo.

12. The compound of claim 4, wherein $L^2$ is —C(O)—$C_{0-39}$ alkylene.

13. The compound of claim 4, wherein $L^2$ is —C(O)—(CH$_2$CH$_2$O)$_{1-10}$—CH$_2$CH$_2$—.

14. The compound of claim 4, wherein $R^4$ is methyl.

15. The compound of claim 4, wherein $R^5$ is
—(CH$_2$)$_p$—O—(CH$_2$)$_q$—NH-(AA)$_n$-C(O)—(CH$_2$CH$_2$O)$_{1-10}$—CH$_2$CH$_2$-$R^6$.

16. The compound of claim 4, wherein $R^6$ is

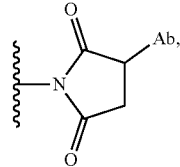

wherein Ab is an antibody or an antigen-binding fragment.

17. The compound of claim 4, wherein $A^3$ is —NH$_2$.

18. The compound of claim 17, wherein $R^4$ is methyl.

19. The compound of claim 4, wherein the compound is selected from the group consisting of:

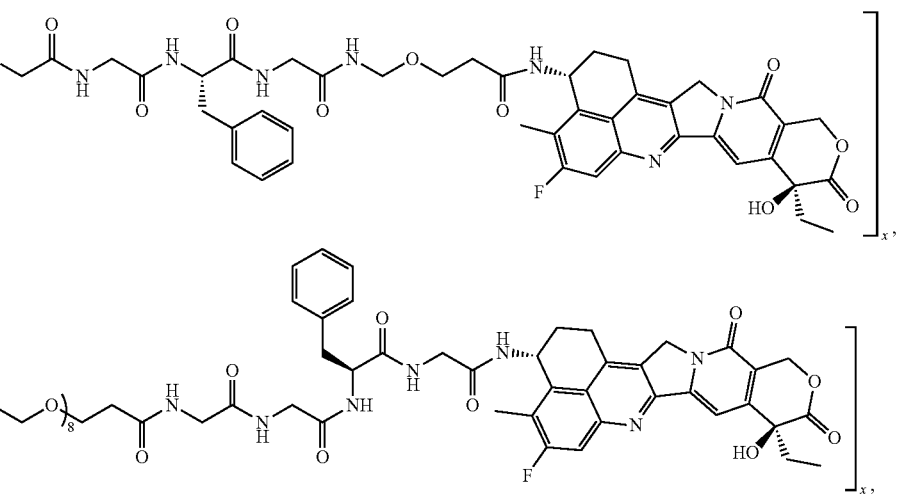

-continued
and
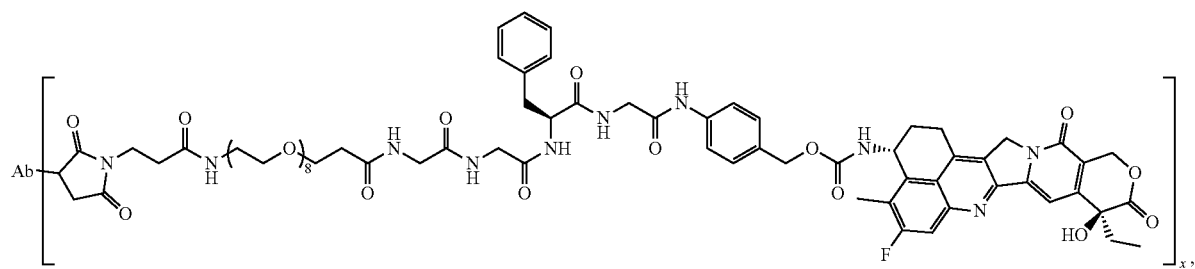
wherein Ab is an antibody or an antigen-binding fragment thereof; and x is 4-8.